(12) United States Patent
Duchaussoy et al.

(10) Patent No.: US 9,527,930 B2
(45) Date of Patent: Dec. 27, 2016

(54) FGF RECEPTOR-ACTIVATING N-SULFATE OLIGOSACCHARIDES, PREPARATION THEREOF, AND THERAPEUTIC USE THEREOF

(75) Inventors: Philippe Duchaussoy, Paris (FR); Pierre Fons, Paris (FR); Alexandre Froidbise, Paris (FR)

(73) Assignee: SANOFI, Paris (FR)

( * ) Notice: Subject to any disclaimer, the term of this patent is extended or adjusted under 35 U.S.C. 154(b) by 779 days.

(21) Appl. No.: 13/369,677

(22) Filed: Feb. 9, 2012

(65) Prior Publication Data

US 2012/0202769 A1     Aug. 9, 2012

Related U.S. Application Data

(63) Continuation of application No. PCT/FR2010/051702, filed on Aug. 12, 2010.

(30) Foreign Application Priority Data

Aug. 14, 2009    (FR)  .................................... 09 03969

(51) Int. Cl.
    *A61K 31/737*      (2006.01)
    *A61K 31/7028*      (2006.01)
    (Continued)

(52) U.S. Cl.
    CPC ......... *C08B 37/0063* (2013.01); *A61K 31/737* (2013.01); *C07H 11/00* (2013.01);
    (Continued)

(58) Field of Classification Search
    CPC ..... A61K 31/737; C07H 11/00; C07H 15/203; C07H 15/04; C08B 37/0075; C08B 37/0063
    (Continued)

(56) References Cited

U.S. PATENT DOCUMENTS 5,514,659 A    5/1996   Petitou et al.
6,528,497 B1    3/2003   Basten et al.
(Continued)

FOREIGN PATENT DOCUMENTS

EP     0300099     1/1989
EP     0529715     3/1993
(Continued)

OTHER PUBLICATIONS

Lubineau et al. (Chemistry—A European Journal (2004), 10(17), 4265-4282).*

(Continued)

Primary Examiner — Shaojia Anna Jiang
Assistant Examiner — Michael C Henry
(74) Attorney, Agent, or Firm — Morrison & Foerster LLP

(57) ABSTRACT

The invention relates to FGF receptor-activating N-sulfate oligosaccharides having Formula (I), wherein $R_1$, $R_4$, $R_6$, and $R_8$ are —$OSO_3^-$ or hydroxyl groups, $R_2$ is an —O-alkyl group or a monosaccharide having Formula (II), $R_3$ is a disaccharide having Formula (III), $R_5$ is a disaccharide having Formula (IV), $R_7$ is a hydroxyl group or a disaccharide having Formula (VI), and $R_9$ is a hydroxyl or —O-alkyl group or a disaccharide having Formula (VII), where $R_{10}$— is an —O-alkyl group. The invention further relates to the preparation of said oligosaccharides and to the therapeutic use thereof.

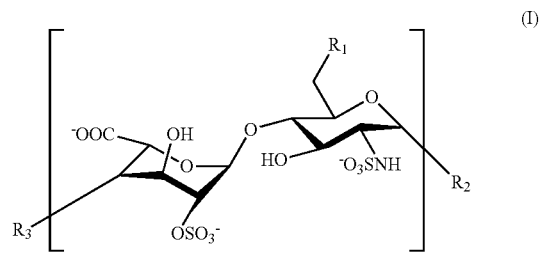

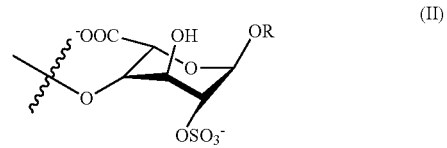

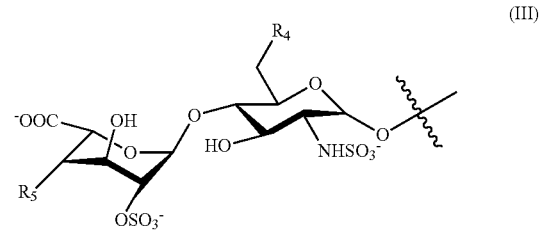

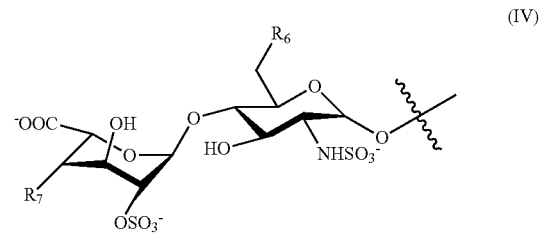

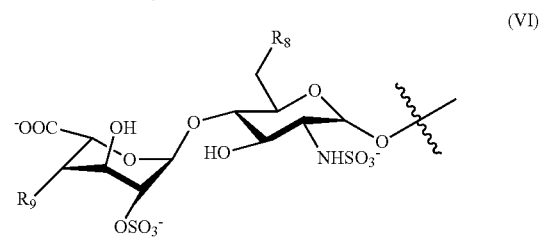

(Continued)

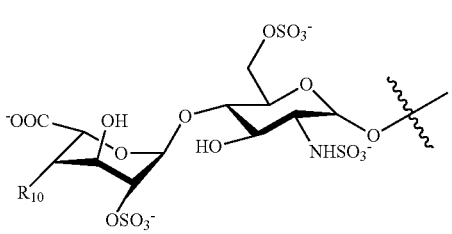

(VII)

8 Claims, No Drawings

(51) Int. Cl.
A61K 31/715 (2006.01)
C07H 15/18 (2006.01)
C07H 15/04 (2006.01)
C08B 37/00 (2006.01)
C07H 11/00 (2006.01)
C07H 15/203 (2006.01)

(52) U.S. Cl.
CPC ........... *C07H 15/04* (2013.01); *C07H 15/203* (2013.01); *C08B 37/0075* (2013.01)

(58) Field of Classification Search
USPC ... 514/25, 54; 536/4.1, 55.1, 54, 123.1, 122, 536/120, 121
See application file for complete search history.

(56) References Cited

U.S. PATENT DOCUMENTS

| | | | |
|---|---|---|---|
| 6,534,481 | B1 | 3/2003 | Driguez et al. |
| 6,617,316 | B1 | 9/2003 | Mourier et al. |
| 2004/0068108 | A1 | 4/2004 | Duchaussoy et al. |
| 2006/0079483 | A1 | 4/2006 | Hung et al. |
| 2007/0270354 | A1* | 11/2007 | Petitou et al. ............. 514/23 |

FOREIGN PATENT DOCUMENTS

| | | |
|---|---|---|
| EP | 0621282 | 10/1994 |
| EP | 0649854 | 4/1995 |
| FR | 2800074 | 4/2001 |
| WO | WO 92/18546 A1 | 10/1992 |
| WO | WO 98/03554 A1 | 1/1998 |
| WO | WO 99/36443 A1 | 7/1999 |
| WO | WO 2006/021653 A2 | 3/2006 |
| WO | WO 2011/018587 A3 | 2/2011 |

OTHER PUBLICATIONS

Lee et al. (Journal of the American Chemical Society (2004), 126(2), 476-477).*
Saxena et al. (Journal of Biological Chemistry (2010), 285(34), 26628-26640).*
Gent et al. (J. Chem. Soc., Perkin Trans. 1, 1972, 1535-1542).*
Tabeur et al. (Bioorganic & Medicinal Chemistry (1999), 7(9), 2003-2012).*
Van Boeckel, et al., The Unipue Antithrombin III Binding Domain of Heparin: A Lead to New Synthetic Antithrombotics, Angewandte Chemie, International Edition in English, vol. 32, No. 12, (1993), pp. 1671-1690.
Alavi, et al., Role of Rat in Vascular Protection from Distinct Apoptotic Stimuli, Science, vol. 301, No. 94, (2003), pp. 94-96.
Andrade, et al., Sponge-Induced Angiogenesis in Mice and the Pharmacological Reactivity of the Neovasculature Quantitated by a Fluorimetric Method, Microvascular Research, vol. 54, pp. 253-261. (1997).
Boons, Strategies in Oligosaccharide Syntheis, Tetrahedron, vol. 52, No. 4, pp. 1095-1121, (1996).
Codee, et al., The Sythesis of Well-Defined Heparin and Heparan Sulfate Fragments, Drug Discovery Today: Technologies, vol. 1, No. 3, (2004), pp. 317-326.
Cuevas, et al., Basic Fibroblast Growth Factor (FGF) Promotes Cartilage Repair in Vivo, Biochemical and Biophysical Research Communication, pp. 611-618, vol. 156, No. 2, (1998).
Faktorovich, et al., Basic Fibroblast Growth Factor and Local Injury Protect Photoreceptors from Light Damage in the Rat, The Journal of Neuroscience, vol. 12, No. 9, pp. 3554-3567, (1992).
Fibbi, et al., Growth Factor-Dependent Proliferation and Invasion of Muscle Satellite Cells Require the Cell-Associated Fibrinolytic System, Biol. Chem., vol. 383, pp. 127-136, (2002).
Hamacher, et al., Tumor Necrosis Factor-a and Angiostatin Are Mediators of Endothelial Cytotoxicity in Eronchoalveolar Lavages of Patients With Acute Respiratory Distress Syndrome, Am. J. Respir. Crit. Care Med., vol. 166, pp. 651-656, (2002).
Hendel, et al., Effect of Intracoronary Recombinant Human Vascular Endothelial Growth Factor on Myocardial Perfusion : Evidence for a Dose-Dependent Effect, Circulation, (2000), vol. 101, pp. 118-121.
Kato, et al., Sulfated Proteoglycan Synthesis by Confluent Cultures of Rabbit Costal Chondrocytes Grown in the Presence of Fibroblast Growth Factor, The Journal of Cell Biology, vol. 100, (1985), pp. 477-485.
Kawaguchi, et al., Acceleration of Fracture Healing in Nonhuman Primates by Fibroblast Growth Factor-2, The Journal of Clinical Endocrinology & Metabolism, vol. 86, No. 2, pp. 875-880, (2001).
Khurana, et al., Insights from Angiogenesis Trials Using Fibroblast Growth Factor for Advanced Arteriosclerotic Disease, Trends Cardiovasc. Med., vol. 13, pp. 116-122, (2003).
Klimaschewski, et al., Basic Fibroblast Growth Factor Isoforms Promote Axonal Elongation and Branching of Adult Sensory Neurons in Vitro, Neuroscience, vol. 126, (2004), pp. 347-353.
Koshida, et al., Synthesis and Biological Activity of Oligomer-Model Compounds Containing Units of a Key Platelet-Binding Disaccharide of Heparin. Tetrahedrom Letters, vol. 40, (1999), pp. 5725-5728.
Kovensky, et al., Binding of Heparin Sulfate to Fibroblast Growth Factor-2 Total Synthesis of a Putative Pentasaccharide Binding Site, Tetrahedron: Asymmetry, vol. 7, No. 11,pp. 3119-3128, (1996).
Laham, et al., Intracoronary Basic Fibroblast Growth Factor (FGF-2) in Patients With Sever Ischemic Heart Disease: Results of a Phase I Open-Label Dose Escalation Study, Journal of the American College of Cardiology, vol. 36, No. 7, (2000), pp. 2132-2139.
Laham et al., Local Perivascular Delivery of Basic Fibroblast Growth Factor in Patients Undergoing Coronary Bypass Surgery Results of a Phase I Randomized, Double-Blind, Placebo-Controlled Trial, Circulation, vol. 100, pp. 1865-1871, (1999).
Lahdenranta, et al., An Anti-Angiogenic State in Mice and Humans With Retinal Photoreceptor Cell Degeneration, PNAS, (2001), vol. 98, No. 18, pp 10368-10373.
Lazarous, et al., Basic Fibroblast Growth Factor in Patients With Intermittent Claudication: Results of a Phase I Trial, Journal of the American College of Cardiology, vol. 36, No. 4, (2000) pp. 1239-1244.
Neuhaus, et al., Reduced Mobility of Fibroblast Growth Factor (FGF)-Deficient Myoblasts Might Contribute to Dystrophic Changes in the Musculature of FGF2/FGF6/Mdx Triple-Mutant Mice, Mol. Cell. Biol., (2003), vol. 23, No. 17, pp. 6037-6048.
Noti, et al., Preparation and Use of Microarrays Containing Synthetic Heparin Oligosaccharides for the Rapid Analysis of Herparin-Protein Interactions, Chem. Eur. J., (2006), vol. 12, pp. 8664-8886.
Orita, et al., Highly Efficient Deacetylation by Use of the Neutral Organotin Catalyst [tBu2SnOH(Cl)]2, Chem. Eur. J., (2001), vol. 7, No. 15, pp. 3321-3327.
Paulsen, et al., Advances in Selective Chemical Syntheses of Complex Oligosaccharides, Angswandte Chemie International Edition in English, vol. 21, No. 3, pp. 155-224, (1982).
Petitou, et al., Synthesis of Heparin Fragments: A Methyl a-Pentaoside With High Affinity for Antithrombin III, Carbohydrate Research, vol. 167, (1987), pp. 67-75.

(56) References Cited

OTHER PUBLICATIONS

Post, et al., Therapeutic Angiogenesis in Cardiology Using Protein Formulations, Cardiovascular Research, vol. 49, (2001), pp. 522-531.

Sakurai, et al., The Efficient Prevascularization Induced by Fibroblast Growth Factor 2 With a Collagen-Coated Device Improves the Cell Survivla of a Bioartificial Pancreas, Pancreas, vol. 28, No. 3 (2004), pp. e70-e79.

Sapieha, et al., Fibroblast Growth Factor-2 Gene Delivery Stimulates Axon Growth by Adult Retinal Ganglion Cells After Acute Optic Nerve Injury, Molecular and Cellular Neuroscience, vol. 24, (2003), pp. 656-672.

Sherer, et al., Angiogenesis During Implantation, and Placental and Early Embryonic Development, Placenta, (2001), vol. 22, pp. 1-13.

Simons, et al., Pharmacological Treatment of Coronary Artery Disease With Recombinant Fibroblast Growth Factor-2 : Double-Blind, Randomized, Controlled Clinical Trial , Circulation, (2002), vol. 105, pp. 788-793.

Tabeur, et al., L-Iduronic Acid Derivatives as Glycosyl Donors, Carbohydrate Research, vol. 281, (1996), pp. 253-278.

Tabeur, et al., Oligosaccharides Corresponding to the Regular Sequence of Heparin: Chemical Synthesis and Interaction With FGF-2, Bioorganic & Medicinal Chemistry, vol. 7, (1999), pp. 2003-2012.

Takafuji, et al., Regeneration of Articular Cartilage Defects in the Tempromandibular Joint of Rabbits by Fibroblast Growth Factor-2: A Pilot Study, Int. J. Oral Maxiliofac. Surg., (2007), vol. 36, pp. 934-937.

Unger, et al., Effects of a Single Intracoronary Injection of Basic Fibroblast Growth Factor in Stable Angina Pectoris, The American Journal of Cardiology, vol. 85, (2000), pp. 1414-1419.

Van Belle, et al., Accelerated Endothelialization by Local Delivery of Recombinant Human Vascular Endothial Growth Factor Reduces In-Stent Intimal Formation, Biochemical and Biophysical Research Communications, vol. 235, pp. 311-316, (1997).

Van Boeckel, et al., Synthesis of a Pentasaccharide Corresponding to the Antithrombin III Binding Fragment of Heparin, J. Carbohydrate Chemistry, vol. 4, No. 3, pp. 293-321, (1985).

\* cited by examiner

FGF RECEPTOR-ACTIVATING N-SULFATE OLIGOSACCHARIDES, PREPARATION THEREOF, AND THERAPEUTIC USE THEREOF

CROSS REFERENCE TO RELATED APPLICATIONS

This application is a continuation of International Application No. PCT/FR2010/051702 filed Aug. 12, 2010, which claims priority benefit to France Application No. 0903969 filed Aug. 14, 2009, the disclosures of which are herein incorporated by reference in their entirety.

The present invention relates to N-sulfate oligosaccharides that are agonists of the FGF/FGFR system, and to their preparation and therapeutic use.

Angiogenesis is a process of generation of new blood capillaries. During the blockage of a blood vessel, angiogenesis, combined with arteriogenesis (dilation of the capillaries), improves the revascularization of the blocked area. It has been shown in vitro and in vivo that several growth factors, such as Fibroblast Growth Factors (FGFs), stimulate the neovascularization process.

FGFs are a family of 23 members. FGF2 (or basic FGF) is an 18 kDa protein. FGF2 induces, in endothelial cells in culture, their proliferation and migration and the production of proteases. in vivo, FGF2 promotes neovascularization. FGF2 interacts with endothelial cells via two classes of receptors, the high-affinity receptors with tyrosine kinase activity (FGFRs) and the low-affinity receptors of heparan sulfate proteoglycan (HSPG) type.

It is known that cell surface receptors with tyrosine kinase activity associate in dimeric form with a complex formed from two ligand molecules and one heparan sulfate molecule. The formation of this complex triggers a cascade of intracellular signals resulting in activation of cell proliferation and migration, which are two key processes involved in angiogenesis.

Thus, FGF2 and its receptors represent very pertinent targets for therapies directed towards activating or inhibiting angiogenesis processes.

Synthetic oligosaccharides have also been the subject of studies of interactions with the FGF receptors and have shown their inhibitory effects on the binding of FGF-2 to its receptor on smooth muscle cells, with an IC50 of 16 µg/mL, and also an inhibition of proliferation of these cells induced with FGF-2, with an IC50 of about 23 µg/mL (C. Tabeur et al., *Bioorg. & Med. Chem.*, 1999, 7, 2003-2012; C. Noti et al., *Chem. Eur. J.*, 2006, 12, 8664-8686).

We have now found novel synthetic oligosaccharides that are capable of facilitating the formation of the FGF/FGFR complex and of thus promoting the in vitro survival of endothelial cells and of increasing the in vitro and in vivo formation of new blood vessels.

One subject of the present invention is novel oligosaccharide compounds corresponding to formula (I):

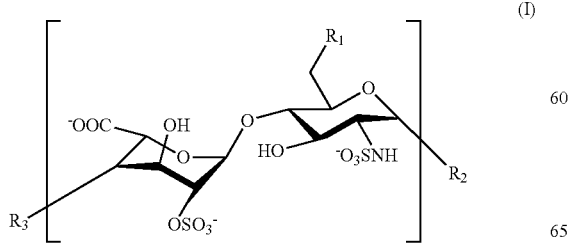

in which:

$R_1$ represents a group —$OSO_3^-$ or a hydroxyl group, $R_2$ represents either a group —O-alkyl, or a monosaccharide of formula (II), in which R represents an alkyl group:

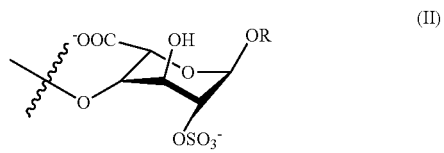

$R_3$ represents a disaccharide of formula (III):

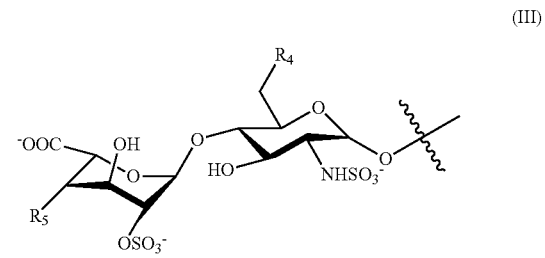

in which:

$R_4$ represents a group —$OSO_3^-$ or a hydroxyl group, $R_5$ represents a disaccharide of formula (IV):

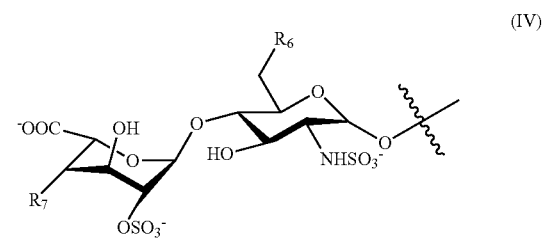

in which:

$R_6$ represents a group —$OSO_3^-$ or a hydroxyl group, $R_7$ represents either a hydroxyl group or a disaccharide of formula (VI):

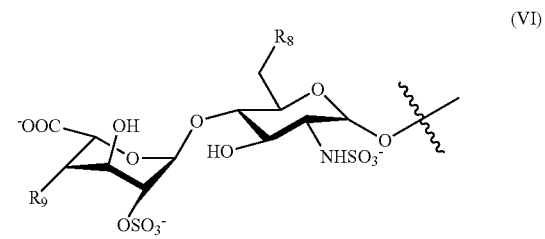

in which:

$R_8$ represents a group —$OSO_3^-$ or a hydroxyl group, $R_9$ represents either a hydroxyl group or a group —O-alkyl, or a disaccharide of formula (VII):

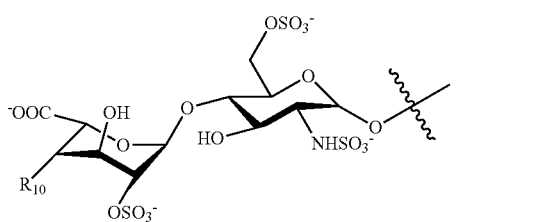

(VII)

in which $R_{10}$ represents a group —O-alkyl, on condition that: $R_9$ represents a hydroxyl group or a group —O-alkyl when $R_2$ represents a monosaccharide of formula (II) as defined above; $R_7$ represents a disaccharide of formula (VI) as defined above when $R_2$ represents a group —O-alkyl; and $R_1$, $R_4$, $R_6$ and $R_8$ do not simultaneously represent hydroxyl groups.

In the context of the present invention, and unless otherwise mentioned in the text, the term "alkyl group" is understood to mean a linear or branched saturated aliphatic group comprising 1 to 4 carbon atoms. Examples that may be mentioned include methyl, ethyl, propyl, isopropyl, butyl, isobutyl and tert-butyl groups. In the compounds according to the invention, including each of the subgroups of compounds that will be defined hereinbelow, the alkyl groups advantageously represent methyl groups, except for the substituents $R_9$ and $R_{10}$ in which the alkyl radicals of the groups —O-alkyl advantageously represent propyl groups.

The compounds according to the invention are synthetic oligosaccharides, i.e. they are compounds obtained by total synthesis starting from intermediate synthons, as will be described in detail in the text hereinbelow. In this respect, they differ from oligosaccharides obtained by depolymerization or isolation from complex mixtures of polysaccharides, such as heparins or low molecular weight heparins. In particular, the compounds according to the invention have a well-defined structure resulting from their chemical synthesis and are in the form of pure oligosaccharides, i.e. they are free of other oligosaccharide species.

The invention encompasses the compounds of formula (I) in acid form or in the form of any pharmaceutically acceptable salt thereof. In the acid form, the functions —COO⁻ and —SO₃⁻ are, respectively, in —COOH and —SO₃H form.

The term "pharmaceutically acceptable salt of the compounds of the invention" means a compound in which one or more of the functions —COO⁻ and/or —SO₃⁻ are ionically linked to a pharmaceutically acceptable cation. The preferred salts according to the invention are those in which the cation is chosen from alkali metal cations, especially the Na⁺ cation.

The compounds of formula (I) according to the invention also comprise those in which one or more hydrogen or carbon atoms have been replaced with a radioactive isotope, for example tritium or carbon $^{14}$C. Such labelled compounds are useful in research, metabolism or pharmacokinetic studies, as ligands in biochemical tests.

In formula (I) of the compounds according to the present invention, it is understood that:

the monosaccharide of formula (II) is linked to the disaccharide unit represented in formula (I) via the oxygen atom located in position 4 of its uronic acid unit, the disaccharide of formula (III) is linked to the disaccharide unit represented in formula (I) via the oxygen atom located in position 1 of its glucosamine unit, similarly, the disaccharide of formula (IV) is linked to the disaccharide of formula (III) via the oxygen atom located in position 1 of its glucosamine unit, similarly, the disaccharide of formula (VI) is linked to the disaccharide of formula (IV) via the oxygen atom located in position 1 of its glucosamine unit, similarly, the disaccharide of formula (VII) is linked to the disaccharide of formula (VI) via the oxygen atom located in position 1 of its glucosamine unit.

The term "glucosamine unit" means the monosaccharide unit having the following formula:

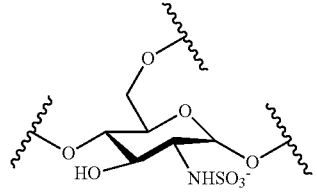

The other type of saccharide unit present in the compounds according to the invention is a uronic acid, more specifically an iduronic acid, corresponding to the following formula:

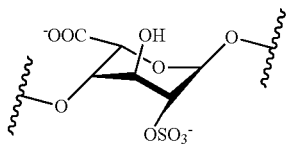

Thus, the compounds of formula (I) according to the invention may also be represented according to formula (I') as follows, in which the iduronic units and the glucosamine units succeed each other and in which $R_1$, $R_2$, $R_4$, $R_6$ and $R_7$ are as defined previously:

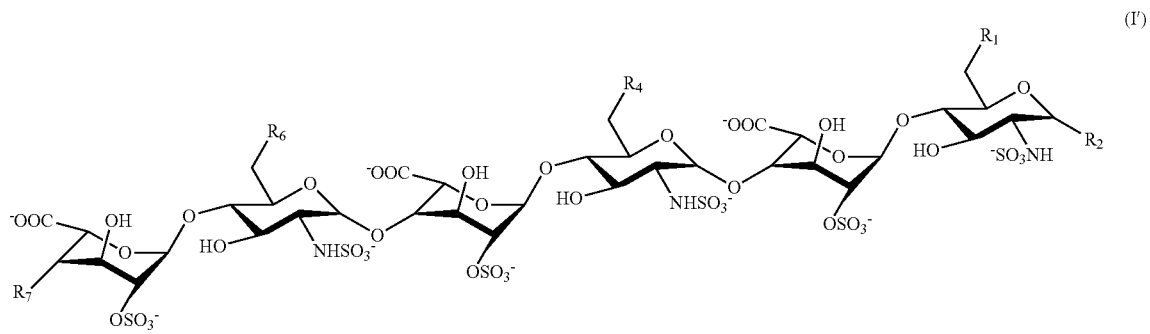

(I')

Depending on the meanings of $R_2$ and $R_7$, the oligosaccharides according to the invention may thus comprise from 7 to 10 saccharide units.

Among the compounds of formula (I)/(I') that are subjects of the invention, mention may be made of those in which:
- $R_1$, $R_3$, $R_4$, $R_5$ and $R_6$ are as defined previously,
- $R_2$ represents a monosaccharide of formula (II) as defined previously, and
- $R_7$ represents a hydroxyl group.

Such compounds are heptasaccharides. They correspond to formula (I-1) below, in which $R_7$ represents a hydroxyl group and R, $R_1$, $R_4$ and $R_6$ are as defined previously, and are in acid form or in the form of any pharmaceutically acceptable salt thereof.

Among the compounds of formula (I)/(I') that are subjects of the invention, mention may be made of a subgroup of compounds in which $R_2$ represents a group —O-alkyl.

Such compounds are octasaccharides or decasaccharides. They correspond to formula (I-2) below in which $R_1$, $R_4$, $R_6$, $R_8$ and $R_9$ are as defined previously and $R_2$ represents a group —O-alkyl, and are in acid form or in the form of any pharmaceutically acceptable salt thereof.

Among the compounds of formula (I)/(I') that are subjects of the invention, mention may be made of a subgroup of compounds in which:
- $R_2$ represents a group —O-alkyl, and
- $R_7$ represents a disaccharide of formula (VI) as defined above, in which $R_9$ represents a disaccharide of formula (VII) as defined above.

Such compounds are decasaccharides. They correspond to formula (I-3) below, in which $R_1$, $R_4$, $R_6$, $R_8$ and $R_{10}$ are as defined previously, and are in acid form or in the form of any pharmaceutically acceptable salt thereof.

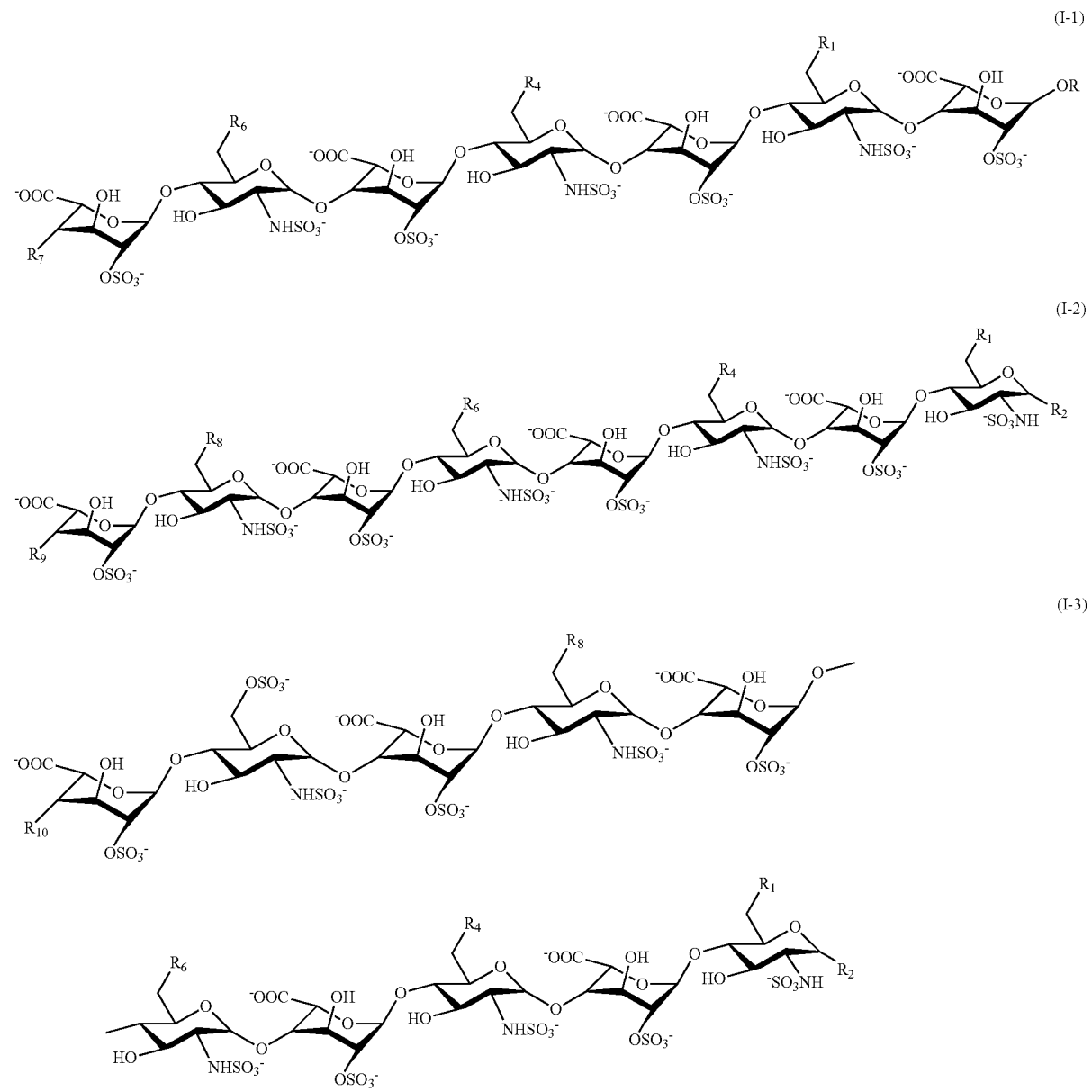

Among the compounds of formula (I) that are subjects of the invention, mention may be made of a subgroup of compounds in which:
  $R_2$ represents a group —O-alkyl, and
  $R_7$ represents a disaccharide of formula (VI) as defined above, in which $R_9$ represents either a hydroxyl group or a group —O-alkyl.

Such compounds are octasaccharides and correspond to formula (I-2) above in which $R_1$, $R_4$, $R_6$ and $R_8$ are as defined previously, $R_2$ represents a group —O-alkyl and $R_9$ represents either a hydroxyl group or a group —O-alkyl.

Advantageously, the octasaccharides according to the invention are such that $R_9$ represents a group —O-alkyl.

Other subgroups of compounds according to the invention may have several of the characteristics listed above for each of the subgroups defined previously.

The invention relates especially to the following oligosaccharides:

methyl(sodium 4-O-propyl-2-O-sodium sulfonato-α-L-idopyranosyluronate)-(1→4)-(2-deoxy-6-O-sodium sulfonato-2-sodium (sulfonatoamino)-α-D-glucopyranosyl)-(1→4)-[(sodium 2-O-sodium sulfonato-α-L-idopyranosyluronate)-(1→4)-(2-deoxy-6-O-sodium sulfonato-2-sodium (sulfonatoamino)-α-D-glucopyranosyl-(1→4)]$_2$-(sodium 2-O-sodium sulfonato-α-L-idopyranosyluronate)-(1→4)-2-deoxy-6-O-sodium sulfonato-2-sodium (sulfonatoamino)-α-D-glucopyranoside (No. 1);

methyl(sodium 4-O-propyl-2-O-sodium sulfonato-α-L-idopyranosyluronate)-(1→4)-(2-deoxy-6-O-sodium sulfonato-2-sodium (sulfonatoamino)-α-D-glucopyranosyl)-(1→4)-[(sodium 2-O-sodium sulfonato-α-L-idopyranosyluronate)-(1→4)-(2-deoxy-6-O-sodium sulfonato-2-sodium (sulfonatoamino)-α-D-glucopyranosyl-(1→4)]$_3$-(sodium 2-O-sodium sulfonato-α-L-idopyranosyluronate)-(1→4)-2-deoxy-6-O-sodium sulfonato-2-sodium (sulfonatoamino)-α-D-glucopyranoside (No. 2);

sodium [methyl(sodium 2-O-sodium sulfonato-α-L-idopyranosyluronate)-(1→4)-(2-deoxy-6-O-sodium sulfonato-2-sodium (sulfonatoamino)-α-D-glucopyranosyl)-(1→4)-[sodium 2-O-sodium sulfonato-α-L-idopyranosyluronate)-(1→4)-(2-deoxy-6-O-sodium sulfonato-2-sodium (sulfonatoamino)-α-D-glucopyranosyl)-(1→4)]$_2$-2-O-sodium sulfonato-α-L-idopyranoside]-uronate (No. 3);

methyl(sodium 2-O-sodium sulfonato-α-L-idopyranosyluronate)-(1→4)-(2-deoxy-2-sodium (sulfonatoamino)-α-D-glucopyranosyl)-(1→4)-(sodium 2-O-sodium sulfonato-α-L-idopyranosyluronate)-(1→4)-(2-deoxy-2-sodium (sulfonatoamino)-α-D-glucopyranosyl)-(1→4)-(sodium 2-O-sodium sulfonato-α-L-idopyranosyluronate)-(1→4)-(2-deoxy-6-O-sodium sulfonato-2-sodium (sulfonatoamino)-α-D-glucopyranosyl)-(1→4)-(sodium 2-O-sodium sulfonato-α-L-idopyranosyluronate)-(1→4)-2-deoxy-6-O-sodium sulfonato-2-sodium (sulfonatoamino)-α-D-glucopyranoside (No. 4);

methyl(sodium 2-O-sodium sulfonato-α-L-idopyranosyluronate)-(1→4)-(2-deoxy-2-sodium (sulfonatoamino)-α-D-glucopyranosyl)-(1→4)-(sodium 2-O-sodium sulfonato-α-L-idopyranosyluronate)-(1→4)-(2-deoxy-6-O-sodium sulfonato-2-sodium (sulfonatoamino)-α-D-glucopyranosyl)-(1→4)-(sodium 2-O-sodium sulfonato-α-L-idopyranosyluronate)-(1→4)-(2-deoxy-2-sodium (sulfonatoamino)-α-D-glucopyranosyl)-(1→4)-(sodium 2-O-sodium sulfonato-α-L-idopyranosyluronate)-(1→4)-2-deoxy-6-O-sodium sulfonato-2-sodium (sulfonatoamino)-α-D-glucopyranoside (No. 5);

methyl(sodium 2-O-sodium sulfonato-α-L-idopyranosyluronate)-(1→4)-(2-deoxy-6-O-sodium sulfonato-2-sodium (sulfonatoamino)-α-D-glucopyranosyl)-(1→4)-(sodium 2-O-sodium sulfonato-α-L-idopyranosyluronate)-(1→4)-(2-deoxy-2-sodium (sulfonatoamino)-α-D-glucopyranosyl)-(1→4)-(sodium 2-O-sodium sulfonato-α-L-idopyranosyluronate)-(1→4)-(2-deoxy-2-sodium (sulfonatoamino)-α-D-glucopyranosyl)-(1→4)-(sodium 2-O-sodium sulfonato-α-L-idopyranosyluronate)-(1→4)-2-deoxy-6-O-sodium sulfonato-2-sodium (sulfonatoamino)-α-D-glucopyranoside (No. 6);

methyl(sodium 2-O-sodium sulfonato-α-L-idopyranosyluronate)-(1→4)-(2-deoxy-6-O-sodium sulfonato-2-sodium (sulfonatoamino)-α-D-glucopyranosyl)-(1→4)-(sodium 2-O-sodium sulfonato-α-L-idopyranosyluronate)-(1→4)-(2-deoxy-2-sodium (sulfonatoamino)-α-D-glucopyranosyl)-(1→4)-(sodium 2-O-sodium sulfonato-α-L-idopyranosyluronate)-(1→4)-(2-deoxy-6-O-sodium sulfonato-2-sodium (sulfonatoamino)-α-D-glucopyranosyl)-(1→4)-(sodium 2-O-sodium sulfonato-α-L-idopyranosyluronate)-(1→4)-2-deoxy-6-O-sodium sulfonato-2-sodium (sulfonatoamino)-α-D-glucopyranoside (No. 7);

methyl(sodium 2-O-sodium sulfonato-α-L-idopyranosyluronate)-(1→4)-(2-deoxy-6-O-sodium sulfonato-2-sodium (sulfonatoamino)-α-D-glucopyranosyl)-[(1→4)-(sodium 2-O-sodium sulfonato-α-L-idopyranosyluronate)-(1→4)-(2-deoxy-6-O-sodium sulfonato-2-sodium (sulfonatoamino)-α-D-glucopyranosyl)]$_2$-(1→4)-(sodium 2-O-sodium sulfonato-α-L-idopyranosyluronate)-(1→4)-2-deoxy-6-O-sodium sulfonato-2-(sulfonato)amino-α-D-glucopyranoside (No. 8);

methyl(sodium 2-O-sodium sulfonato-α-L-idopyranosyluronate)-(1→4)-(2-deoxy-6-O-sodium sulfonato-2-sodium (sulfonato)amino-α-D-glucopyranosyl)-[(1→4)-(sodium 2-O-sodium sulfonato-α-L-idopyranosyluronate)-(1→4)-(2-deoxy-6-O-sodium sulfonato-2-sodium (sulfonatoamino)-α-D-glucopyranosyl)]$_2$-(1→4)-(sodium 2-O-sodium sulfonato-α-L-idopyranosyluronate)-(1→4)-2-deoxy-2-sodium (sulfonatoamino)-α-D-glucopyranoside (No. 9).

In its principle, the process for preparing the compounds according to the invention uses di- or oligosaccharide synthons prepared as reported previously in the literature. Reference will be made especially to the patents or patent applications EP 0 300 099, EP 0 529 715, EP 0 621 282 and EP 0 649 854, and also to the publication by C. Van Boeckel and M. Petitou published in *Angew. Chem. Int. Ed. Engl.*, 1993, 32, 1671-1690. These synthons are then coupled together so as to give an entirely protected equivalent of a compound according to the invention. This protected equivalent is then converted into a compound according to the invention. In the coupling reactions mentioned above, a "donor" di- or oligosaccharide, activated on its anomeric carbon, reacts with an "acceptor" di- or oligosaccharide, bearing a free hydroxyl.

The present invention thus relates to a process for preparing compounds of formula (I)/(I'), characterized in that:
  in a first phase, a fully protected equivalent of the desired compound (I) is synthesized,
  in a second phase, the groups —COO$^-$ and —OSO$_3^-$ are introduced and/or unmasked,
  in a third phase, the whole compound is deprotected, and
  in a fourth phase, the N-sulfate groups are introduced.

The synthesis of the fully protected equivalent of the desired compound (I) is performed according to reactions that are well known to those skilled in the art, and using methods for the synthesis of oligosaccharides (for example G. J. Boons, *Tetrahedron* (1996), 52, 1095-1121 and patent applications WO 98/03554 and WO 99/36443), in which a glycoside bond-donating oligosaccharide is coupled with a glycoside bond-accepting oligosaccharide to give another oligosaccharide whose size is equal to the sum of the sizes of the two reactive species. This sequence is repeated until the compound of formula (I)/(I') is obtained, optionally in protected form. The nature and profile of the charge of the final desired compound determine the nature of the chemical species used in the various synthetic steps, according to the rules well known to those skilled in the art. Reference may be made, for example, to C. Van Boeckel and M. Petitou, *Angew. Chem. Int. Ed. Engl.* (1993), 32, 1671-1690 or alternatively to H. Paulsen, "Advances in selective chemical syntheses of complex oligosaccharides", *Angew. Chem. Int. Ed. Engl.* (1982), 21, 155-173.

The compounds of the invention may naturally be prepared using various strategies known to those skilled in the art of oligosaccharide synthesis. The process described above is the preferred process of the invention. However, the compounds of formula (I)/(I') may be prepared via other well-known methods of sugar chemistry, described, for example, in "Monosaccharides, their chemistry and their roles in natural products", P. M. Collins and R. J. Ferrier, J. Wiley & Sons (1995) and by G. J. Boons in *Tetrahedron* (1996), 52, 1095-1121.

The protecting groups used in the process for preparing the compounds of formula (I)/(I') are those that make it possible firstly to protect a reactive function such as a hydroxyl or an amine during a synthesis, and secondly to regenerate the intact reactive function at the end of the synthesis. The protecting groups commonly used in sugar chemistry, as described, for example, in "Protective Groups in Organic Synthesis", Greene et al., 3rd edition (John Wiley & Sons, Inc., New York) are used to perform the process according to the invention. The protecting groups are chosen, for example, from acetyl, halomethyl, benzoyl, levulinyl, benzyl, allyl, tert-butyldiphenylsilyl (tBDPS) groups.

Activating groups may also be used; these are the groups conventionally used in sugar chemistry, for example according to G. J. Boons, *Tetrahedron* (1996), 52, 1095-1121. These activating groups are chosen, for example, from imidates and thioglycosides.

The process described above allows the compounds of the invention to be obtained in the form of salts, advantageously in the form of the sodium salt. To obtain the corresponding acids, the compounds of the invention in salt form may be placed in contact with a cation-exchange resin in acidic form. The compounds of the invention in acid form may then be neutralized with a base to obtain the desired salt. For the preparation of the salts of the compounds of formula (I)/(I'), any mineral or organic base that gives pharmaceutically acceptable salts with the compounds of formula (I)/(I') may be used.

A subject of the invention is also the compounds of formula 20A below, in which Pg, Pg' and Pg", which may be identical or different, represent protecting groups:

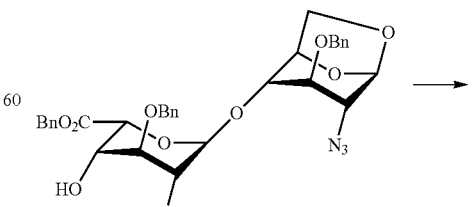

Such compounds are useful as intermediates in the synthesis of the compounds of formula (I)/(I').

In particular, a subject of the invention is the compounds 20A in which Pg, Pg' and Pg" represent, respectively, benzyl, allyl and acetyl groups. Such a compound corresponds to disaccharide 20 illustrated in scheme 2 below, useful for the synthesis of compounds 1 and 2 according to the invention, as will be detailed hereinbelow:

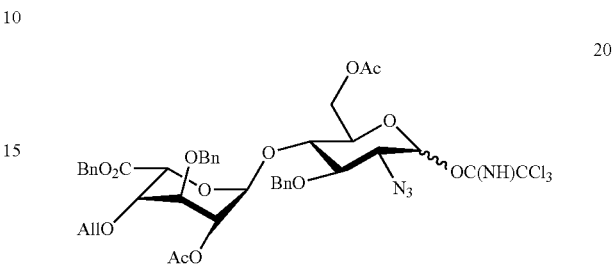

The examples that follow describe the preparation of certain compounds and synthetic intermediates in accordance with the invention. These compounds are not limiting, but serve merely to illustrate the present invention. The starting compounds and the reagents, when their mode of preparation is not expressly described, are commercially available or described in the literature, or else may be prepared according to methods that are described therein or that are known to those skilled in the art.

The following abbreviations are used:
[α]$_D$: optical rotation
Ac: acetyl
All: allyl
Bn: benzyl
Bz: benzoyl
TLC: thin-layer chromatography
CrO$_3$: chromium trioxide
DDQ: 2,3-dichloro-5,6-dicyano-1,4-benzoquinone
ESI: Electron-Spray Ionization
h: hours
H$_2$SO$_4$: sulfuric acid
Lev: levulinyl
Me: methyl
min: minutes
Rf: Retardation factor (retention time measured on TLC relative to the solvent migration front)
tBDPS: tert-butyldiphenylsilyl
Z: benzyloxycarbonyl Preparation of the Synthetic Intermediates SCHEME 1: Preparation of the donor disaccharide 15

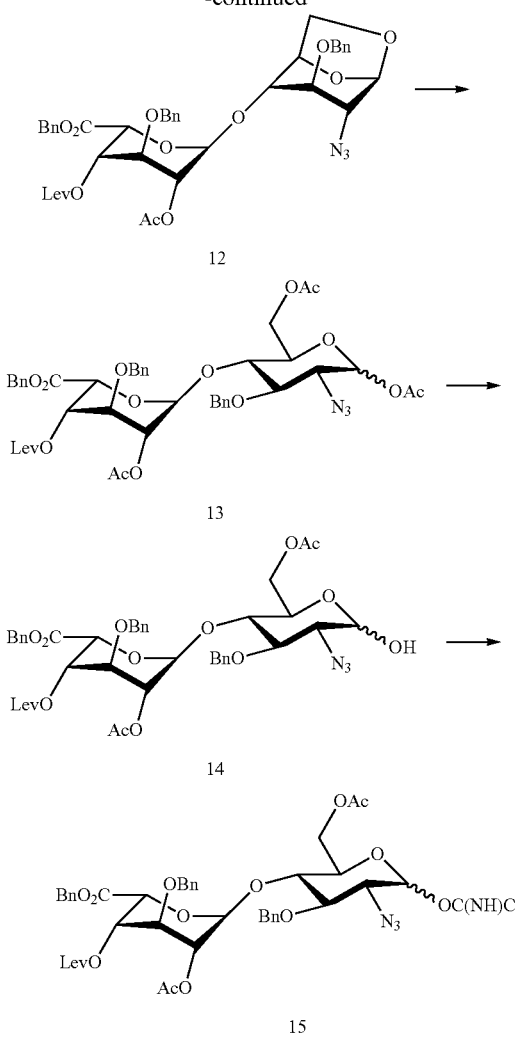

(Benzyl 2-O-acetyl-3-O-benzyl-4-O-levulinoyl-α-L-idopyranosyluronate)-(1→4)-1,6-di-O-acetyl-2-azido-3-O-benzyl-2-deoxy-α,β-D-glucopyranose (13)

To a solution of compound 12 (12.76 g, 16.2 mmol) in acetic anhydride (160 mL) is added, at 0° C., trifluoroacetic acid (14.1 mL, 183 mmol). The reaction medium is stirred for 16 hours at room temperature. After concentrating, the mixture is co-evaporated with toluene. Purification of the residue by chromatography on a column of silica gel (4/1 v/v toluene/acetone) gives 10.5 g of compound 13.

TLC: Rf=0.49, silica gel, (4/1 v/v toluene/acetone)

(Benzyl 2-O-acetyl-3-O-benzyl-4-O-levulinoyl-α-L-idopyranosyluronate)-(1→4)-6-O-acetyl-2-azido-3-O-benzyl-2-deoxy-α,β-D-glucopyranose (1→4)

A solution of compound 13 (10.5 g, 12.0 mmol) and benzylamine (50 mL, 457 mmol) in diethyl ether (360 mL) is stirred at room temperature for 2 hours. The reaction mixture is diluted with diethyl ether (2000 mL). The organic phase is washed with cold aqueous 1 M hydrochloric acid solution and then with water, dried over sodium sulfate, filtered and then concentrated to dryness. The residue is chromatographed on a column of silica gel (3/1 v/v toluene/acetone) to give 7.14 g of compound 14.

TLC: Rf=0.40, silica gel, 3/1 v/v toluene/acetone (Benzyl 2-O-acetyl-3-O-benzyl-4-O-levulinoyl-α-L-idopyranosyluronate)-(1→4)-6-O-acetyl-2-azido-3-O-benzyl-2-deoxy-α,β-D-glucopyranose trichloroacetimidate (15)

Trichloroacetonitrile (4.3 mL, 42.8 mmol) and cesium carbonate (1.89 g, 13.7 mmol) are added to a solution of compound 14 (7.14 g, 8.56 mmol) in dichloromethane (160 mL). After stirring for 30 minutes, the reaction medium is filtered and then concentrated. The residue is purified by chromatography on a column of silica gel (2/1 v/v toluene/acetone+0.1% triethylamine) to give 7.0 g of compound 15.

TLC: Rf=0.37 and 0.28, silica gel, 2/1 v/v toluene/acetone (Benzyl 2-O-acetyl-3-O-benzyl-4-O-levulinoyl-α-L-idopyranosyluronate)-(1→4)-1,6-anhydro-2-azido-3-O-benzyl-2-deoxy-β-D-glucopyranose (12)

To a solution of compound 11 (11.6 g, 16.2 mmol) (described in the preparation of compound 8 of patent application WO 2006/021653) in anhydrous dioxane (340 mL) are successively added 4-dimethylaminopyridine (2.12 g, 17.3 mmol), 1-(3-dimethylaminopropyl)-3-ethylcarbodiimide hydrochloride (6.5 g, 34.3 mmol) and levulinic acid (3.6 mL; 34.3 mmol). After stirring for 4 hours 30 minutes, the mixture is diluted with dichloromethane (1800 mL). The organic phase is washed successively with aqueous 10% potassium hydrogen sulfate solution, with saturated sodium chloride solution, with saturated aqueous sodium hydrogen carbonate solution and then with water, dried over sodium sulfate, filtered and then evaporated to dryness. The residue is purified by chromatography on a column of silica gel (5/1 v/v toluene/acetone) to give 12.7 g of compound 12.

TLC: Rf=0.42, silica gel, 3/1 v/v toluene/acetone

SCHEME 2: Preparation of the glycosyl donor 20

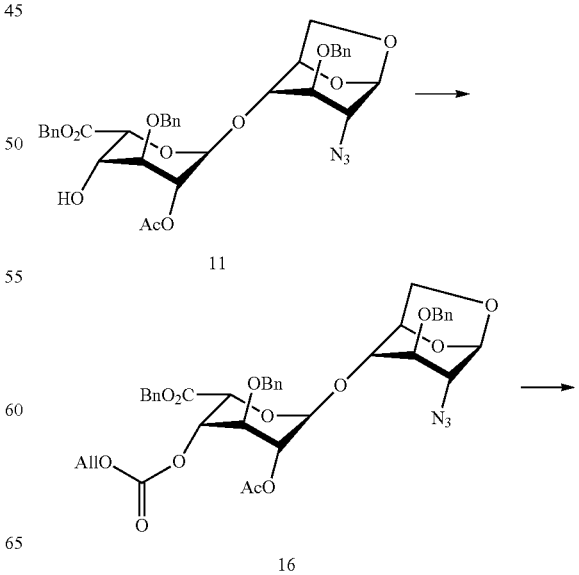

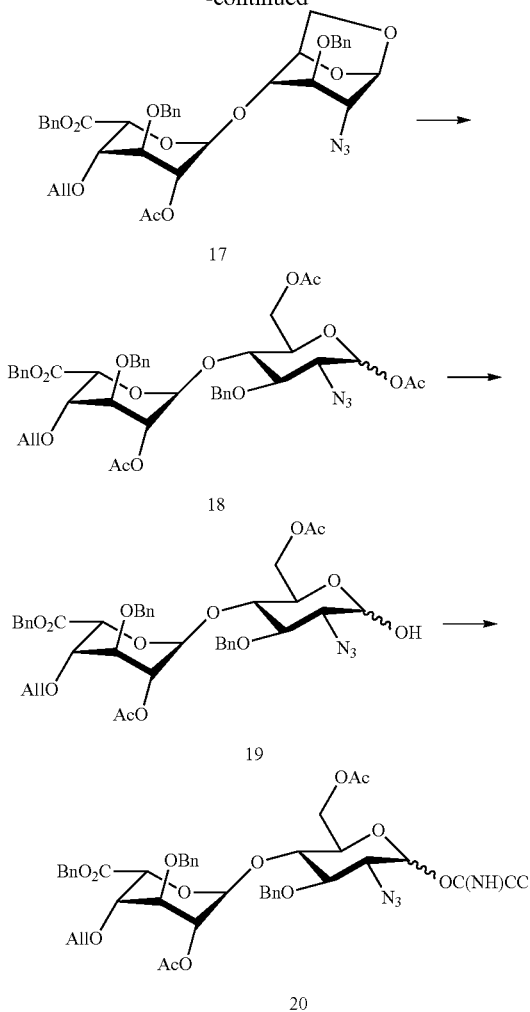

(Benzyl 2-O-acetyl-4-O-(allyloxy)carbonyl-3-O-benzyl-α-L-idopyranosyluronate)-(1→4)-1,6-anhydro-2-azido-3-O-benzyl-2-deoxy-β-D-glucopyranose (16)

To a solution of compound 11 (11.7 g, 17.3 mmol) (described in the preparation of compound 8 of patent application WO 2006/021653) in anhydrous tetrahydrofuran are successively added, at 0° C., pyridine (14 mL; 173 mmol), 4-dimethylaminopyridine (2.12 g, 17.3 mmol) and allyl chloroformate (18.3 mL, 173 mmol). After stirring for 16 hours at room temperature, water (47 mL) is added at 0° C. After stirring for 30 minutes, the mixture is diluted with ethyl acetate (800 mL). The organic phase is washed successively with aqueous 10% potassium hydrogen sulfate solution and water and then with saturated aqueous sodium hydrogen carbonate solution and water, dried over sodium sulfate, filtered and then evaporated to dryness. The residue is purified by chromatography on a column of silica gel (2/1 v/v cyclohexane/ethyl acetate) to give 11.4 g of compound 16.

TLC: Rf=0.37, silica gel, 2/1 v/v cyclohexane/ethyl acetate.

(Benzyl 2-O-acetyl-4-O-allyl-3-O-benzyl-α-L-idopyranosyluronate)-(1→4)-1,6-anhydro-2-azido-3-O-benzyl-2-deoxy-β-D-glucopyranose (17)

Compound 16 (11.44 g, 15.1 mmol) is dissolved in tetrahydrofuran (100 mL). Palladium acetate (67.6 mg, 0.30 mmol) and triphenylphosphine (395 mg, 1.5 mmol) are added. After stirring for 2 hours at reflux, the reaction medium is concentrated to dryness. The residue is purified by chromatography on a column of silica gel (3/1 v/v cyclohexane/ethyl acetate) to give 8.0 g of compound 17.

TLC: Rf=0.33, silica gel, 2/1 v/v cyclohexane/ethyl acetate.

(Benzyl 2-O-acetyl-4-O-allyl-3-O-benzyl-α-L-idopyranosyluronate)-(1→4)-1,6-di-O-acetyl-2-azido-3-O-benzyl-2-deoxy-α,β-D-glucopyranose (18)

To a solution of compound 16 (7.96 g, 11.1 mmol) in acetic anhydride (105 mL) cooled to 0° C. is added trifluoroacetic acid (9.4 mL). The reaction medium is stirred for 16 hours at room temperature. After concentrating, the mixture is coevaporated with toluene (5×200 mL). Purification of the residue by chromatography on a column of silica gel (2/1 v/v cyclohexane/ethyl acetate) gives 7.72 g of compound 18.

TLC: Rf=0.40, silica gel, 2/1 v/v cyclohexane/ethyl acetate (Benzyl 2-O-acetyl-4-O-allyl-3-O-benzyl-α-L-idopyranosyluronate)-(1→4)-6-O-acetyl-2-azido-3-O-benzyl-2-deoxy-α,β-D-glucopyranose (19)

A solution of compound 18 (7.72 g, 9.44 mmol) and benzylamine (3.9 mL, 35.2 mmol) in diethyl ether (280 mL) is stirred at room temperature for 6 hours. The reaction mixture is diluted with diethyl ether (800 mL). The organic phase is washed with aqueous 1 M hydrochloric acid solution and then with water, dried over sodium sulfate, filtered and then concentrated to dryness. The residue is purified by chromatography on a column of silica gel (5/2 v/v toluene/ethyl acetate) to give 6.14 g of compound 19.

TLC: Rf=0.45, silica gel, 5/3 v/v toluene/ethyl acetate (Benzyl 2-O-acetyl-4-O-allyl-3-O-benzyl-α-L-idopyranosyluronate)-(1→4)-6-O-acetyl-2-azido-3-O-benzyl-2-deoxy-α,β-D-glucopyranose trichloroacetimidate (20)

Trichloroacetonitrile (4 mL, 39.6 mmol) and cesium carbonate (4.13 g, 12.7 mmol) are added to a solution of compound 19 (6.14 g, 7.9 mmol) in dichloromethane (150 mL). After stirring for 30 minutes, the reaction medium is filtered and then concentrated. The residue is purified by chromatography on a column of silica gel (4/1 v/v toluene/ethyl acetate) to give 6.5 g of compound 20.

TLC: Rf=0.50, silica gel, 3/1 v/v toluene/ethyl acetate

Chemical shifts of the anomeric protons (500 MHz, CDCl$_3$) δ 5.27 IdoUA$^{II}$, 5.57 Glc$^I$β and 5.28 IdoUA$^{II}$, 6.36 Glc$^I$α

LC-MS m/z 798.2 [(M+Na)$^+$]. $T_{R1}$=13.59 min and $T_{R2}$=13.75 min

SCHEME 3: Preparation of the octasaccharide 26
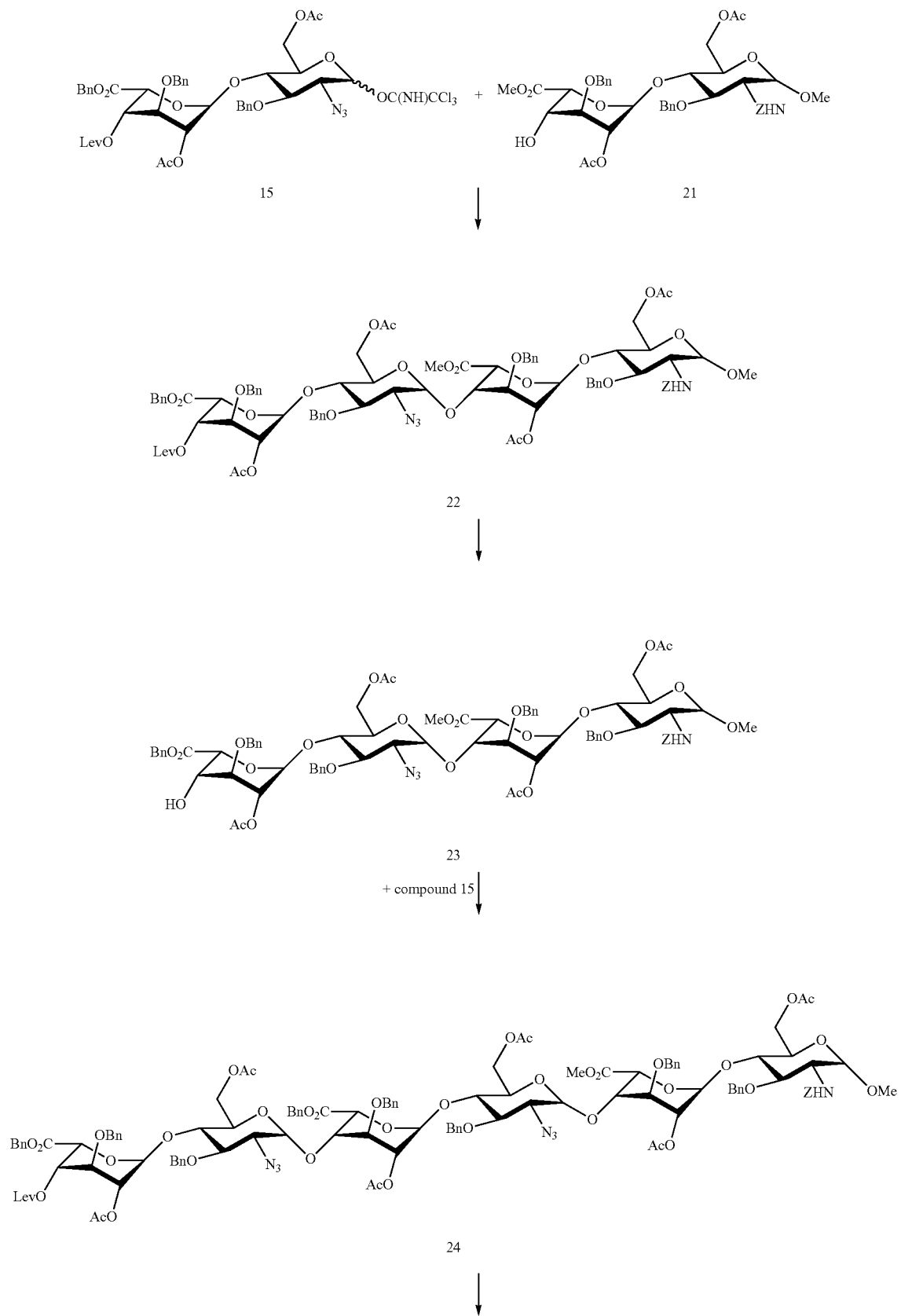

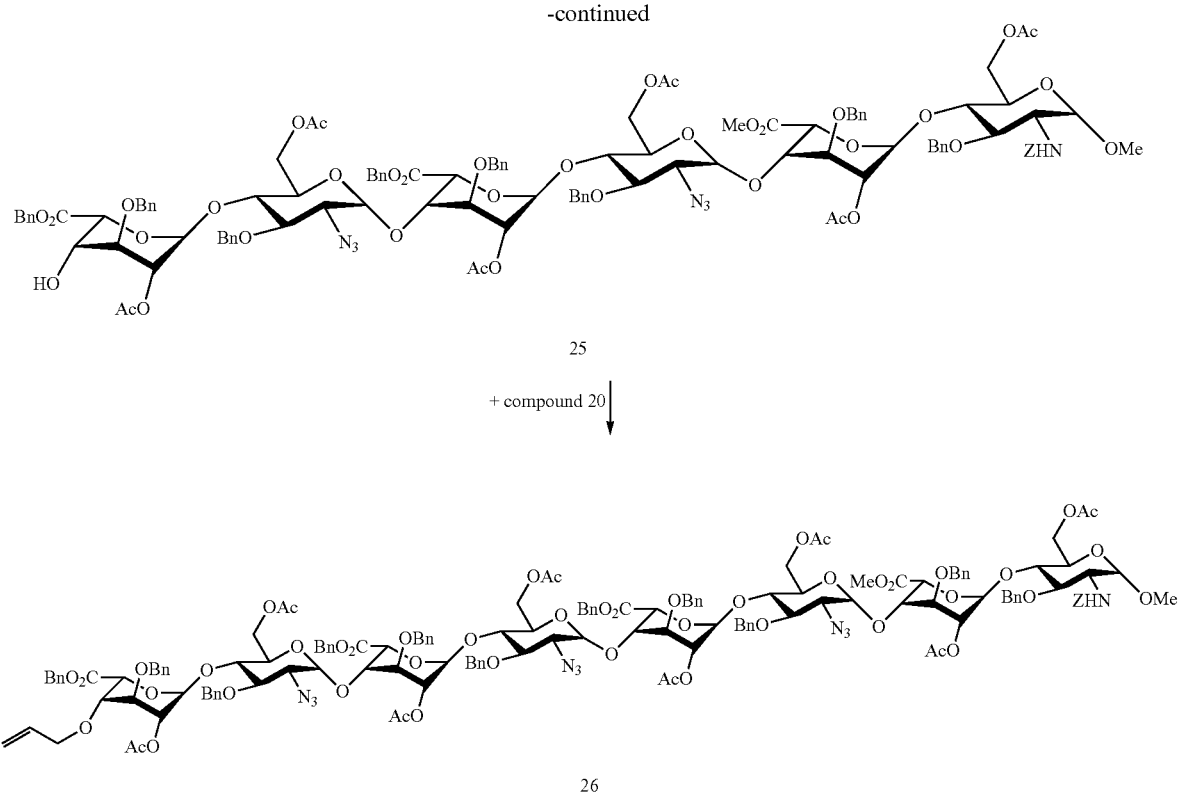

Methyl(benzyl 2-O-acetyl-3-O-benzyl-4-O-levulinoyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-6-O-acetyl-3-O-benzyl-2-{f[(benzyloxy)carbonyl]amino}-2-deoxy-α-D-glucopyranoside (22)

A mixture of the imidate 15 (541 mg, 0.553 mmol), the glycosyl acceptor 21 (650 mg, 0.83 mmol) (prepared according to the method described in *Carbohydrate Research* (1987), 167 67-75) and powdered 4 Å molecular sieves (412 mg) in a toluene/dichloromethane mixture (23 mL, 20/3 v/v) is stirred under an argon atmosphere for 1 hour at 25° C. The reaction mixture is cooled to −25° C. and a 1 M solution of tert-butyldimethylsilyl triflate in dichloromethane (82.5 μL) is added to the reaction medium. After 15 minutes, the reaction medium is neutralized by addition of solid sodium hydrogen carbonate. After filtering and concentrating, the residue obtained is purified by size exclusion chromatography (Sephadex® LH20, 120×3 cm, 1/1 v/v dichloromethane/ethanol) to give 746 mg of compound 22.

TLC: Rf=0.37, silica gel, 5/6 v/v cyclohexane/ethyl acetate.

Methyl(benzyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-6-O-acetyl-3-O-benzyl-2-{[(benzyloxy)carbonyl]amino}-2-deoxy-α-D-glucopyranoside (23)

To a solution of compound 22 (2.3 g, 1.44 mmol) in a 1/2 v/v toluene/ethanol mixture (290 mL) is added hydrazine acetate (662.3 mg, 7.2 mmol). The reaction medium is stirred for 2 hours at room temperature. After concentrating, the residue is purified by flash chromatography on a column of silica gel (5/6 v/v cyclohexane/ethyl acetate) to give 1.84 g of compound 23.

TLC: Rf=0.48, silica gel, 5/6 v/v cyclohexane/ethyl acetate.

Methyl(benzyl 2-O-acetyl-3-O-benzyl-4-O-levulinoyl-α-L-idopyranosyluronate)-(1→4)-(6-O-acetyl-2-azido-3-O-benzyl-2-deoxy-α-D-glucopyranosyl)-(1→4)-(benzyl 2-O-acetyl-3-O-benzyl-α-L-idopyranosyluronate)-(1→4)-(6-O-acetyl-2-azido-3-O-benzyl-2-deoxy-α-D-glucopyranosyl-(1→4)-(methyl 2-O-acetyl-3-O-benzyl-α-L-idopyranosyluronate)-(1→4)-6-O-acetyl-3-O-benzyl-2-{[(benzyloxy)carbonyl]amino}-2-deoxy-α-D-glucopyranoside (24)

A mixture of the glycosyl acceptor 23 (1.97 g, 1.12 mmol), the imidate 15 (1.63 g, 1.66 mmol) and powdered 4 Å molecular sieves (2.6 g) in a 1/1 v/v dichloromethane/toluene mixture (75 mL) is stirred under an argon atmosphere for 1 hour at 25° C. The reaction mixture is cooled to −20° C. and a 1 M solution of tert-butyldimethylsilyl triflate in dichloromethane (250 μL) is added to the reaction medium. After 10 minutes, the reaction medium is neutralized by addition of solid sodium hydrogen carbonate. After filtering and concentrating, the residue obtained is purified by size exclusion chromatography (Sephadex® LH20, 190× 3.2 cm, 1/1 v/v dichloromethane/ethanol) to give 1.63 g of compound 24.

TLC: Rf=0.33, silica gel, 3/1 v/v toluene/acetone.

Methyl(benzyl 2-O-acetyl-3-O-benzyl-α-L-idopyra-
nosyluronate)-(1→4)-(6-O-acetyl-2-azido-3-O-ben-
zyl-2-deoxy-α-D-glucopyranosyl)-(1→4)-(benzyl
2-O-acetyl-3-O-benzyl-α-L-idopyranosyluronate)-
(1→4)-(6-O-acetyl-2-azido-3-O-benzyl-2-deoxy-α-
D-glucopyranosyl)-(1→4)-(methyl 2-O-acetyl-3-O-
benzyl-α-L-idopyranosyluronate)-(1→4)-6-O-acetyl-
3-O-benzyl-2-{[(benzyloxy)carbonyl]amino}-2-
deoxy-α-D-glucopyranoside (25)

To a solution of compound 24 (1.7 g, 0.73 mmol) in a 1/2 v/v toluene/ethanol mixture (145 mL) is added hydrazine acetate (338 mg, 3.67 mmol). The reaction medium is stirred for 2 hours at room temperature. After concentrating, the residue is purified by flash chromatography on a column of silica gel (1/1 v/v cyclohexane/ethyl acetate) to give compound 25 (1.41 g).

TLC: Rf=0.47, silica gel, 1/1 v/v cyclohexane/ethyl acetate.

Methyl(benzyl 2-O-acetyl-4-O-allyl-3-O-benzyl-
α-L-idopyranosyluronate)-(1→4)-(6-O-acetyl-2-
azido-3-O-benzyl-2-deoxy-α-D-glucopyranosyl)-
(1→4)-[(benzyl 2-O-acetyl-3-O-benzyl-α-L-idopyra-
nosyluronate)-(1→4)-(6-O-acetyl-2-azido-3-O-
benzyl-2-deoxy-α-D-glucopyranosyl-(1→4)]₂-
(methyl 2-O-acetyl-3-O-benzyl-α-L-
idopyranosyluronate)-(1→4)-6-O-acetyl-3-O-
benzyl-2-{[(benzyloxy)carbonyl]amino}-2-deoxy-α-
D-glucopyranoside (26)

A mixture of the imidate 20 (0.681 mg, 0.74 mmol), the glycosyl acceptor 25 (1.10 g, 0.5 mmol), and powdered 4 Å molecular sieves (0.555 g) in a 1/1 v/v dichloromethane/toluene mixture (26 mL) is stirred under an argon atmosphere for 1 hour at 25° C. The reaction mixture is cooled to −20° C. and a 1 M solution of tert-butyldimethylsilyl triflate in dichloromethane (111 μL) is added. After 20 minutes, the reaction medium is neutralized by addition of solid sodium hydrogen carbonate. After filtering through Celite® and concentrating, the residue obtained is chromatographed on a size exclusion column (Sephadex® LH20, 190×3.2 cm, 1/1 v/v dichloromethane/ethanol) to give successively 468 mg of octasaccharide 26 and 842 mg of a mixture containing the hexasaccharide 25 and the octasaccharide 26.

This mixture (842 mg) is treated under the above conditions to give compound 26 (513.6 mg) after treatment and column chromatography (Sephadex® LH20, 190×3.2 cm, 1/1 v/v dichloromethane/ethanol).

The two fractions (468 mg and 513.6 mg) are combined and purified by preparative HPLC chromatography on a column of silica gel (2/1 v/v toluene/ethyl acetate) to give compound 26 (1.03 g).

TLC: Rf=0.44, silica gel, 2/1 v/v toluene/ethyl acetate.

SCHEME 4: Preparation of the octasaccharide 30

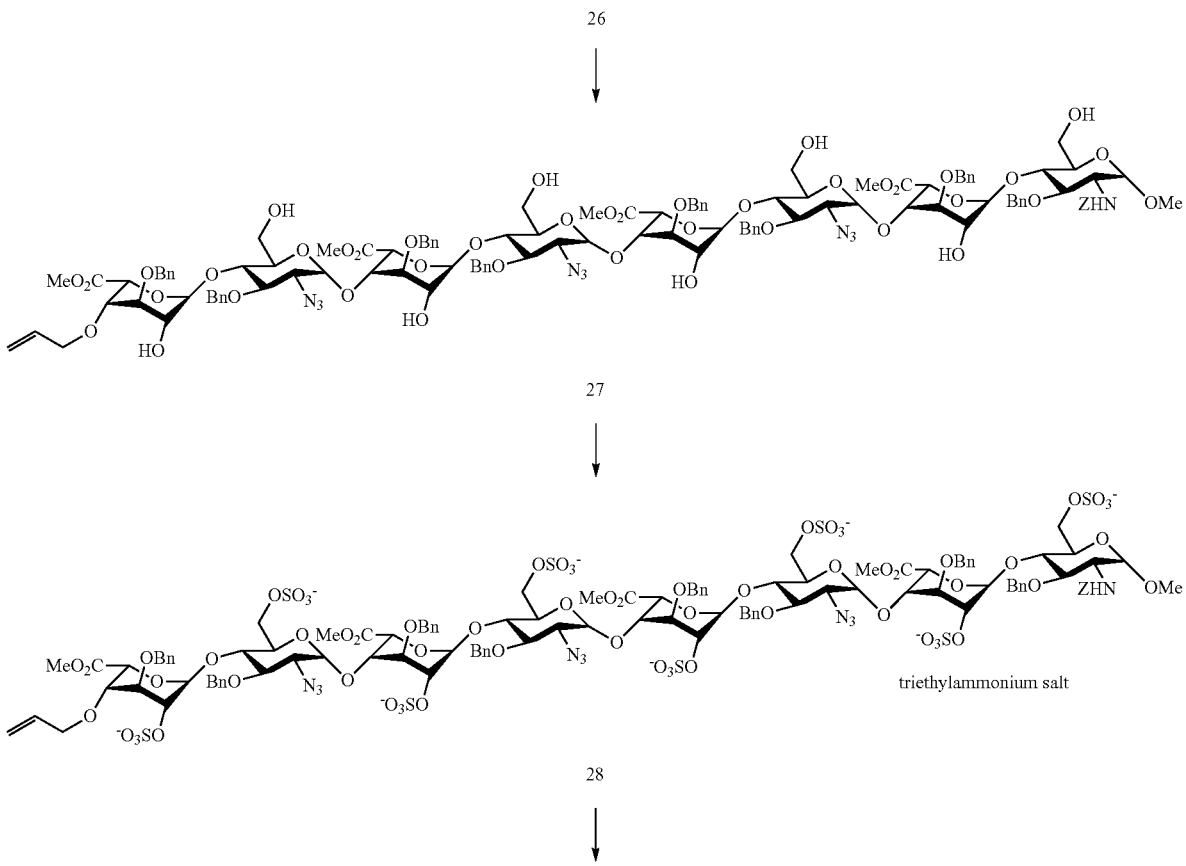

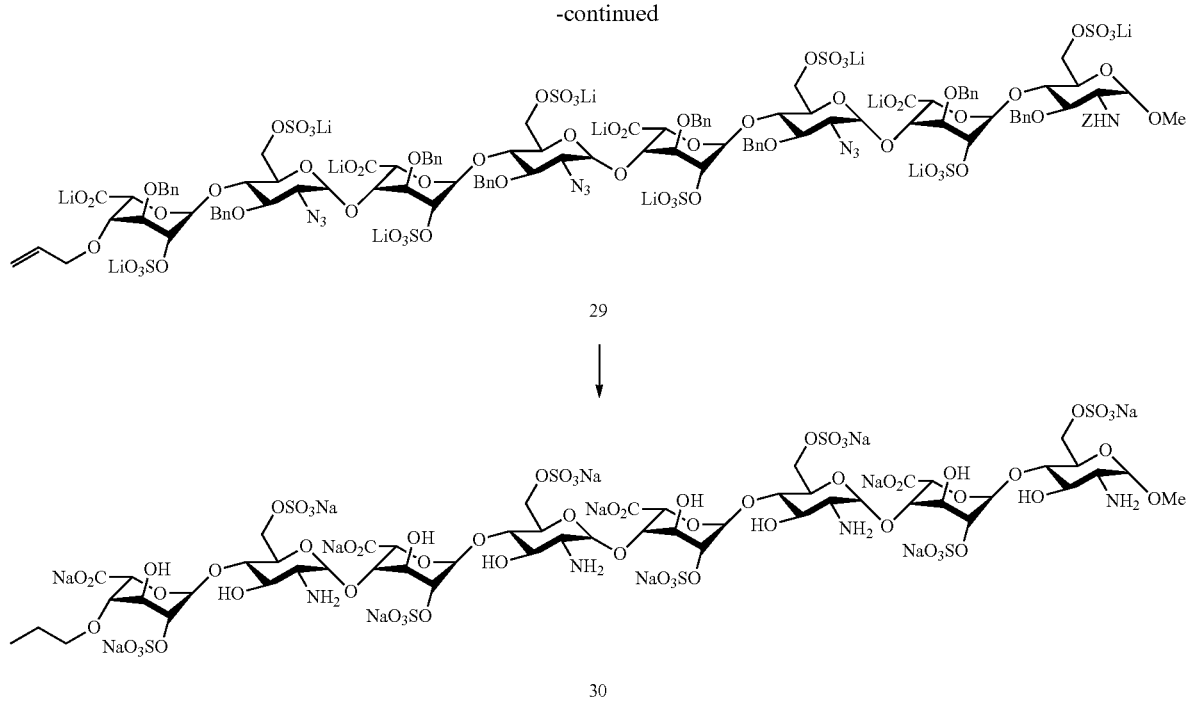

Methyl(methyl 4-O-allyl-3-O-benzyl-α-L-idopyranosyluronate)-(1→4)-(2-azido-3-O-benzyl-2-deoxy-α-D-glucopyranosyl)-(1→4)-[(methyl 3-O-benzyl-α-L-idopyranosyluronate)-(1→4)-(2-azido-3-O-benzyl-2-deoxy-α-D-glucopyranosyl-(1→4)]$_2$-(methyl 3-O-benzyl-α-L-idopyranosyluronate)-(1→4)-3-O-benzyl-2-{[(benzyloxy)carbonyl]amino}-2-deoxy-α-D-glucopyranoside (27)

To a solution of compound 26 (819 mg, 0.27 mmol) in a 2/3 v/v dichloromethane/methanol mixture (83 mL) containing 3 Å molecular sieves (10.3 g) is added, at 0° C., under an argon atmosphere a 1 M solution of sodium methoxide in methanol (1.65 mL). After 16 hours at −18° C., the reaction medium is neutralized with Dowex® 50 W×4 H$^+$ resin. After filtering and concentrating, the residue is purified by size exclusion chromatography (Sephadex® LH20, 120×3 cm, 1/1 v/v dichloromethane/ethanol) followed by chromatography on a column of silica gel (4/3 v/v toluene/acetone) to give 605 mg of compound 27.

TLC: Rf=0.41, silica gel, 4/3 v/v toluene/acetone.

Methyl(methyl 4-O-allyl-3-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-[(methyl 3-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl-(1→4)]$_2$-(methyl 3-O-benzyl-2-O-triethylammonium sulfonato-α-L-idopyranosyluronate)-(1→4)-3-O-benzyl-2-{[(benzyloxy)carbonyl]amino}-2-deoxy-6-O-triethylammonium sulfonato-α-D-glucopyranoside (28)

Compound 27 (300 mg, 0.12 mmol) is dried by co-distillation of N,N-dimethylformamide (3×10 mL) and is then dissolved in N,N-dimethylformamide (11 mL). To this solution is added the sulfur trioxide-triethylamine complex (902 mg; 4.98 mmol). The mixture is stirred for 16 hours at 55° C. protected from light and then neutralized with methanol (202 μL, 4.98 mmol). The reaction medium is deposited on a column of Sephadex® LH20 gel (95×2 cm) eluted with a 1/1 v/v dichloromethane/ethanol mixture to give compound 28 (426 mg).

TLC: Rf=0.32, silica gel, 11/7/1.6/4 v/v/v/v ethyl acetate/pyridine/acetic acid/water.

Methyl(lithium 4-O-allyl-3-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-[(lithium 3-O-benzyl-2-O-lithium sulfonato-α-L-idopyranosyluronate)-(1→4)-(2-azido-3-O-benzyl-2-deoxy-6-O-lithium sulfonato-α-D-glucopyranosyl-(1→4)]$_2$-(lithium 3-O-benzyl-2-O-lithium sulfonato-α-L-idopyranosyluronate)-(1→4)-3-O-benzyl-2-{[(benzyloxy)carbonyl]amino}-2-deoxy-6-O-lithium sulfonato-α-D-glucopyranoside (29)

To a solution of compound 28 (459 mg, 0.12 mmol) in a 1/1 v/v tetrahydrofuran/methanol mixture (19 mL) is added, at 0° C., a 0.7 M solution of lithium hydroxide in water (7.6 mL; qs final concentration of 0.2 M). After 1 hour at 0° C. and then 16 hours at room temperature, the reaction medium is cooled to 0° C., neutralized with acetic acid (305 μL) and then deposited on a Sephadex® LH20 column (95×2 cm) eluted with a 4/1 v/v methanol/water mixture to give compound 29 (368 mg).

TLC: Rf=0.25, silica gel, 27/19/4.2/11 v/v/v/v ethyl acetate/pyridine/acetic acid/water.

Methyl(sodium 4-O-npropyl-2-O-sodium sulfonato-α-L-idopyranosyluronate)-(1→4)-(2-amino-2-deoxy-6-O-sodium sulfonato-α-D-glucopyranosyl)-(1→4)-[sodium 2-O-sodium sulfonato-α-L-idopyranosyluronate)-(1→4)-(2-amino-2-deoxy-6-O-sodium sulfonato-α-D-glucopyranosyl-(1→4)]₂-(sodium 2-O-sulfonato-α-L-idopyranosyluronate)-(1→4)-2-amino-2-deoxy-6-O-sodium sulfonato-α-D-glucopyranoside (30)

A solution of compound 29 (170 mg) in a 2/3 v/v tert-butanol/water mixture (27 mL) is treated under pressure of hydrogen (1 bar) in the presence of 10% palladium-on-charcoal (340 mg) at 30° C. for 24 hours. After filtration (Millipore® LSWP 5 μm filter), the reaction mixture is deposited on a column of Sephadex® G25-fine (90×3 cm) eluted with aqueous 0.2 M sodium chloride solution. The fractions containing the product are concentrated and desalified using the same column eluted with water. After concentrating to dryness, compound 30 (205 mg) is obtained.

Mass: "ESI" method, negative mode: theoretical mass=2327.55; experimental mass: 2239 a.m.u. (iduronic acids observed in COOH form).

SCHEME 5: Preparation of the decasaccharide 33

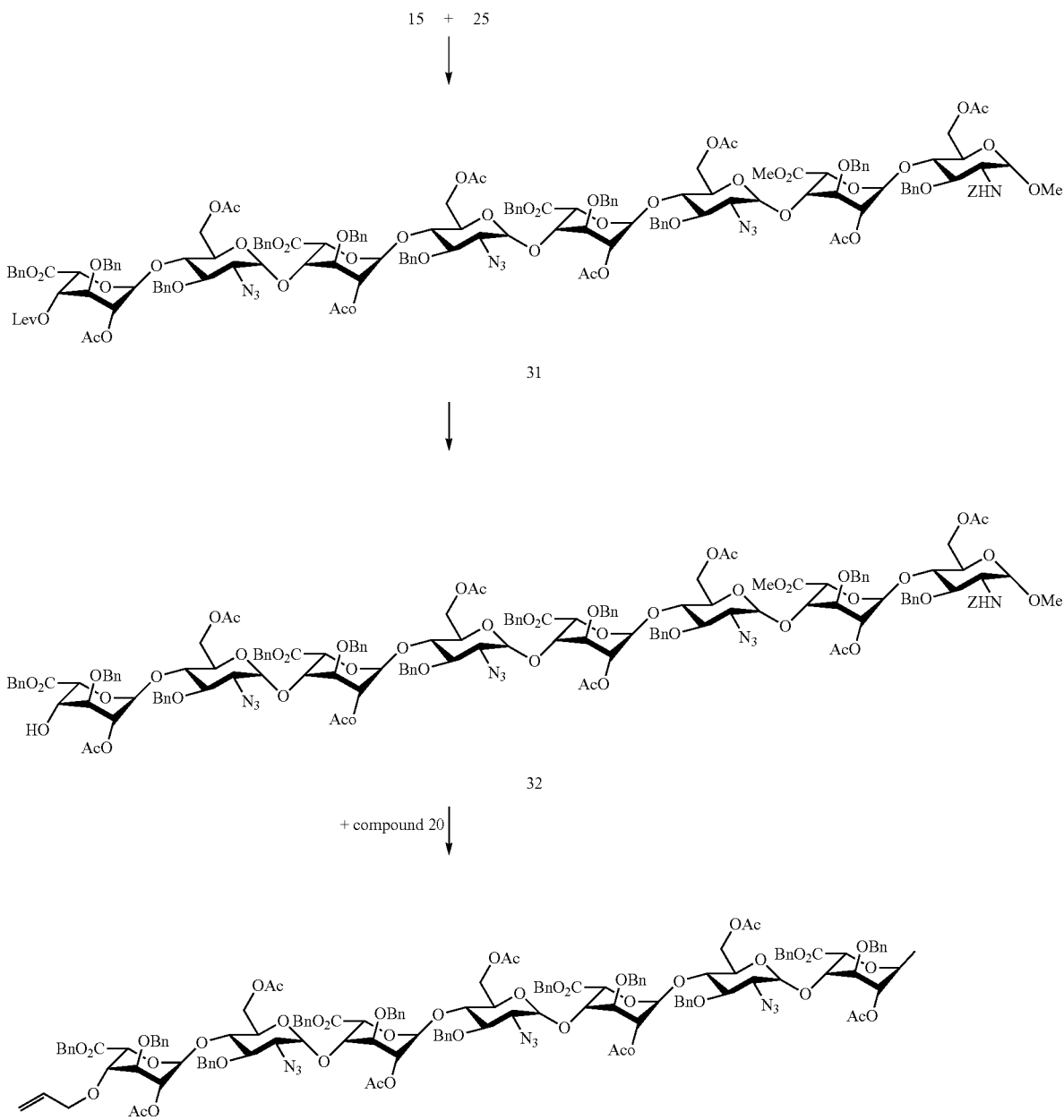

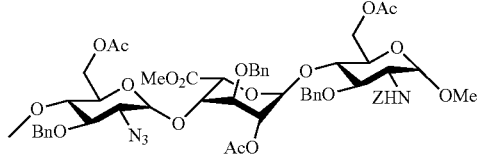

33

Methyl(benzyl 2-O-acetyl-3-O-benzyl-4-O-levulinoyl-α-L-idopyranosyluronate)-(1→4)-(6-O-acetyl-2-azido-3-O-benzyl-2-deoxy-α-D-glucopyranosyl)-(1→4)-[(benzyl 2-O-acetyl-3-O-benzyl-α-L-idopyranosyluronate)-(1→4)-(6-O-acetyl-2-azido-3-O-benzyl-2-deoxy-α-D-glucopyranos-(1→4)]$_2$-(methyl 2-O-acetyl-3-O-benzyl-α-L-idopyranosyluronate)-(1→4)-6-O-acetyl-3-O-benzyl-2-{[(benzyloxy)carbonyl]amino}-2-deoxy-α-D-glucopyranoside (31)

A mixture of the imidate 15 (250 mg, 0.255 mmol), the glycosyl acceptor 25 (376 mg, 0.169 mmol) and powdered 4 Å molecular sieves (396 mg) in a 1/1 v/v dichloromethane/toluene mixture (11.4 mL) is stirred under an argon atmosphere for 1 hour at 25° C. The reaction mixture is cooled to −20° C. and a 0.1 M solution of tert-butyldimethylsilyl triflate in dichloromethane (381 μL) is added. After 12 minutes, the reaction medium is neutralized by addition of solid sodium hydrogen carbonate. After filtering and concentrating, the residue obtained is chromatographed on a Sephadex® LH20 column (120×3 cm, 1/1 v/v dichloromethane/ethanol) to give successively 150 mg of crude compound 31 and 318 mg of a mixture containing the hexasaccharide 25 and the octasaccharide 31.

The mixture containing the hexasaccharide 25 and the octasaccharide 33 is treated under the above conditions to give after size exclusion chromatography (Sephadex® LH20) 151 mg of crude compound 31 and 191 mg of a mixture containing the hexasaccharide 25 and the octasaccharide 31. This operation is repeated twice to the point of depletion of the hexasaccharide 25.

The fractions containing the crude octasaccharide 31 are combined and purified by flash chromatography on a column of silica gel (7/3 v/v toluene/ethyl acetate) to give compound 31 (351 mg).

TLC: Rf=0.37, silica gel, 7/5 v/v toluene/ethyl acetate.

Methyl(benzyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-[(benzyl 2-O-acetyl-3-O-benzyl-α-L-idopyranosyluronate)-(1→4)-(6-O-acetyl-2-azido-3-O-benzyl-2-deoxy-α-D-glucopyranosyl-(1→4)]$_2$-(methyl 2-O-acetyl-3-O-benzyl-α-L-idopyranosyluronate)-(1→4)-6-O-acetyl-3-O-benzyl-2-{[(benzyloxy)carbonyl]amino}-2-deoxy-α-D-glucopyranoside (32)

To a solution of compound 31 (335 mg, 0.11 mmol) in a 1/2 v/v toluene/ethanol mixture (22 mL) is added hydrazine acetate (51 mg, 0.55 mmol). The reaction medium is stirred for 2 hours at room temperature. The reaction mixture is diluted with dichloromethane (50 mL). The organic phase is washed with aqueous 2% potassium hydrogen sulfate solution, and then with water, dried over sodium sulfate, filtered and then concentrated to dryness. The residue is purified by chromatography on a column of silica gel (7/3 v/v toluene/acetone) to give compound 32 (238 mg).

TLC: Rf=0.50, silica gel, 5/6 v/v cyclohexane/ethyl acetate.

Methyl(benzyl 2-O-acetyl-4-O-allyl-3-O-benzyl-α-L-idopyranosyluronate)-(1→4)-(6-O-acetyl-2-azido-3-O-benzyl-2-deoxy-α-D-glucopyranosyl)-(1→4)-[(benzyl 2-O-acetyl-3-O-benzyl-α-L-idopyranosyluronate)-(1→4)-(6-O-acetyl-2-azido-3-O-benzyl-2-deoxy-α-D-glucopyranosyl-(1→4)]$_3$-(methyl 2-O-acetyl-3-O-benzyl-α-L-idopyranosyluronate)-(1→4)-6-O-acetyl-3-O-benzyl-2-{[(benzyloxy)carbonyl]amino}-2-deoxy-α-D-glucopyranoside (33)

A mixture of the imidate 20 (64 mg, 0.066 mmol), the glycosyl acceptor 32 (130 mg, 0.044 mmol) and powdered 4 Å molecular sieves (49 mg) in a 1/1 v/v dichloromethane/toluene mixture (2.2 mL) is stirred under an argon atmosphere for 1 hour at 25° C. The reaction mixture is cooled to −20° C. and a 0.1 M solution of tert-butyldimethylsilyl triflate in dichloromethane (100 μL) is added. After 10 minutes, the reaction medium is neutralized by addition of solid sodium hydrogen carbonate. After filtering and concentrating, the residue obtained is chromatographed on a Sephadex® LH20 column (120×3 cm, 1/1 v/v dichloromethane/ethanol) to give successively 61 mg of crude compound 33 and 87.7 mg of a mixture containing the octasaccharide 32 and the decasaccharide 33.

The above mixture (87.7 mg) is treated under the above conditions to give crude compound 33 (120 mg) after chromatography on a Sephadex® LH20 column (120×3 cm, 1/1 v/v dichloromethane/ethanol).

The two fractions containing the crude compound are combined and purified by flash chromatography on a column of silica gel (7/2 v/v toluene/ethyl acetate) to give compound 33 (120 mg).

TLC: Rf=0.52, silica gel, 1/1 v/v cyclohexane/ethyl acetate

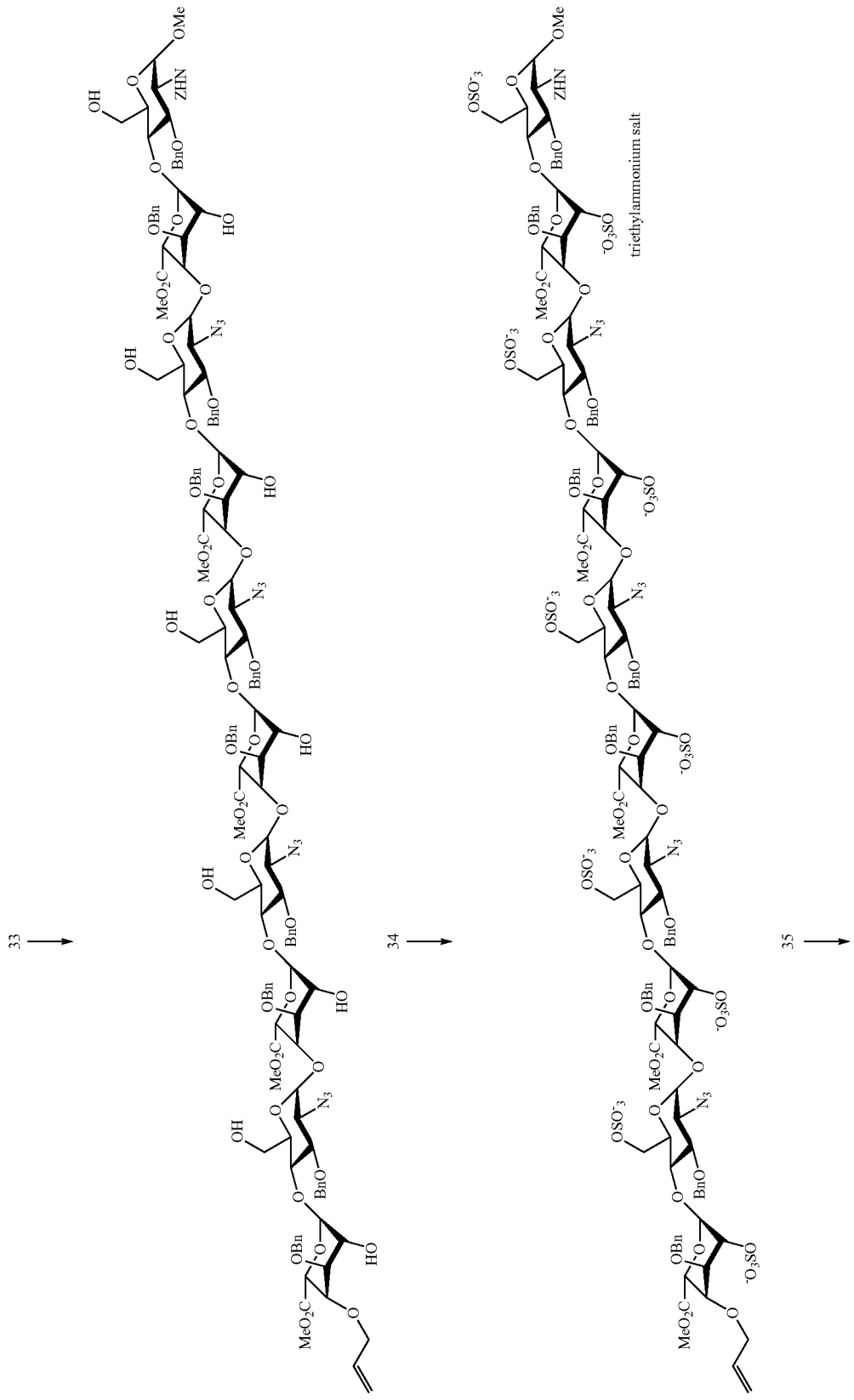
SCHEME 6: Preparation of the decasaccharide 37

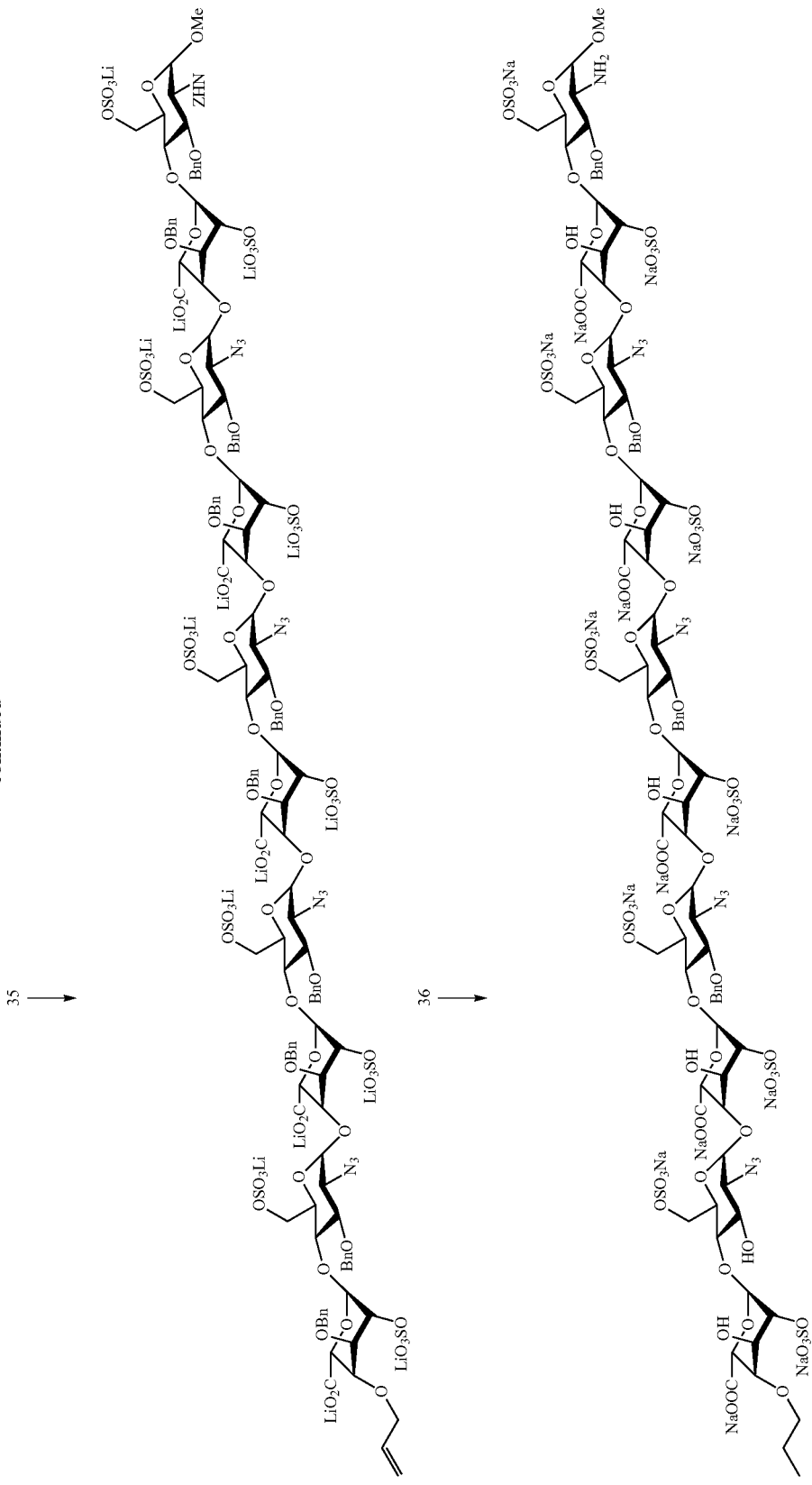

Methyl(methyl 4-O-allyl-3-O-benzyl-α-L-idopyrano-
syluronate)-(1→4)-(2-azido-3-O-benzyl-2-deoxy-
α-D-glucopyranosyl)-(1→4)-[(methyl 3-O-benzyl-
α-L-idopyranosyluronate)-(1→4)-(2-azido-3-O-ben-
zyl-2-deoxy-α-D-glucopyranosyl-(1→4)]₃-O-benzyl-
α-L-idopyranosyl)-(1→4)-3-O-benzyl-2-{[(benzy-
loxy)carbonyl]amino}-2-deoxy-α-D-glucopyranoside
(34)

To a solution, cooled to 0° C., of compound 33 (51.8 mg, 0.014 mmol) in a 2/3 v/v dichloromethane/methanol mixture (982 µL) containing 3 Å molecular sieves (125 mg) is added under an argon atmosphere a 1 M solution of sodium methoxide in methanol (21.0 µL). After 5 hours at room temperature, the reaction medium is neutralized with Dowex® 50 W×4 H⁺ resin. After filtering and concentrating, the residue is purified by size exclusion chromatography (Sephadex® LH20, 95×2 cm, 1/1 v/v dichloromethane/ethanol) to give compound 34 (31.4 mg).

TLC: Rf=0.47, silica gel, 7/3 v/v dichloromethane/acetone

Methyl(methyl 4-O-allyl-3-O-benzyl-2-O-triethyl-
ammonium sulfonato-α-L-idopyranosyluronate)-
(1→4)-(2-azido-3-O-benzyl-2-deoxy-6-O-triethyl-
ammonium sulfonato-α-D-glucopyranosyl)-(1→4)-
[(methyl 3-O-benzyl-2-O-triethylammonium
sulfonato-α-L-idopyranosyluronate)-(1→4)-(2-azido-
3-O-benzyl-2-deoxy-6-O-triethylammonium sul-
fonato-α-D-glucopyranos)-(1→4)]₃-(methyl 3-O-
benzyl-2-O-triethylammonium sulfonato-α-L-
idopyranosyluronate)-(1→4)-3-O-benzyl-2-
{[(benzyloxy)carbonyl]amino}-2-deoxy-6-O-trieth-
ylammonium sulfonato-α-D-glucopyranoside (35)

Compound 34 (31.5 mg, 10.6 µmol) is treated as in the preparation of compound 28 to give compound 35 (47.0 mg) after size exclusion chromatography (Sephadex® LH20, 100×1.2 cm, 1/1 v/v dichloromethane/methanol).

TLC: Rf=0.55, silica gel, 16/11/2.6/7 v/v/v/v ethyl acetate/pyridine/acetic acid/water.

Methyl(lithium 4-O-allyl-3-O-benzyl-2-O-lithium
sulfonato-α-L-idopyranosyluronate)-(1→4)-(2-azido-
3-O-benzyl-2-deoxy-6-O-lithium sulfonato-α-D-
glucopyranosyl)-(1→4)-[(lithium 3-O-benzyl-2-O-
lithium sulfonato-α-L-idopyranosyluronate)-(1→4)-
(2-azido-3-O-benzyl-2-deoxy-6-O-lithium sulfonato-
α-D-glucopyranosyl-(1→4)]₃-(lithium 3-O-benzyl-2-
O-lithium sulfonato-α-L-idopyranosyluronate)-
(1→4)-3-O-benzyl-2-{[(benzyloxy)carbonyl]
amino}-2-deoxy-6-O-lithium sulfonato-α-D-
glucopyranoside (36)

To a solution of compound 35 (47 mg, 12.5 µmol) in a 1/1 v/v tetrahydrofuran/methanol mixture (2.0 mL) is added, at 0° C., a 1 M solution of lithium hydroxide in water (500 µL; qs a final concentration of 0.2 M). After 1 hour at 0° C. and then 4 hours at room temperature, the reaction medium is neutralized with acetic acid and then left at −20° C. for 16 hours. The reaction mixture is deposited on a column of Sephadex® LH20 gel eluted with a 4/1 v/v methanol/water mixture to give compound 36 (38.9 mg).

Methyl(sodium 4-O-propyl-2-O-sodium sulfonato-
α-L-idopyranosyluronate)-(1→4)-(2-amino-2-deoxy-
6-O-sodium sulfonato-α-D-glucopyranosyl)-(1→4)-
[sodium 2-O-sodium sulfonato-α-L-
idopyranosyluronate)-(1→4)-(2-amino-2-deoxy-6-
O-sodium sulfonato-α-D-glucopyranosyl-(1→4)]₃-
(sodium 2-O-sodium sulfonato-α-L-
idopyranosyluronate)-(1→4)-2-amino-2-deoxy-6-O-
sodium sulfonato-α-D-glucopyranoside (37)

A solution of compound 36 (40 mg, 10.8 µmol) in a 6/9 v/v tert-butanol/water mixture (1 mL) is treated under pressure of hydrogen (11 bar) in the presence of 10% palladium-on-charcoal (80 mg, 2×amount of compound to be reduced) at 40° C. for 4 hours. After filtration (Millipore® LSWP 5 µm filter), the solution is deposited on a column of Chelex® 100 resin (1 mL) eluted with water and then concentrated to dryness. The crude compound thus obtained (27 mg) is used without further purification in the following step.

Mass: "ESI" method, negative mode: theoretical mass=2781.10; experimental mass: 2782.05±0.30 a.m.u.

SCHEME 7: Preparation of the heptasaccharide 43

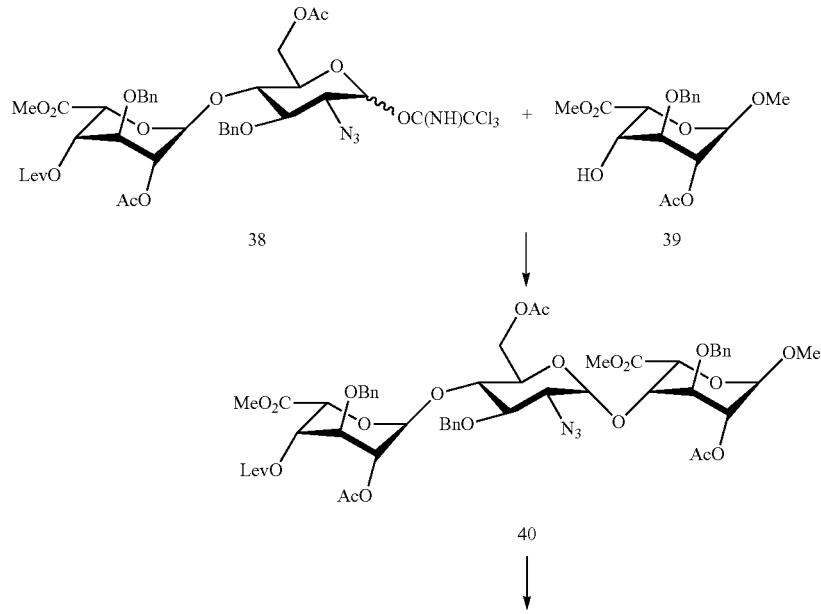

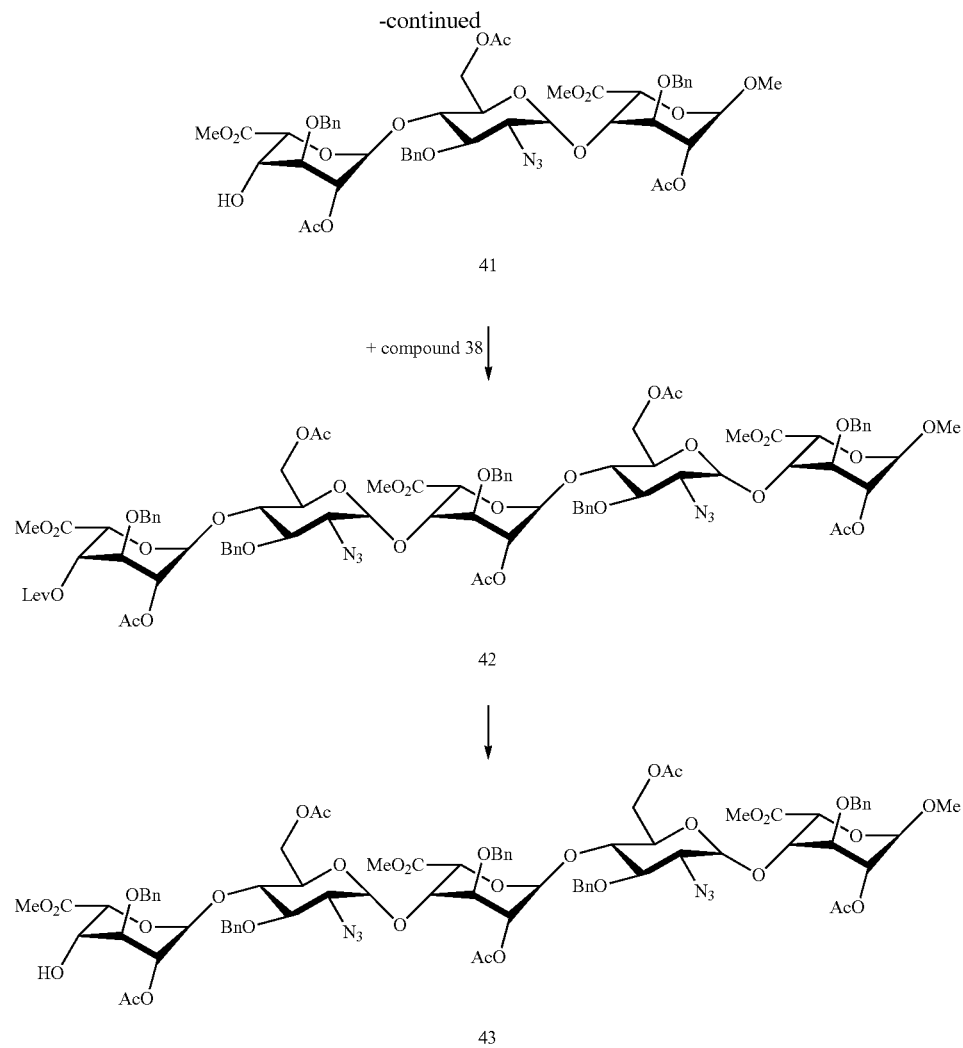

Methyl [methyl(methyl 2-O-acetyl-3-O-benzyl-4-O-levulinoyl-α-L-idopyranosyluronate)-(1→4)-(6-O-acetyl-2-azido-3-O-benzyl-2-deoxy-α-D-glucopyranosyl)-(1→4)-2-O-acetyl-3-O-benzyl-α-L-idopyranoside]uronate (40)

A mixture of the imidate 38 (1.1 g, 1.22 mmol), prepared according to the method described by C. Tabeur et al., BioOrg. Med. Chem. (1999) 7, 2003-2012, the glycosyl acceptor 39 (864 mg, 2.44 mmol), prepared according to the method described by Koshida, S. et al., Tetrahedron Lett., 1999, 40, 5725-5728, and powdered 4 Å molecular sieves (914 mg) in toluene (43 mL) is stirred under an argon atmosphere for 1 hour at 25° C. The reaction mixture is cooled to −20° C. and a 1 M solution of tert-butyldimethylsilyl triflate in dichloromethane (183 μL) is added. After stirring for 1 hour, the reaction medium is neutralized by addition of solid sodium hydrogen carbonate. After filtering through Celite® and concentrating, the residue obtained is chromatographed on a Sephadex® LH20 column (120×3 cm, 1/1 v/v dichloromethane/ethanol) followed by chromatography on a column of silica gel (1/1 v/v toluene/ethyl acetate) to give compound 40 (936 mg).

TLC: Rf=0.38, silica gel, 1/1 v/v toluene/ethyl acetate

Methyl [methyl(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-2-O-acetyl-3-O-benzyl-α-L-idopyranoside]uronate (41)

Compound 40 (2.56 g, 2.34 mmol) is treated according to the same procedure as that described for the preparation of compound 23 to give compound 41 (2.17 g) after flash chromatography on a column of silica gel (1/1 v/v toluene/ethyl acetate).

TLC: Rf=0.35, silica gel, 1/1 v/v toluene/ethyl acetate

Methyl [methyl(methyl 2-O-acetyl-3-O-benzyl-4-O-levulinoyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-2-O-acetyl-3-O-benzyl-α-L-idopyranoside]uronate (42)

A mixture of the imidate 38 (1.1 g, 1.22 mmol), the glycosyl acceptor 41 (1.2 g, 1.20 mmol) and powdered 4 Å molecular sieves (903 mg) in dichloromethane (42 mL) is stirred under an argon atmosphere for 1 hour at 25° C. The reaction mixture is cooled to −20° C. and a 1 M solution of tert-butyldimethylsilyl triflate in dichloromethane (181 μL) is added. After 15 minutes, the reaction medium is neutralized by addition of solid sodium hydrogen carbonate. After filtering and concentrating, the residue obtained is purified by chromatography on a size exclusion column (Sephadex® LH20, 190×3.2 cm, 1/1 v/v dichloromethane/ethanol) followed by chromatography on a column of silica gel (1/1 v/v toluene/ethyl acetate) to give 1.63 g of compound 42.

TLC: Rf=0.30, silica gel, 1/1 v/v toluene/ethyl acetate

Methyl[methyl(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-2-O-acetyl-3-O-benzyl-α-L-idopyranoside]uronate (43)

Compound 42 (3.90 g, 2.25 mmol) is treated according to the same procedure as that described for the preparation of compound 23. Chromatography on a column of silica gel (1/1 v/v toluene/ethyl acetate) gives compound 43 (3.39 g).

TLC: Rf=0.33, silica gel, 1/1 v/v toluene/ethyl acetate application WO 2006/021653) in N,N-dimethylformamide (210 mL) is added, at 0° C. and under argon, benzyl bromide (25 mL, 211 mmol) and then 55% NaH (3 g, 126 mmol). After 20 minutes of magnetic stirring, methanol is added (30 mL), the reaction medium is concentrated under vacuum, and the crude reaction product is diluted with ethyl acetate, washed with water and then with saturated aqueous sodium chloride solution, dried ($Na_2SO_4$), filtered and concentrated. The residue obtained is used in the following step without purification.

LC-MS m/z 871.7 [$(M+NH_4)^+$]. $T_R$=13.86 min (2-O-acetyl-3,4-di-O-benzyl-6-O-tert-butyldimethyl-silyl-α-L-idopyranosyl)-(1→4)-1,6-anhydro-2-azido-3-O-benzyl-2-deoxy-β-D-glucopyranose (46)

To a solution of crude compound 45 (38.6 g) in dichloromethane (1.6 L) are added water (80 mL) and then, at 0° C., DDQ (14.2 g). After stirring for 4 hours 45 minutes at 0° C., the medium is diluted with dichloromethane and aqueous sodium hydrogen carbonate solution is added. The organic phase is then washed with water, dried ($Na_2SO_4$), filtered SCHEME 8: Preparation of the disaccharide 50

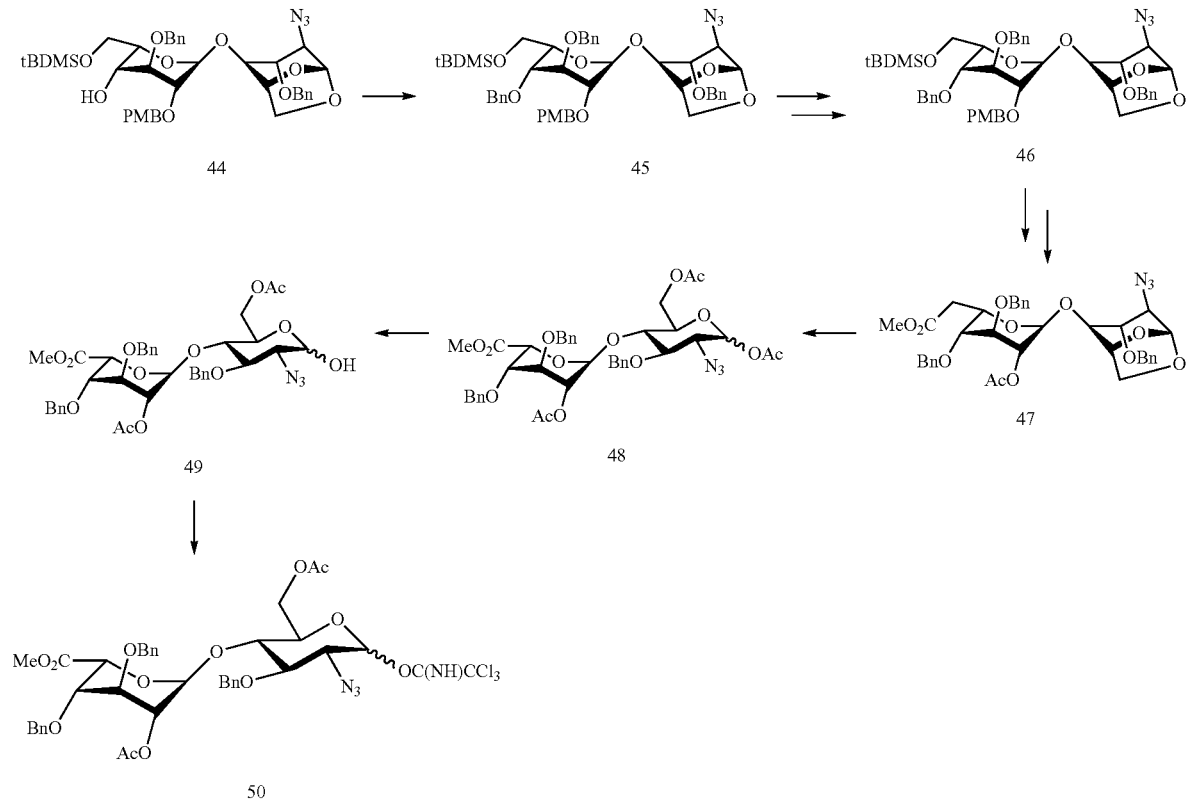

(3,4-di-O-benzyl-2-O-(4-methoxy)benzyl-6-O-tert-butyldimethylsilyl-α-L-idopyranosyl)-(1→4)-1,6-anhydro-2-azido-3-O-benzyl-2-deoxy-β-D-glucopyranose (45)

To a solution of compound 44 (32.3 g, 42.2 mmol) (described in the preparation of compound 108 of patent and concentrated. The compound obtained is used in the following step without purification.

The residue obtained is dissolved in dichloromethane (350 mL), and triethylamine (13 mL), 4-dimethylaminopyridine (2 g) and acetic anhydride (60 mL) are added. After magnetic stirring for 10 minutes at 0° C., and then 1 hour 45 minutes at room temperature, the reaction mixture is diluted with dichloromethane, and then washed successively with aqueous 10% potassium hydrogen sulfate solution, water, and the organic phase is then dried (Na$_2$SO$_4$), filtered and concentrated.

The residue obtained is purified on silica (ethyl acetate/cyclohexane) to give compound 46 (26.8 g).

LC-MS m/z 798.3 [(M+Na)$^+$]. T$_R$=12.97 min (Methyl 2-O-acetyl-3,4-di-O-benzyl-α-L-idopyranosyluronate)-(1→4)-1,6-anhydro-2-azido-3-O-benzyl-2-deoxy-β-D-glucopyranose (47)

To a solution of compound 46 (26.3 g, 33.9 mmol) in acetone (1.4 L) is added, at 0° C., a solution of CrO$_3$ (10.5 g) in aqueous 3.5 M H$_2$SO$_4$ (47 mL). After mechanical stirring for 4 hours at 0° C., the reaction medium is diluted with dichloromethane, washed with water until neutral, and the organic phase is then dried (Na$_2$SO$_4$), filtered and concentrated. The compound obtained is used in the following step without purification.

The residue obtained is dissolved in N,N-dimethylformamide (210 mL), and potassium hydrogen carbonate (17 g) and methyl iodide (21 mL) are added. The reaction mixture is stirred at room temperature for 16 hours, and then concentrated under vacuum. The residue is diluted with ethyl acetate and then washed with water, with saturated aqueous sodium thiosulfate solution, with saturated aqueous sodium chloride solution, and then dried (Na$_2$SO$_4$), filtered and concentrated. The compound obtained is used in the following step without purification.

LC-MS m/z 707.3 [(M+NH$_4$)$^+$]. T$_R$=10.37 min (Methyl 2-O-acetyl-3,4-di-O-benzyl-α-L-idopyranosyluronate)-(1→4)-1,6-di-O-acetyl-2-azido-3-O-benzyl-2-deoxy-α,β-D-glucopyranose (48)

The crude residue obtained in the preceding step is dissolved in acetic anhydride (177 mL) and trifluoroacetic acid (TFA) (17.7 mL) is then added. The reaction mixture is stirred for 16 hours, and is then concentrated, co-evaporated with toluene and purified on silica gel (cyclohexane/ethyl acetate), to give compound 48 (17.4 g).

LC-MS m/z 809.3 [(M+NH$_4$)$^+$]. T$_R$=10.81 min (Methyl 2-O-acetyl-3,4-di-O-benzyl-α-L-idopyranosyluronate)-(1→4)-6-O-acetyl-2-azido-3-O-benzyl-2-deoxy-α,β-D-glucopyranose (49)

To a solution of compound 48 (7 g, 8.84 mmol) in diethyl ether (303 mL) is added, at 0° C. and under argon, benzylamine (BnNH$_2$) (29.7 mL). After magnetic stirring for 1 hour at 0° C. and then for 6 hours at room temperature, the reaction mixture is neutralized with cold aqueous 1N HCl solution, washed with water, dried (Na$_2$SO$_4$), filtered and concentrated, and purified on silica gel (ethyl acetate/cyclohexane) to give compound 49 (5.95 g).

LC-MS m/z 767.7 [(M+NH$_4$)$^+$]. T$_R$=1.64 min (Methyl 2-O-acetyl-3,4-di-O-benzyl-α-L-idopyranosyluronate)-(1→4)-6-O-acetyl-2-azido-3-O-benzyl-2-deoxy-α,β-D-glucopyranose trichloroacetimidate (50)

To a solution of compound 49 (5.94 g, 7.9 mmol) in dichloromethane (150 mL) are added, under argon, cesium carbonate (Cs$_2$CO$_3$) (4.1 g) and then trichloroacetonitrile (CCl$_3$CN) (3.9 mL). After stirring for 45 minutes at room temperature, the reaction mixture is filtered and then concentrated. The residue is purified on silica gel (ethyl acetate/cyclohexane+0.1% triethylamine) to give compound 50 (5.7 g).

LC-MS m/z 912.0 [(M+NH$_4$)$^+$]. T$_R$=1.81 min

SCHEME 9: Preparation of the heptasaccharide 55

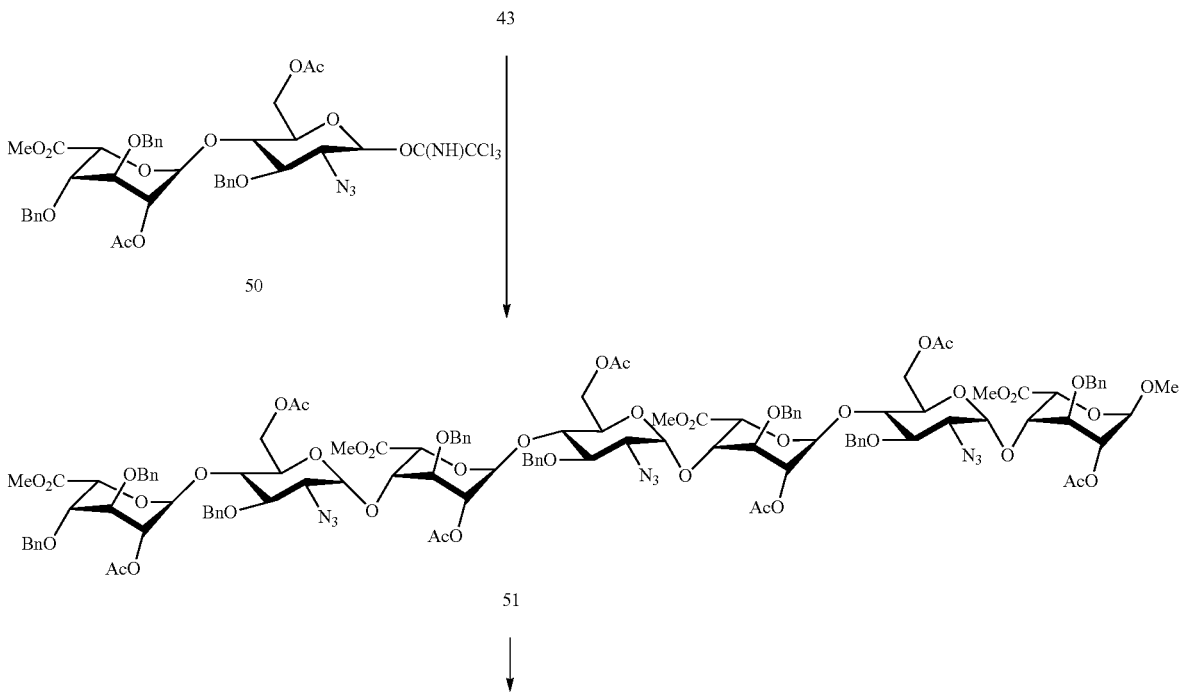

39 -continued 40
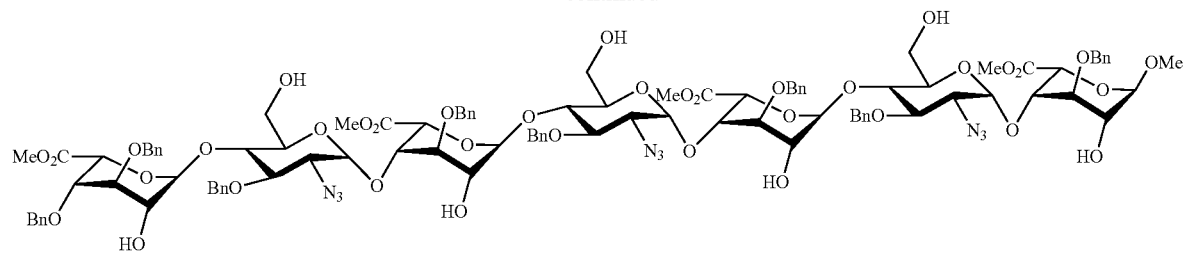
52
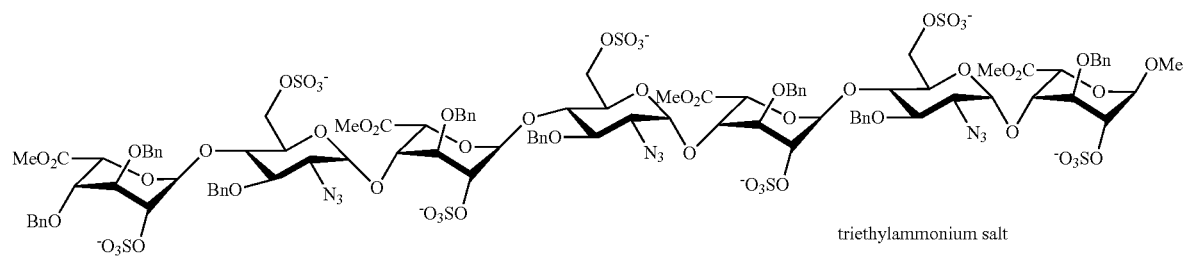
triethylammonium salt
53
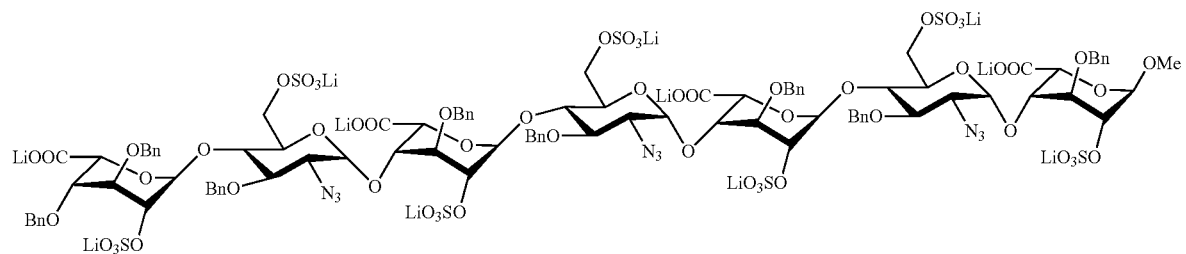
54
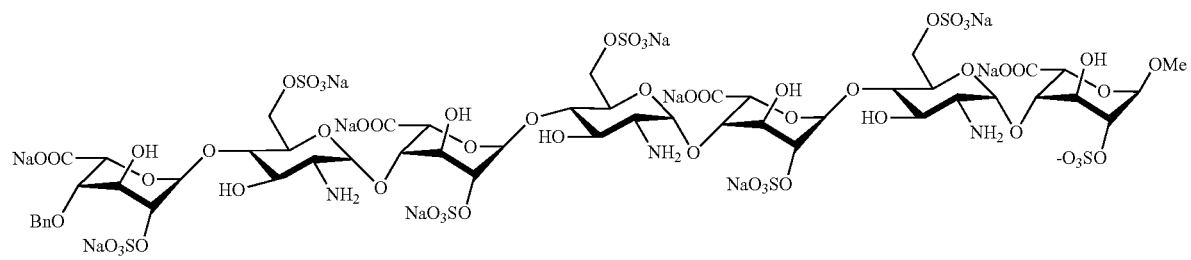
55

Methyl {methyl(methyl 2-O-acetyl-3,4-di-O-benzyl-α-L-idopyranosyluronate)-(1→4)-(6-O-acetyl-2-azido-3-O-benzyl-2-deoxy-α-D-glucopyranosyl)-(1→4)-[(methyl 2-O-acetyl-3-O-benzyl-α-L-idopyranosyluronate)-(1→4)-(6-O-acetyl-2-azido-3-O-benzyl-2-deoxy-α-D-glycopyranosyl)-(1→4)]$_2$-2-O-acetyl-3-O-benzyl-α-L-idopyranoside}uronate (51)

A mixture of the glycosyl acceptor 43 (200 mg, 0.12 mmol), the imidate 50 (163 mg, 0.18 mmol) and powdered 4 Å molecular sieves (137 mg) in dichloromethane (6.5 mL) is stirred under an argon atmosphere for 1 hour at 25° C. The reaction mixture is cooled to −20° C. and a 1 M solution of tert-butyldimethylsilyl triflate in dichloromethane (27 μL) is added. After 1 hour, the reaction medium is neutralized by addition of solid sodium hydrogen carbonate. After filtering and concentrating, the residue obtained is purified by chromatography on a size exclusion column (Sephadex® LH20, 90×3 cm, 1/1 v/v dichloromethane/ethanol) followed by chromatography on a column of silica gel (2/1 v/v toluene/ethyl acetate) to give compound 51 (212 mg).
TLC: Rf=0.38, silica gel, 1/1 v/v toluene/ethyl acetate.

Methyl {methyl(methyl 3,4-di-O-benzyl-α-L-idopyranosyluronate)-(1→4)-(2-azido-3-O-benzyl-2-deoxy-α-D-glucopyranosyl)-(1→4)-[(methyl 3-O-benzyl-α-L-idopyranosyluronate)-(1→4)-(2-azido-3-O-benzyl-2-deoxy-α-D-glucopyranosyl)-(1→4)]$_2$-3-O-benzyl-α-L-idopyranoside}uronate (52)

Compound 51 (271 mg, 0.11 mmol) is treated according to the same procedure as that described for the preparation of compound 27 to give compound 52 (186 mg) after chromatography on a size exclusion column (Sephadex® LH20, 120×3 cm, 1/1 v/v dichloromethane/ethanol) followed by chromatography on a column of silica gel (5/3 v/v toluene/acetone).
TLC: Rf=0.65, silica gel, 4/3 v/v toluene/ethyl acetate Methyl {methyl(methyl 3,4-di-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-[(methyl 3-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)]$_2$-3-O-benzyl-2-O-triethylammonium sulfonato-α-L-idopyranoside}uronate (53)

Compound 52 (172 mg, 0.08 mmol) is treated according to the same procedure as that described for the preparation of compound 28 to give compound 53 (196 mg) after size exclusion chromatography (Sephadex® LH20, 120×3 cm, 1/1 v/v dichloromethane/ethanol).
$^1$H NMR (D$_2$O) δ of the main anomeric protons: 5.41; 5.38; 5.34; 5.15; 5.14; 5.05; 5.15; 5.02 ppm.

Lithium {methyl(lithium 3,4-di-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-[(lithium 3-O-benzyl-2-O-lithium sulfonato-α-L-idopyranosyluronate)-(1→4)-(2-azido-3-O-benzyl-2-deoxy-6-O-lithium sulfonato-α-D-glucopyranosyl-(1→4)]$_2$-3-O-benzyl-2-O-lithium sulfonato-α-L-idopyranoside}uronate (54)

Compound 53 (186 mg, 70.7 μmol) is treated according to the same procedure as that described for the preparation of compound 29 to give compound 54 (141 mg) after size exclusion chromatography (Sephadex® LH20, 120×3 cm, 50/50/1 v/v/v dichloromethane/ethanol/water).
TLC: Rf=0.24, silica gel, 27/19/4.2/11 v/v/v/v ethyl acetate/pyridine/acetic acid/water Sodium {methyl(sodium 2-O-sodium sulfonato-α-L-idopyranosyluronate)-(1→4)-(2-amino-2-deoxy-6-O-sodium sulfonato-α-D-glucopyranosyl)-(1→4)-[(sodium 2-O-sodium sulfonato-α-L-idopyranosyluronate)-(1→4)-(2-amino-2-deoxy-6-O-sodium sulfonato-α-D-glucopyranosyl)-(1→4)]$_2$-2-O-sodium sulfonato-α-L-idopyranoside}uronate (55)

A solution of compound 54 (60.0 mg, 0.022 mmol) in a 1/1 v/v tert-butanol/water mixture (6 mL) is treated under pressure of hydrogen (<200 mbar) in the presence of 10% palladium-on-charcoal (60 mg) at room temperature. After stirring for 24 hours, the reaction medium is filtered (Millipore® LSWP 5 μm filter) and then concentrated to dryness. The crude product 55 thus obtained (48.7 mg) is used without further purification in the following step.

SCHEME 10: Preparation of the glycoside acceptor 60

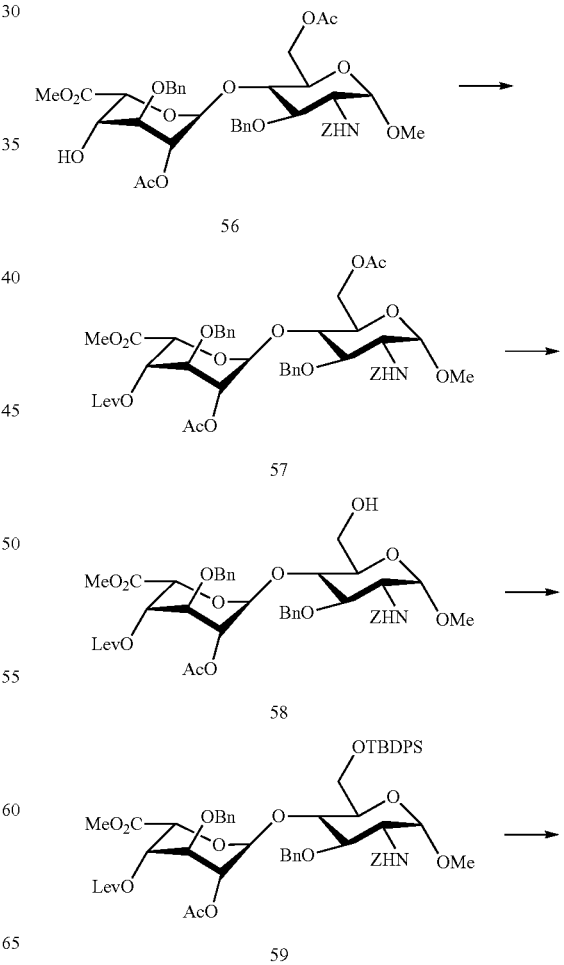

-continued

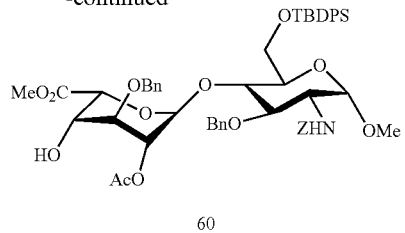

60

Methyl(methyl 2-O-acetyl-3-O-benzyl-4-O-levulinoyl-α-L-idopyranosyluronate)-(1→4)-6-O-acetyl-3-O-benzyl-2-benzyloxycarbonylamino-2-deoxy-α-D-glucopyranoside (57)

To a solution of compound 56 (23.5 g, 30 mmol; prepared according to the method described in *Carbohydrate Research* (1987), 167, 67-75) in dichloromethane (600 mL) are added, at 0° C. and under an inert atmosphere, 4-dimethylaminopyridine (733 mg, 6 mmol), 1-(3-dimethylaminopropyl)-3-ethylcarbodiimide hydrochloride (11.5 g, 60 mmol) and levulinic acid (6.2 mL, 60 mmol). After stirring for 16 hours at room temperature, the mixture is diluted with dichloromethane (1.5 L). The organic phase is washed successively with aqueous 10% potassium hydrogen sulfate solution, with water, with saturated sodium hydrogen carbonate solution and then with water, dried over sodium sulfate, filtered and then evaporated to dryness. The residue is purified by flash chromatography on a column of silica gel (1/3 cyclohexane/ethyl acetate) to give compound 57 (22.6 g).

Rf=0.37, silica gel, 1/3 v/v cyclohexane/ethyl acetate

Methyl(methyl 2-O-acetyl-3-O-benzyl-4-O-levulinoyl-α-L-idopyranosyluronate)-(1→4)-3-O-benzyl-2-benzyloxycarbonylamino-2-deoxy-α-D-glucopyranoside (58)

To a solution of compound 57 (20.2 g, 23 mmol) in a 1/1 tetrahydrofuran/methanol mixture (140 mL) is added, under an inert atmosphere, [tBu$_2$SnCl(OH)]$_2$ (226 mg, 0.79 mmol) prepared according to A. Orita et al., *Chem. Eur. J.* (2001) 7, 3321. The reaction medium is stirred for 38 hours at 35° C. After concentrating, the residue (20.8 g) is used in the following step without purification.

Rf=0.23, silica gel, 1/3 v/v cyclohexane/ethyl acetate

Methyl(methyl 2-O-acetyl-3-O-benzyl-4-O-levulinoyl-α-L-idopyranosyluronate)-(1→4)-3-O-benzyl-2-benzyloxycarbonylamino-6-O-tert-butyldiphenylsilyl-2-deoxy-α-D-glucopyranoside (59)

To a solution of crude compound 58 (23 mmol) in dichloromethane (190 mL) are added, at 0° C. and under an inert atmosphere, triethylamine (8 mL, 57.5 mmol), 4-dimethylaminopyridine (1.4 g, 11.5 mmol) and tert-butyldiphenylsilyl chloride (12 mL, 46.0 mmol). The reaction medium is stirred for hours at room temperature. The reaction mixture is diluted with dichloromethane. The organic phase is washed successively with saturated aqueous sodium chloride solution and then with water, dried over sodium sulfate, filtered and then evaporated. The residue is purified by flash chromatography on a column of silica gel (2/1 cyclohexane/ethyl acetate) to give compound 59 (24.4 g).

Rf=0.42, silica gel, 2/1 v/v cyclohexane/ethyl acetate

Methyl(methyl 2-O-acetyl-3-O-benzyl-α-L-idopyranosyluronate)-(1→4)-3-O-benzyl-2-benzyloxycarbonylamino-6-O-tert-butyldiphenylsilyl-2-deoxy-α-D-glucopyranoside (60)

To a solution of compound 59 (22.6 g, 20.0 mmol) in a 1/2 toluene/ethanol mixture (2.5 L) is added hydrazine acetate (9.21 g, 100.0 mmol). The reaction medium is stirred for 30 minutes at room temperature. After concentrating, the residue is purified by flash chromatography on a column of silica gel (2/1 cyclohexane/ethyl acetate) to give 17.6 g of compound 60.

Rf=0.40, silica gel, 2/1 v/v cyclohexane/ethyl acetate

SCHEME 11: Preparation of the glycoside donor 65

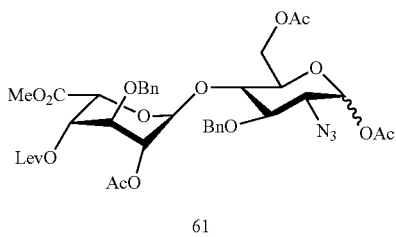

61

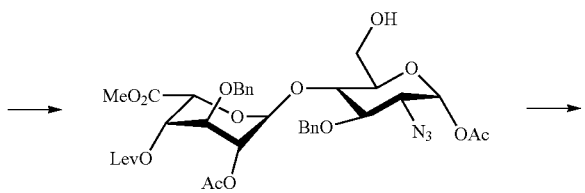

62

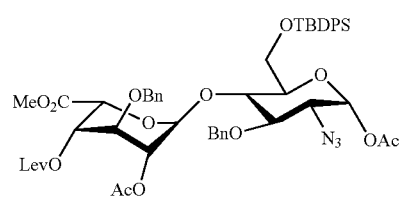

63

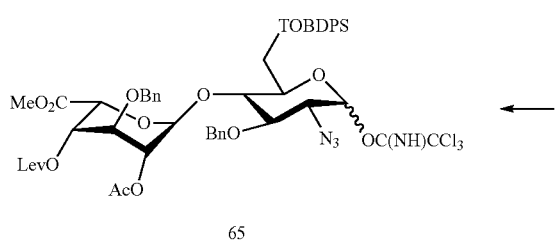

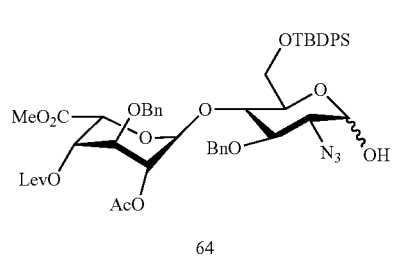

(Methyl 2-O-acetyl-3-O-benzyl-4-O-levulinoyl-α-L-idopyranosyluronate)-(1→4)-1-O-acetyl-2-azido-3-O-benzyl-2-deoxy-α-D-glucopyranose (62)

To a solution of 61 (11 g, 13.7 mmol) (prepared according to the method described by C. Tabeur et al., Carbohydr. Res., 281 (1996) 253-276) in a 1/1 methanol/tetrahydrofuran mixture (80 mL) is added [tBu₂SnCl(OH)]₂ (0.55 g) prepared according to A. Orita et al., Chem. Eur. J. (2001) 7, 3321. After stirring at 35° C. for 5.5 hours, and then at room temperature for 16 hours, and then again at 35° C. for 4 hours, the reaction mixture is concentrated under vacuum and then purified by chromatography to give compound 62 (5.97 g).

LC-MS m/z 780.2 [(M+Na)⁺]. $T_R$=9.14 min (Methyl 2-O-acetyl-3-O-benzyl-4-O-levulinoyl-α-L-idopyranosyluronate)-(1→4)-1-O-acetyl-2-azido-3-O-benzyl-6-O-tert-butyldiphenylsilyl-2-deoxy-α-D-glucopyranose (63)

Compound 62 (5.97 g, 7.88 mmol) is dissolved in dichloromethane (63 mL). At 0° C. and under argon, 4-dimethylaminopyridine (0.481 g), triethylamine (2.7 mL), and tert-butyldiphenylsilyl chloride (4 mL) are successively added. After magnetic stirring for 4 hours, the reaction medium is diluted with dichloromethane, washed with aqueous 10% potassium hydrogen sulfate solution, with water, dried (Na₂SO₄), filtered and concentrated. The residue obtained is purified on silica (ethyl acetate/heptane) to give compound 63 (7 g).

LC-MS m/z 1018.3 [(M+Na)⁺]. $T_R$=12.33 min (Methyl 2-O-acetyl-3-O-benzyl-4-O-levulinoyl-α-L-idopyranosyluronate)-(1→4)-2-azido-3-O-benzyl-6-O-tert-butyldiphenylsilyl-2-deoxy-α,β-D-glucopyranose (64)

To a solution of compound 63 (7 g, 7.03 mmol) in diethyl ether (70 mL), is added, at 0° C., benzylamine (BnNH₂) (29 mL). After stirring for 15 minutes at 0° C., and then for 6 hours at room temperature, the reaction mixture is diluted with ethyl acetate, and then neutralized with cold 1N HCl, washed with water, dried (Na₂SO₄), filtered and concentrated, and purified on silica gel (ethyl acetate/toluene) to give compound 64 (5.86 g).

LC-MS m/z 976.3 [(M+Na)⁺]. $T_R$=27.6/27.8 min (Methyl 2-O-acetyl-3-O-benzyl-4-O-levulinoyl-α-L-idopyranosyluronate)-(1→4)-2-azido-3-O-benzyl-6-O-tert-butyldiphenylsilyl-2-deoxy-α,β-D-glucopyranose trichloroacetimidate (65)

To a solution of compound 64 (6.5 g, 6.81 mmol) in dichloromethane (140 mL) and in the presence of powdered 4 Å molecular sieves (7 g) is added, under argon, cesium carbonate (Cs₂CO₃) (3.5 g) and then, at 0° C., trichloroacetonitrile (CCl₃CN) (3.4 mL). After stirring for 15 minutes at 0° C., and then for 5 hours at room temperature, the reaction mixture is filtered and then concentrated. The residue is purified on silica gel (1/4 ethyl acetate/toluene+ 0.1% triethylamine) to give compound 65 (6.33 g).

LC-MS m/z 1119.1 [(M+Na)]. $T_R$=31.2

SCHEME 12: Preparation of the tetrasaccharide 67

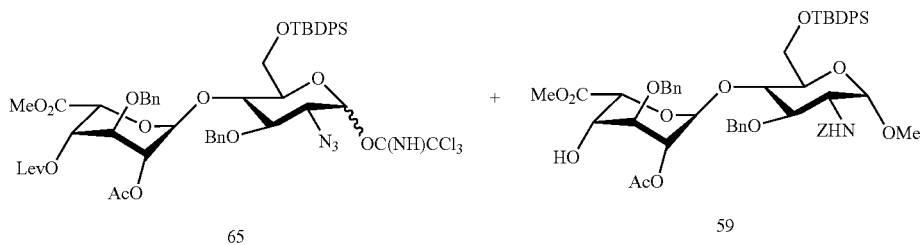

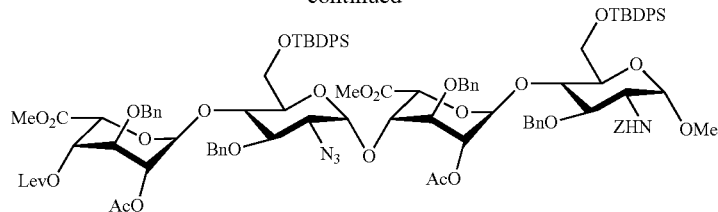

66

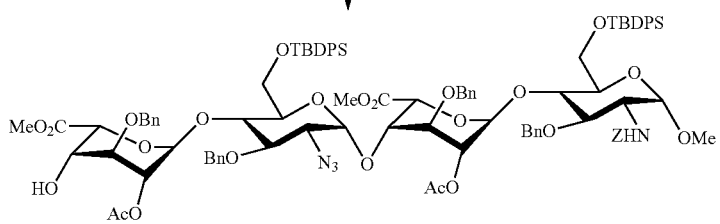

67

Methyl(methyl 2-O-acetyl-3-O-benzyl-4-O-levu-
linoyl-α-L-idopyranosyluronate)-(1→4)-(2-azido-3-
O-benzyl-6-O-tert-butyldiphenylsilyl-2-deoxy-α-D-
glucopyranosyl)-(1→4)-(methyl 2-O-acetyl-3-O-
benzyl-α-L-idopyranosyluronate)-(1→4)-3-O-
benzyl-2-benzyloxycarbonylamino-6-O-tert-
butyldiphenylsilyl-2-deoxy-α-D-glucopyranoside
(66)

A mixture of the glycosyl acceptor 59 (8.80 g, 9.00 mmol), the imidate 65 (6.58 g, 6.00 mmol) and powdered 4 Å molecular sieves (4.50 g) in dichloromethane (210 mL) is stirred under an argon atmosphere for 1 hour at 25° C. The reaction mixture is cooled to −20° C. and a 1 M solution of tert-butyldimethylsilyl triflate in dichloromethane (900 µL) is added. After 1 hour 20 minutes, the reaction medium is neutralized by addition of solid sodium hydrogen carbonate. After filtering through Celite® and concentrating, the residue obtained is chromatographed on a Sephadex® LH20 column (190×3.2 cm, 1/1 dichloromethane/ethanol) to give 8.26 g of compound 66.

Rf=0.30, silica gel, 2/1 cyclohexane/ethyl acetate

Methyl(methyl 2-O-acetyl-3-O-benzyl-α-L-idopyra-
nosyluronate)-(1→4)-(2-azido-3-O-benzyl-6-O-tert-
butyldiphenylsilyl-2-deoxy-α-D-glucopyranosyl)-
(1→4)-(methyl 2-O-acetyl-3-O-benzyl-α-L-
idopyranosyluronate)-(1→4)-3-O-benzyl-2-
benzyloxycarbonylamino-6-O-tert-
butyldiphenylsilyl-2-deoxy-α-D-glucopyranoside
(67)

Compound 66 (8.26 g, 4.31 mmol) is transformed into compound 67 (6.41 g) according to the same procedure as that described for the synthesis of compound 23.

Rf=0.34, silica gel, 2/1 cyclohexane/ethyl acetate

SCHEME 13: Preparation of the hexasaccharide 69

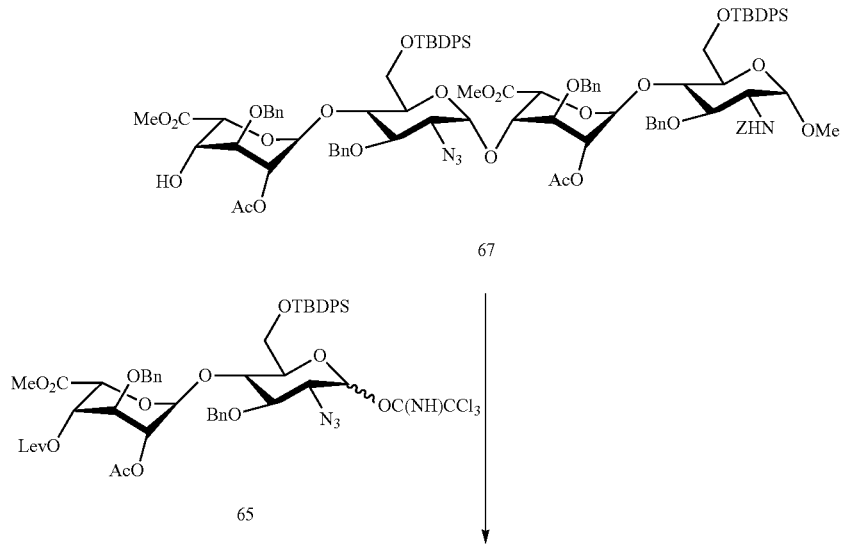

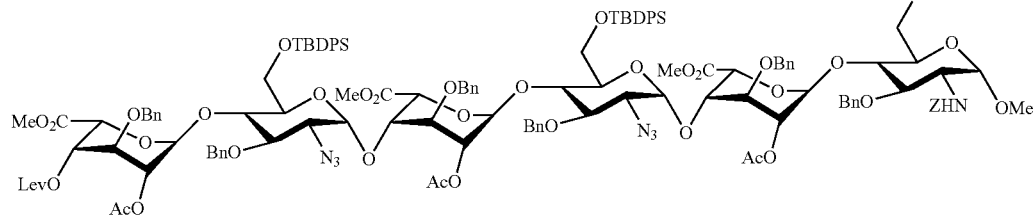

68

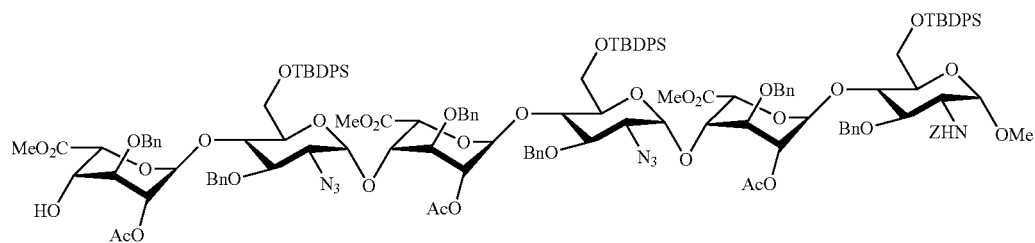

69

Methyl(methyl 2-O-acetyl-3-O-benzyl-4-O-levu-linoyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyluronate)-(1→4)-3-O-benzyl-2-benzyloxycarbonylamino-6-O-tert-butyldiphenylsilyl-2-deoxy-α-D-glucopyranoside (68)

A mixture of the glycosyl acceptor 67 (7.42 g, 4.09 mmol), the imidate 65 (6.73 g, 6.1 mmol), and powdered 4 Å molecular sieves (4.60 g) in dichloromethane (215 mL) is stirred under an argon atmosphere for 1 hour at 25° C. The reaction mixture is cooled to −20° C. and a 1 M solution of tert-butyldimethylsilyl triflate in dichloromethane (920 μL) is added. After 1 hour 30 minutes, the reaction medium is neutralized by addition of solid sodium hydrogen carbonate. After filtering through Celite®, the reaction medium is diluted with dichloromethane (800 mL). The organic phase is washed successively with aqueous 2% sodium hydrogen carbonate solution, with water and then dried over sodium sulfate, filtered and then evaporated to dryness. The residue obtained is purified by chromatography on a column of Sephadex® LH20 (190×3.2 cm, 1/1 dichloromethane/ethanol) followed by chromatography on a column of silica gel (6/1 toluene/ethyl acetate) to give 6.13 g of compound 68.

Rf=0.46, silica gel, 4/1 v/v toluene/ethyl acetate

Methyl(methyl 2-O-acetyl-3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyluronate)-(1→4)-3-O-benzyl-2-benzyloxycarbonylamino-6-O-tert-butyldiphenylsilyl-2-deoxy-α-D-glucopyranoside (69)

Compound 68 (7.14 g, 2.59 mmol) is transformed into compound 69 (6.07 g) according to the same procedure as that described for the preparation of compound 23.

Rf=0.37, silica gel, 2/1 v/v cyclohexane/ethyl acetate

SCHEME 14: Preparation of the disaccharide 73

44 → 70 →

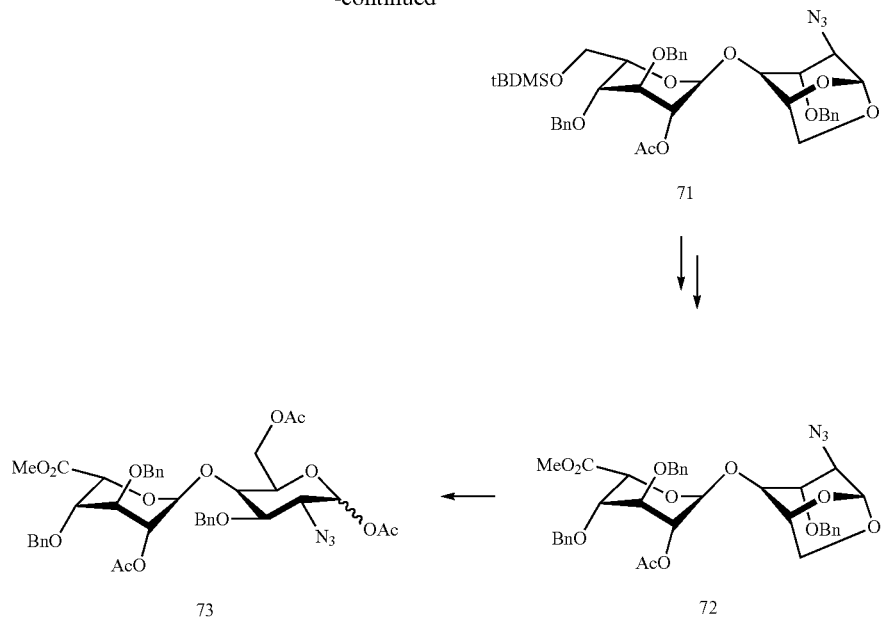

(3,4-di-O-benzyl-2-O-(4-methoxy)benzyl-6-O-tert-butyldimethylsilyl-α-L-idopyranosyl)-(1→4)-1,6-anhydro-2-azido-3-O-benzyl-2-deoxy-β-D-glucopyranose (70)

To a solution of compound 44 (32.3 g, 42.2 mmol) (described in the preparation of compound 108 of patent application WO 2006/021653) in N,N-dimethylformamide (210 mL) is added, at 0° C. and under argon, benzyl bromide (25 mL) and then 55% NaH (3 g). After 20 minutes of magnetic stirring, methanol is added (30 mL), the reaction medium is concentrated under vacuum, and the crude reaction product is diluted with ethyl acetate, washed with water and then with saturated aqueous sodium chloride solution, dried ($Na_2SO_4$), filtered and concentrated. The residue obtained (38.6 g) is used in the following step without purification.

LC-MS m/z 871.7 [(M+NH$_4$)$^+$]. $T_R$=13.86 min (2-O-acetyl-3,4-di-O-benzyl-6-O-tert-butyldimethylsilyl-α-L-idopyranosyl)-(1→4)-1,6-anhydro-2-azido-3-O-benzyl-2-deoxy-β-D-glucopyranose (71)

To a solution of crude compound 70 (38.6 g) in dichloromethane (1.6 L) are added water (80 mL) and then, at 0° C., DDQ (14.2 g). After stirring for 4 hours 45 minutes at 0° C., the medium is diluted with dichloromethane and aqueous sodium hydrogen carbonate solution is added. The organic phase is then washed with water, dried ($Na_2SO_4$), filtered and concentrated. The compound obtained is used in the following step without purification.

The residue obtained is dissolved in dichloromethane (350 mL), and then triethylamine (13 mL), 4-dimethylaminopyridine (2 g), and acetic anhydride (60 mL) are added. After magnetic stirring for 10 minutes at 0° C., and then for 1 hour 45 minutes at room temperature, the reaction mixture is diluted with dichloromethane, and then washed successively with aqueous 10% potassium hydrogen sulfate solution, water, and the organic phase is then dried ($Na_2SO_4$), filtered and concentrated. The residue obtained is purified on silica (ethyl acetate/cyclohexane) to give compound 71 (26.8 g).

LC-MS m/z 798.3 [(M+Na)$^+$]. $T_R$=12.97 min

(Methyl 2-O-acetyl-3,4-di-O-benzyl-α-L-idopyranosyl uronate)-(1→4)-1,6-anhydro-2-azido-3-O-benzyl-2-deoxy-β-D-glucopyranose (72)

To a solution of compound 71 (26.3 g, 33.9 mmol) in acetone (1.4 L) is added, at 0° C., a solution of $CrO_3$ (10.5 g) in aqueous 3.5 M $H_2SO_4$ (47 mL). After mechanical stirring for 4 hours at 0° C., the reaction medium is diluted with dichloromethane, washed with water until neutral, and then the organic phase is dried ($Na_2SO_4$), filtered and concentrated. The compound obtained is used in the following step without purification.

The residue obtained is dissolved in N,N-dimethylformamide (210 mL), and potassium hydrogen carbonate (17 g) and methyl iodide (21 mL) are added. The reaction mixture is stirred at room temperature for 16 hours, and then concentrated under vacuum. The residue is diluted with ethyl acetate and then washed with water, with saturated aqueous sodium thiosulfate solution, with saturated aqueous sodium chloride solution, and then dried ($Na_2SO_4$), filtered and concentrated. The compound obtained is used in the following step without purification.

LC-MS m/z 707.3 [(M+NH$_4$)$^+$]. $T_R$=10.37 min

(Methyl 2-O-acetyl-3,4-di-O-benzyl-α-L-idopyranosyluronate)-(1→4)-1,6-di-O-acetyl-2-azido-3-O-benzyl-2-deoxy-α,β-D-glucopyranose (73)

The crude residue obtained in the preceding step is dissolved in acetic anhydride (177 mL), and trifluoroacetic acid (TFA) (17.7 mL) is then added. The reaction mixture is stirred for 16 hours, and is then concentrated, co-evaporated with toluene, and purified on silica gel (cyclohexane/ethyl acetate), to give compound 73 (17.4 g).

LC-MS m/z 809.3 [(M+NH$_4$)$^+$]. $T_R$=10.81 min

SCHEME 15: Preparation of the glycosyl donor 77

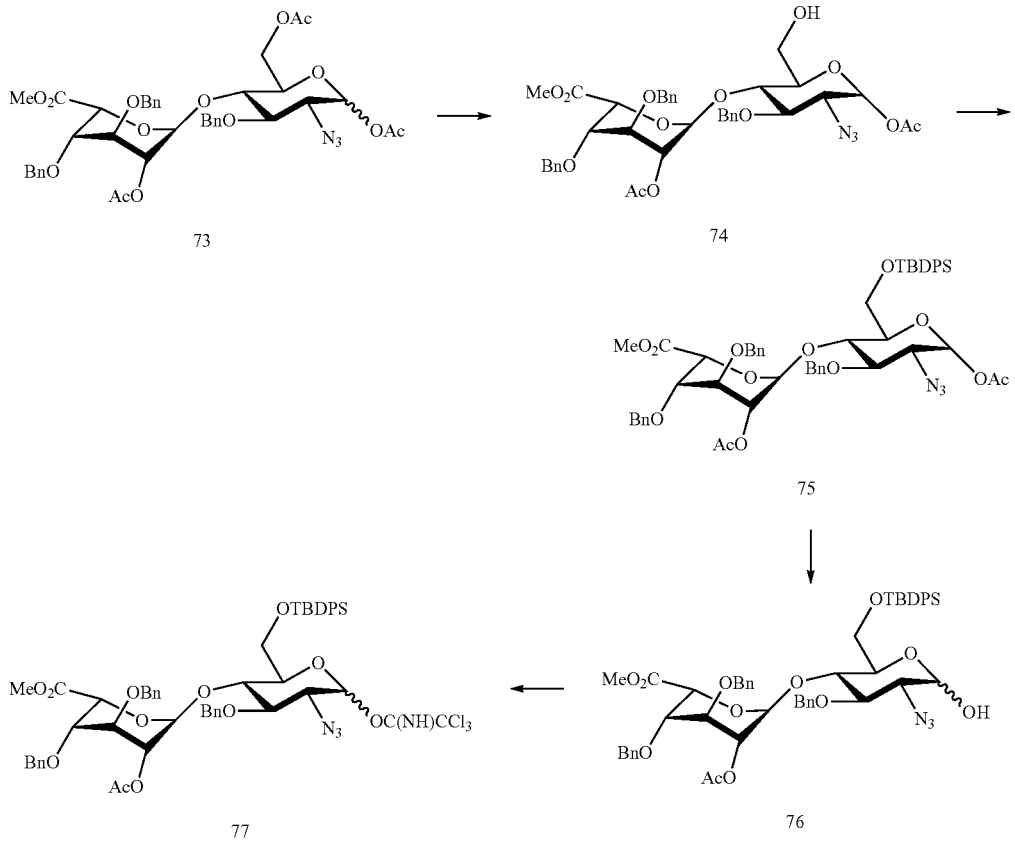

(Methyl 2-O-acetyl-3,4-di-O-benzyl-α-L-idopyranosyluronate)-(1→4)-1-O-acetyl-2-azido-3-O-benzyl-2-deoxy-α-D-glucopyranose (74)

To a solution of compound 73 (5.05 g, 6.3 mmol) in a 1/1 methanol/tetrahydrofuran mixture (76 mL) is added [tBu$_2$SnCl(OH)]$_2$ (0.25 g, 0.88 mmol), prepared according to A. Orita et al., *Chem. Eur. J.* (2001) 7, 3321. After stirring at room temperature for 72 hours, the reaction mixture is concentrated under vacuum and then purified by chromatography to give compound 74 (2.89 g).

LC-MS m/z 772.4 [(M+Na)$^+$]. $T_R$=10.23 min (Methyl 2-O-acetyl-3,4-di-O-benzyl-α-L-idopyranosyluronate)-(1→4)-1-O-acetyl-2-azido-3-O-benzyl-6-O-tert-butyldiphenylsilyl-2-deoxy-α-D-glucopyranose (75)

Compound 74 (2.89 g, 3.86 mmol) is dissolved in dichloromethane (31 mL). At 0° C. and under argon, triethylamine (1.3 mL), 4-dimethylaminopyridine (0.235 g) and tert-butyldiphenylsilyl chloride (2 mL) are successively added. After magnetic stirring for 3 hours, the reaction medium is diluted with dichloromethane, washed with aqueous 10% potassium hydrogen sulfate solution, with water, dried (Na$_2$SO$_4$), filtered and concentrated. The residue obtained is purified on silica (ethyl acetate/cyclohexane) to give compound 75 (3.4 g).

LC-MS m/z 1010.6 [(M+Na)$^+$]. $T_R$=13.10 min (Methyl 2-O-acetyl-3,4-di-O-benzyl-α-L-idopyranosyluronate)-(1→4)-2-azido-3-O-benzyl-6-O-tert-butyldiphenylsilyl-2-deoxy-α,β-D-glucopyranose (76)

To a solution of compound 75 (3.44 g, 3.48 mmol) in diethyl ether (35 mL) is added, at 0° C., benzylamine (BnNH$_2$) (14.5 mL). After stirring for 8 hours at room temperature, the reaction mixture is placed at −18° C. for 16 hours, and then again for 2.5 hours at room temperature. The medium is then diluted with ethyl acetate, and then neutralized with cold 1N HCl, washed with water, dried (Na$_2$SO$_4$), filtered and concentrated, and purified on silica gel (ethyl acetate/cyclohexane 15/85) to give 76 (3.83 g).

LC-MS m/z 963.6 [(M+NH$_4$)$^+$]. $T_R$=12.37, 12.47 min (Methyl 2-O-acetyl-3,4-di-O-benzyl-α-L-idopyranosyluronate)-(1→4)-2-azido-3-O-benzyl-6-O-tert-butyldiphenylsilyl-2-deoxy-α,β-D-glucopyranose trichloroacetimidate (77)

To a solution of compound 76 (2.99 g, 3.16 mmol) in dichloromethane (60 mL) and in the presence of powdered 4 Å molecular sieves (3 g) are added, at 0° C. under argon, cesium carbonate (Cs$_2$CO$_3$) (1.6 g), and then trichloroacetonitrile (CCl$_3$CN) (1.6 mL). After stirring for 20 minutes at 0° C., for 7 hours at room temperature, storing at −18° C. for 16 hours, and then magnetic stirring for 8 hours at room temperature, storing at −18° C. for 16 hours, and finally magnetic stirring for 1 hour at room temperature, the reaction mixture is filtered and then concentrated. The residue is purified on silica gel (15/85 ethyl acetate/cyclohexane+0.1% triethylamine) to give compound 77 (2.69 g).

LC-MS m/z 1113.4 [(M+Na)$^+$]. $T_R$=14.58 min

SCHEME 16: Preparation of the octasaccharide 79
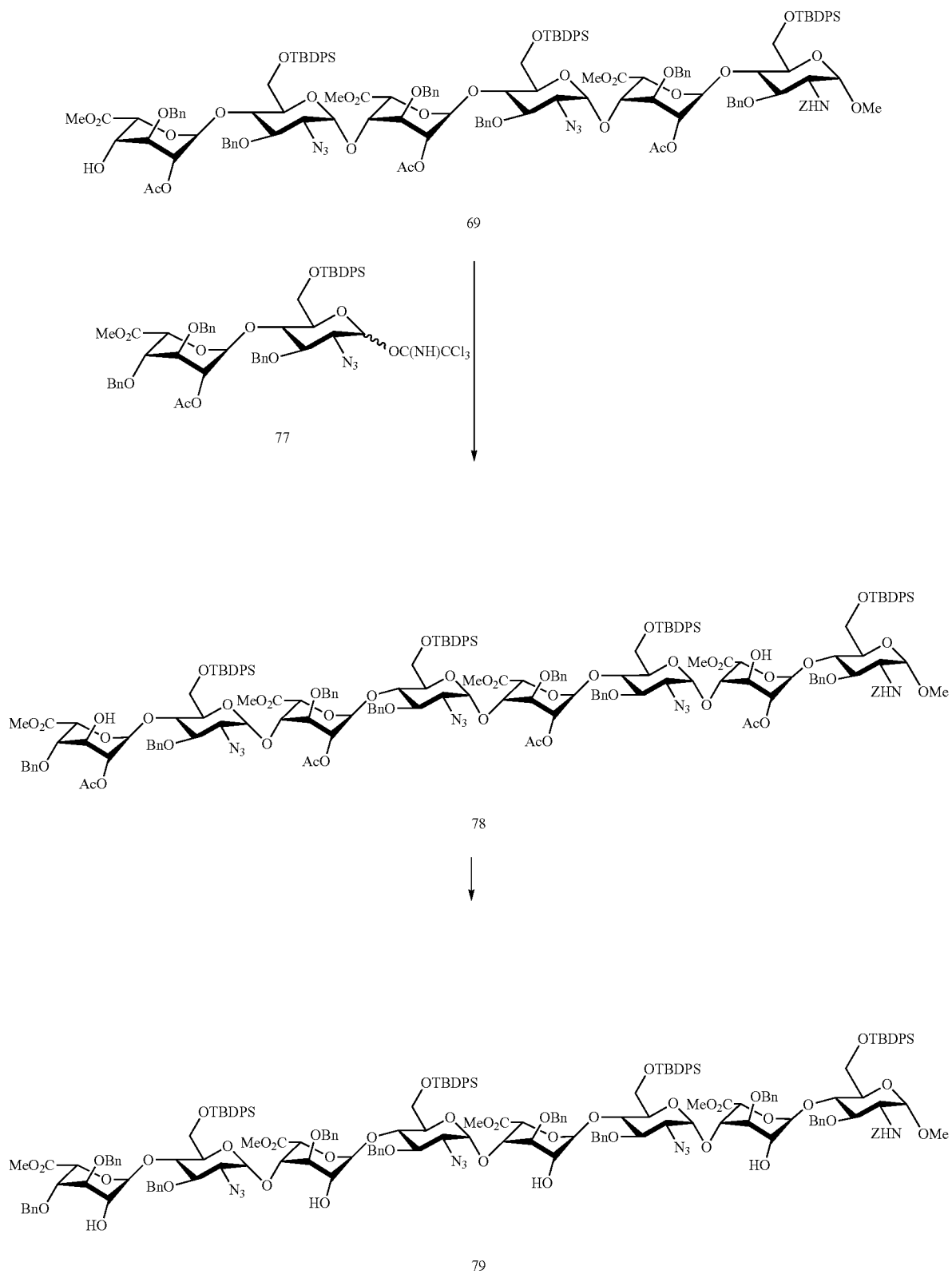

Methyl(methyl 2-O-acetyl-3,4-di-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-[(methyl 2-O-acetyl-3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)]2-(methyl 2-O-acetyl-3-O-benzyl-α-L-idopyranosyluronate)-(1→4)-3-O-benzyl-2-benzyloxycarbonylamino-6-O-tert-butyldiphenylsilyl-2-deoxy-α-D-glucopyranoside (78)

A mixture of the glycosyl acceptor 69 (3.50 g, 1.32 mmol), the imidate 77 (2.16 g, 1.98 mmol) and powdered 4 Å molecular sieves (1.48 g) in dichloromethane (69 mL) is stirred under an argon atmosphere for 1 hour at room temperature. The reaction mixture is cooled to −20° C. and a 1 M solution of tert-butyldimethylsilyl triflate in dichloromethane (297 µL) is added. After 2 hours 30 minutes, the reaction medium is neutralized by addition of solid sodium hydrogen carbonate. After filtering through Celite®, the reaction medium is diluted with dichloromethane (400 mL). The organic phase is washed successively with aqueous 2% sodium hydrogen carbonate solution, with water and then dried over sodium sulfate, filtered and then evaporated to dryness. The residue obtained is purified by chromatography on a column of Sephadex® LH20 (190×3.2 cm, 1/1 dichloromethane/ethanol) followed by chromatography on a column of silica gel (4/1 cyclohexane/ethyl acetate) to give 3.04 g of compound 78.

Rf=0.30, silica gel, 3/1 cyclohexane/ethyl acetate

Methyl(methyl 3,4-di-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-[(methyl 3-O-benzyl-α-L-idopyranosyluronate)-(1→4)-(2-azido-3-O-benzyl-6-O-tert-butyldiphensilyl-2-deoxy-α-D-glycopyranosyl)-(1→4)]2-(methyl 3-O-benzyl-α-L-idopyranosyluronate)-(1→4)-3-O-benzyl-2-benzyloxycarbonylamino-6-O-tert-butyldiphenylsilyl-2-deoxy-α-D-glucopyranoside (79)

To a solution of compound 78 (2.23 g, 0.623 mmol) in a 2/3 dichloromethane/methanol mixture (187 mL) containing 3 Å molecular sieves (78 mg) is added, under an argon atmosphere and at 0° C., a 1 M solution of sodium methoxide in methanol (99.7 µL). After 24 hours at room temperature, the reaction medium is neutralized with Dowex AG 50 W×4 H⁺ resin. After filtering and concentrating, the residue is chromatographed on a column of Sephadex® LH20 (120×3 cm, 1/1 dichloromethane/ethanol) followed by flash chromatography on a column of silica gel (100/0→66/34 cyclohexane/ethyl acetate) to give 1.80 g of compound 79.

Rf=0.38, silica gel, 3/1 v/v cyclohexane/ethyl acetate

SCHEME 17: Preparation of the octasaccharides 80, 81, 82, 83, 84, 85, 86 and 87

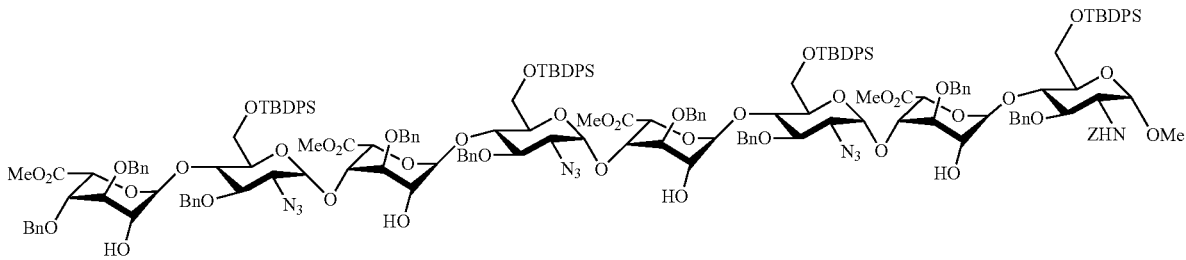

79

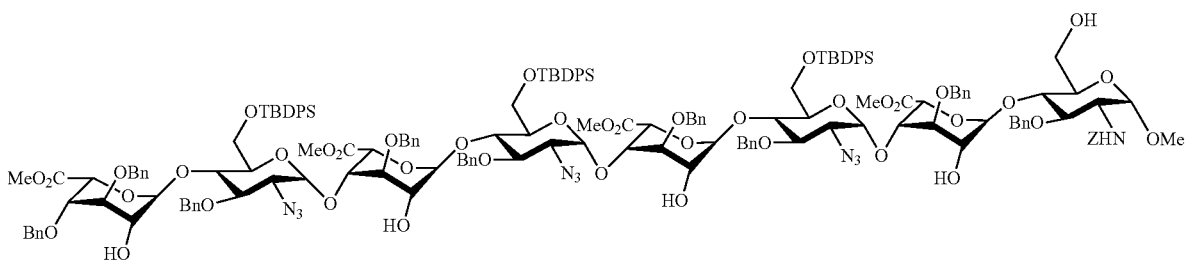

80

+

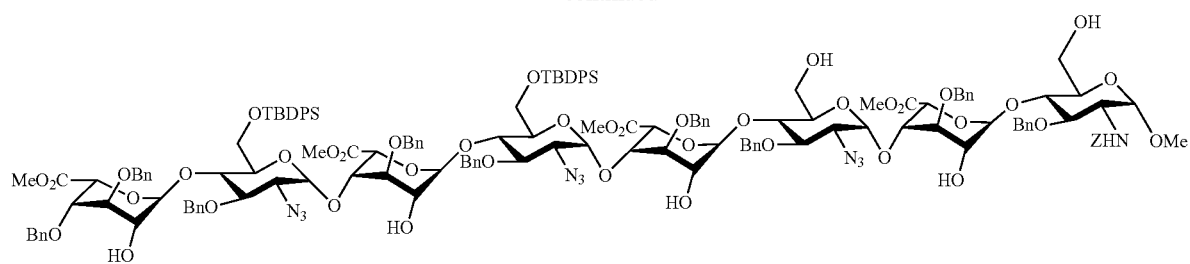
81
+
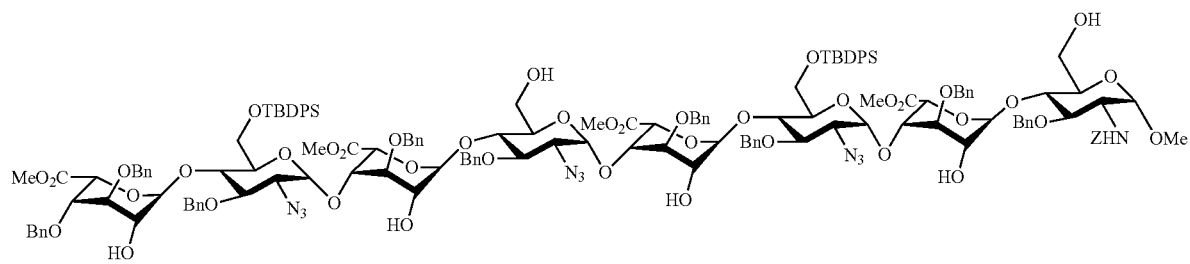
82
+
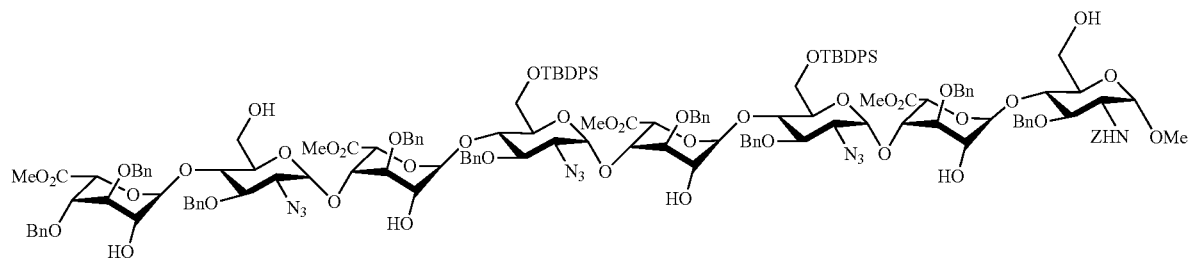
83
+
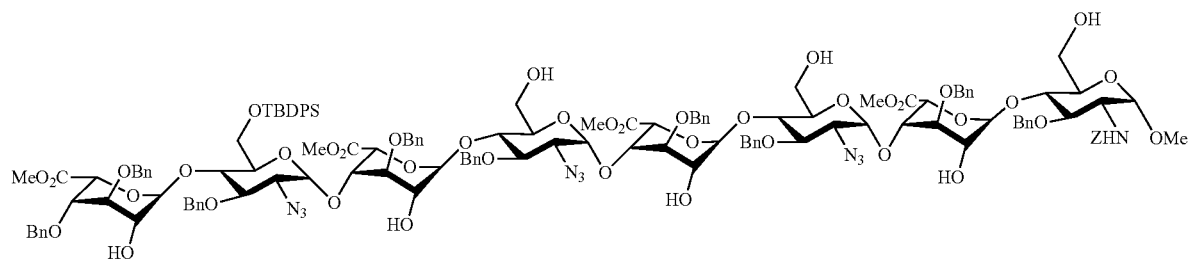
84
+

-continued
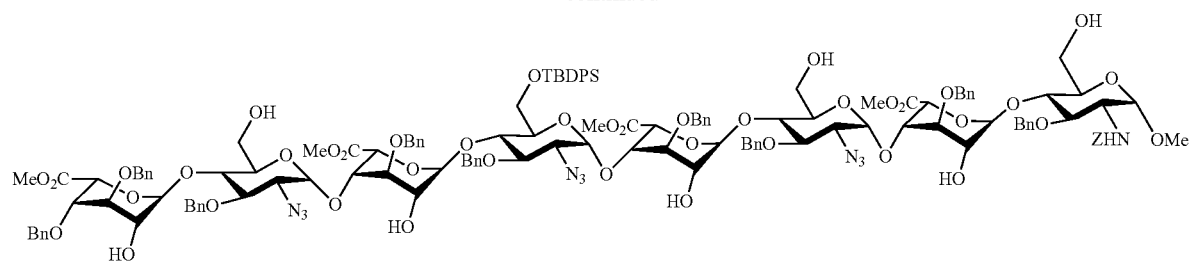
85
+
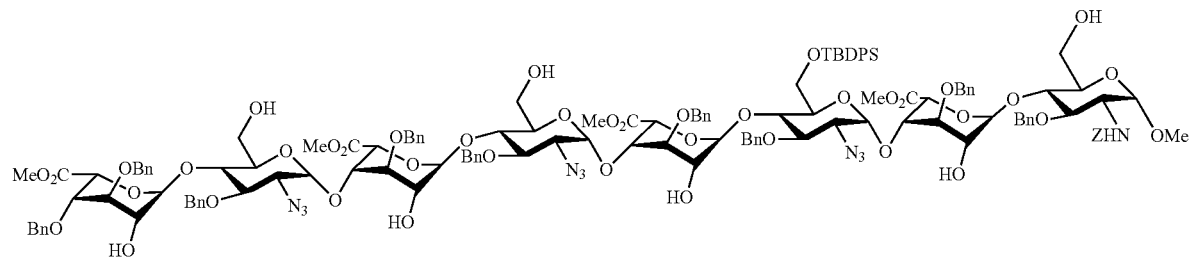
86
+
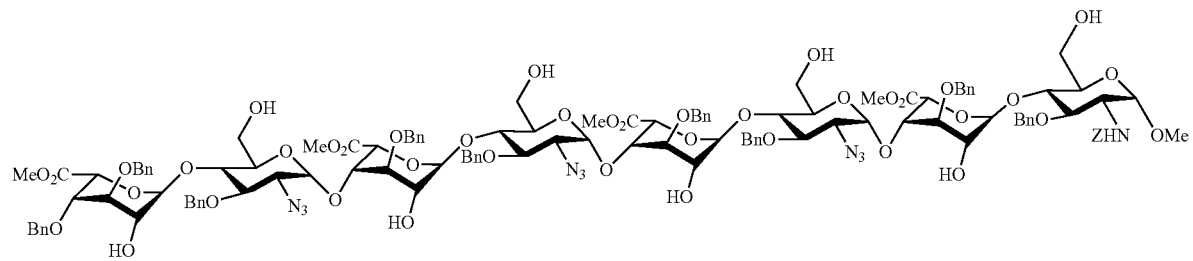
87

Methyl(methyl 3,4-di-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-[(methyl 3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)]$_2$-(methyl 3-O-benzyl-α-L-idopyranosyluronate)-(1→4)-3-O-benzyl-2-{[(benzyloxy)carbonyl]amino}-2-deoxy-α-D-glucopyranoside (80)

Methyl(methyl 3,4-di-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-3-O-benzyl-2-{[(benzyloxy)carbonyl]amino}-2-deoxy-α-D-glucopyranoside (81)

Methyl(methyl 3,4-di-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-α-L-idopyranosyluronate)-(1→4)-3-O-benzyl-2-{[(benzyloxy)carbonyl]amino}-2-deoxy-α-D-glucopyranoside (82)

Methyl(methyl 3,4-di-O-benzyl-α-L-idopyranosyluronate)-(1→4)-(2-azido-3-O-benzyl-2-deoxy-α-D-glucopyranosyl)-(1→4)-[(methyl 3-O-benzyl-α-L-idopyranosyluronate)-(1→4)-(2-azido-3-O-benzyl-2-deoxy-α-D-glucopyranosyl)-(1→4)]$_2$-(methyl 3-O-benzyl-α-L-idopyranosyluronate-(1→4)-3-O-benzyl-2-{[(benzyloxy)carbonyl]amino}-2-deoxy-α-D-glucopyranoside (87)

To a solution of compound 79 (373 mg, 0.11 mmol) in methanol (14 mL) is added ammonium fluoride (324 mg, 8.74 mmol). After stirring for 20 hours at room temperature, the reaction mixture is deposited on a column of Sephadex® LH20 gel (120×3 cm, 1/1 v/v dichloromethane/ethanol) followed by flash chromatography on a column of silica gel (1/0→7/3 v/v toluene/acetone) to give successively:
Compound 80 (58.8 mg)
TLC: Rf=0.63, silica gel, 65/35 v/v toluene/acetone
Compound 81 (44.4 mg)
TLC: Rf=0.53, silica gel, 65/35 v/v toluene/acetone
Compound 82 (37.7 mg)
TLC: Rf=0.45, silica gel, 65/35 v/v toluene/acetone
A mixture of compound 83 and of compound 84 (54.0 mg)
A mixture of compound 85 and of compound 86 (48.3 mg)
Compound 87 (26.6 mg)
TLC: Rf=0.14, silica gel, 65/35 v/v toluene/acetone Methyl(methyl 3,4-di-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-α-L-idopyranosyluronate)-(1→4)-3-O-benzyl-2-{[(benzyloxy)carbonyl]amino}-2-deoxy-α-D-glucopyranoside (83)

Methyl(methyl 3,4-di-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-[(methyl 3-O-benzyl-α-L-idopyranosyluronate)-(1→4)-(2-azido-3-O-benzyl-2-deoxy-α-D-glucopyranosyl)-(1→4)]$_2$-(methyl 3-O-benzyl-α-L-idopyranosyluronate)-(1→4)-3-O-benzyl-2-{[(benzyloxy)carbonyl]amino}-2-deoxy-α-D-glucopyranoside (84)

The mixture of compounds 83 and 84 (260 mg) is purified by flash chromatography on a column of silica gel (100/0→435/15 v/v toluene/methanol) to give compound 83 (27.8 mg).
TLC: Rf=0.22, silica gel, 85/15 v/v toluene/methanol
The remaining fractions are repurified by flash chromatography on a column of silica gel (100/0→97/3 v/v dichloromethane/methanol) to give compound 84 (45.3 mg).
TLC: Rf=0.13, silica gel, 85/15 v/v toluene/methanol Methyl(methyl 3,4-di-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-3-O-benzyl-2-{[(benzyloxy)carbonyl]-amino}-2-deoxy-α-D-glucopyranoside (85)

Methyl(methyl 3,4-di-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-α-L-idopyranosyluronate)-(1→4)-3-O-benzyl-2-{[(benzyloxy)carbonyl]-amino}-2-deoxy-α-D-glucopyranoside (86)

The mixture of compounds 85 and 86 (135 mg) is purified by HPLC chromatography on a column of C18 silica gel (Waters® Sunfire, 5 μm, 150×19 mm, 9/1 acetonitrile/water+0.1% trifluoroacetic acid) to give successively:
Compound 85 (32.6 mg), after size exclusion chromatography (Sephadex® LH20, 120×3 cm, 1/1 v/v dichloromethane/ethanol)
Mass: "ESI" method, negative mode: theoretical mass=2698.96; experimental mass: 2698.55±0.65 a.m.u.
Compound 86 (26.5 mg), after size exclusion chromatography (Sephadex® LH20, 120×3 cm, 1/1 v/v dichloromethane/ethanol)
Mass: "ESI" method, negative mode: theoretical mass=2698.96; experimental mass: 2698.95±1.05 a.m.u.

SCHEME 18: Preparation of the octasaccharide 91
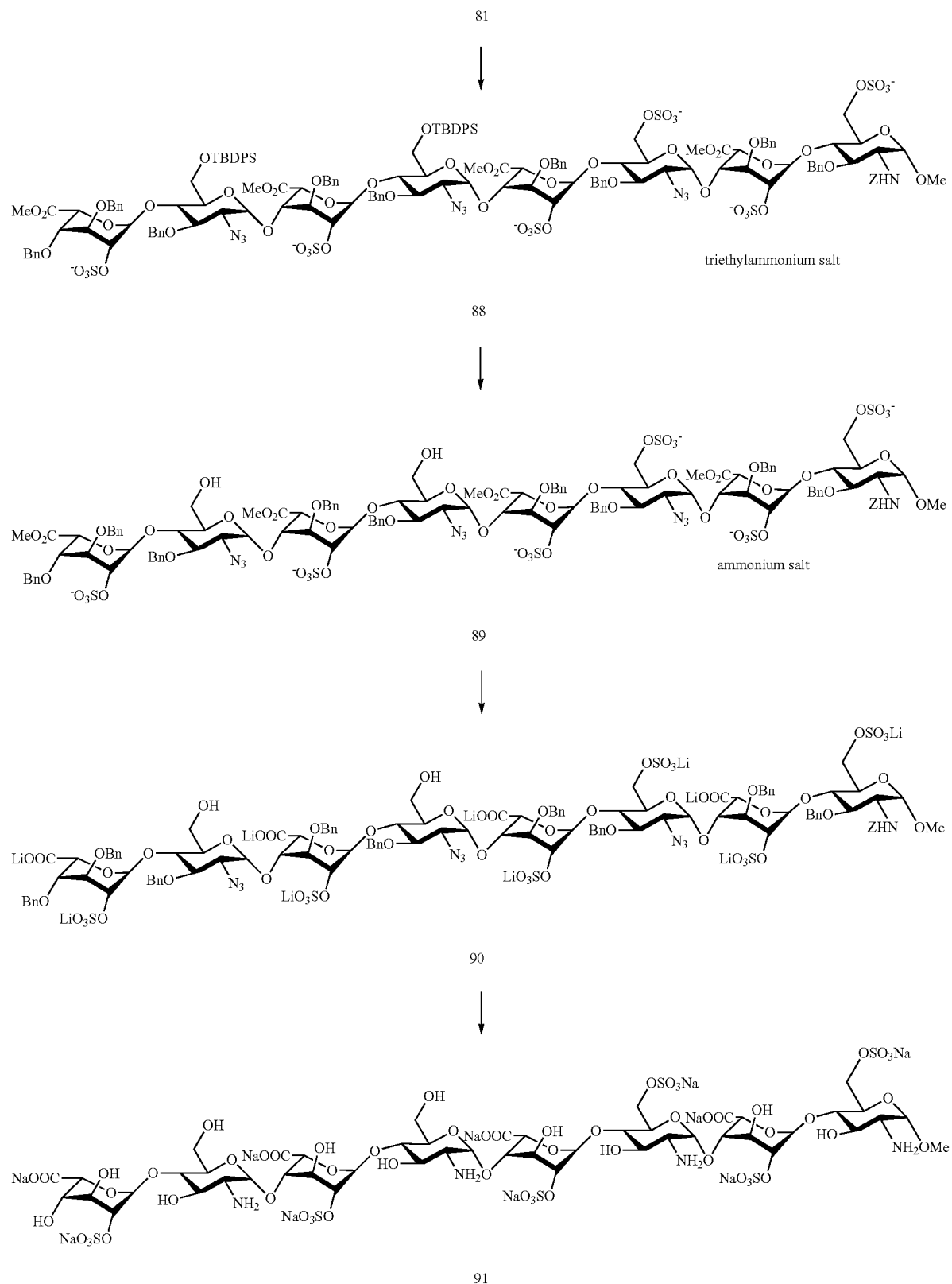

Methyl(methyl 3,4-di-O-benzyl-2-O-triethylammonium sulfonato-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-2-O-triethylammonium sulfonato-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-3-O-benzyl-2-{[(benzyloxy)carbonyl]amino}-2-deoxy-6-O-triethylammonium sulfonato-α-D-glucopyranoside (88)

Compound 81 (69 mg, 23.5 µmol) is treated according to the same procedure as that described for the preparation of compound 28 to give compound 88 (85.1 mg) after size exclusion chromatography (Sephadex® LH20, 120×3 cm, 1/1 v/v dichloromethane/ethanol).
TLC: Rf=0.62, silica gel, 17/9/2.2/5 v/v/v/v ethyl acetate/pyridine/acetic acid/water.

Methyl(methyl 3,4-di-O-benzyl-2-O-ammonium sulfonato-α-L-idopyranosyluronate)-(1→4)-(2-azido-3-O-benzyl-2-deoxy-α-D-glucopyranosyl)-(1→4)-(methyl 3-O-benzyl-2-O-ammonium sulfonato-α-L-idopyranosyluronate)-(1→4)-(2-azido-3-O-benzyl-2-deoxy-α-D-glucopyranosyl)-(1→4)-(methyl 3-O-benzyl-2-O-ammonium sulfonato-α-L-idopyranosyluronate)-(1→4)-(2-azido-3-O-benzyl-2-deoxy-6-O-ammonium sulfonato-α-D-glucopyranosyl)-(1→4)-(methyl 3-O-benzyl-2-O-ammonium sulfonato-α-L-idopyranosyluronate)-(1→4)-3-O-benzyl-2-{[(benzyloxy)carbonyl]amino}-2-deoxy-6-O-ammonium sulfonato-α-D-glucopyranoside (89)

To a solution of compound 88 (85.1 mg, 21.1 µmol) in methanol (2.7 mL) is added ammonium fluoride (31.3 mg, 0.846 mmol). After 48 hours at 55° C., the reaction mixture is deposited on a column of Sephadex® LH20 gel (95×2 cm) eluted with N,N-dimethylformamide to give compound 89 (64 mg).
$[\alpha]_D$ 19.4° (c 1.0; MeOH)

Methyl(lithium 3,4-di-O-benzyl-2-O-lithium sulfonato-α-L-idopyranosyluronate)-(1→4)-(2-azido-3-O-benzyl-2-deoxy-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-3-O-benzyl-2-{[(benzyloxy)carbonyl]amino}-2-deoxy-6-O-lithium sulfonato-α-D-glucopyranoside (90)

Compound 89 (63.3 mg; 17.8 µmol) is treated according to the same procedure as that described for the preparation of compound 29. Chromatography on a column of Sephadex® LH20 gel (120×3 cm, 50/50/1 v/v/v dichloromethane/ethanol/water) gives compound 90 (49.8 mg).
$[\alpha]_D$ 14.6° (c 1.0; MeOH)

Methyl(sodium 2-O-sodium sulfonato-α-L-idopyranosyluronate)-(1→4)-(2-amino-2-deoxy-α-D-glucopyranosyl)-(1→4)-(sodium 2-O-sodium sulfonato-α-L-idopyranosyluronate)-(1→4)-(2-amino-2-deoxy-α-D-glucopyranosyl)-(1→4)-(sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyluronate)-(1→4)-2-amino-2-deoxy-6-O-sodium sulfonato-α-D-glucopyranoside (91)

To a solution of compound 90 (7.6 mg; 2.6 µmol) in a 1/1 v/v tert-butanol/water mixture (516 µL) are successively added, at room temperature, ammonium formate (21.2 mg; 0.33 µmol) and 10% palladium-on-charcoal (49.4 mg). After stirring for 4 hours, the reaction medium is filtered (Millipore® LSWP 5 µm filter) and deposited on a column of Sephadex® G25-fine gel (95×2 cm) eluted with aqueous 0.2 M NaCl solution. The fractions containing the expected compound are combined and deposited on a column of Sephadex® G25-fine gel (95×2 cm) eluted with water. The crude product 91 thus obtained (5.5 mg) is used without further purification in the following step.

SCHEME 19: preparation of the octasaccharide 95

82
↓

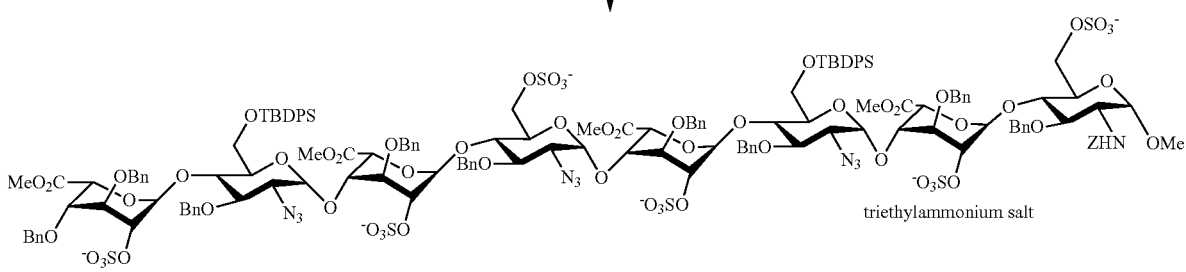

92

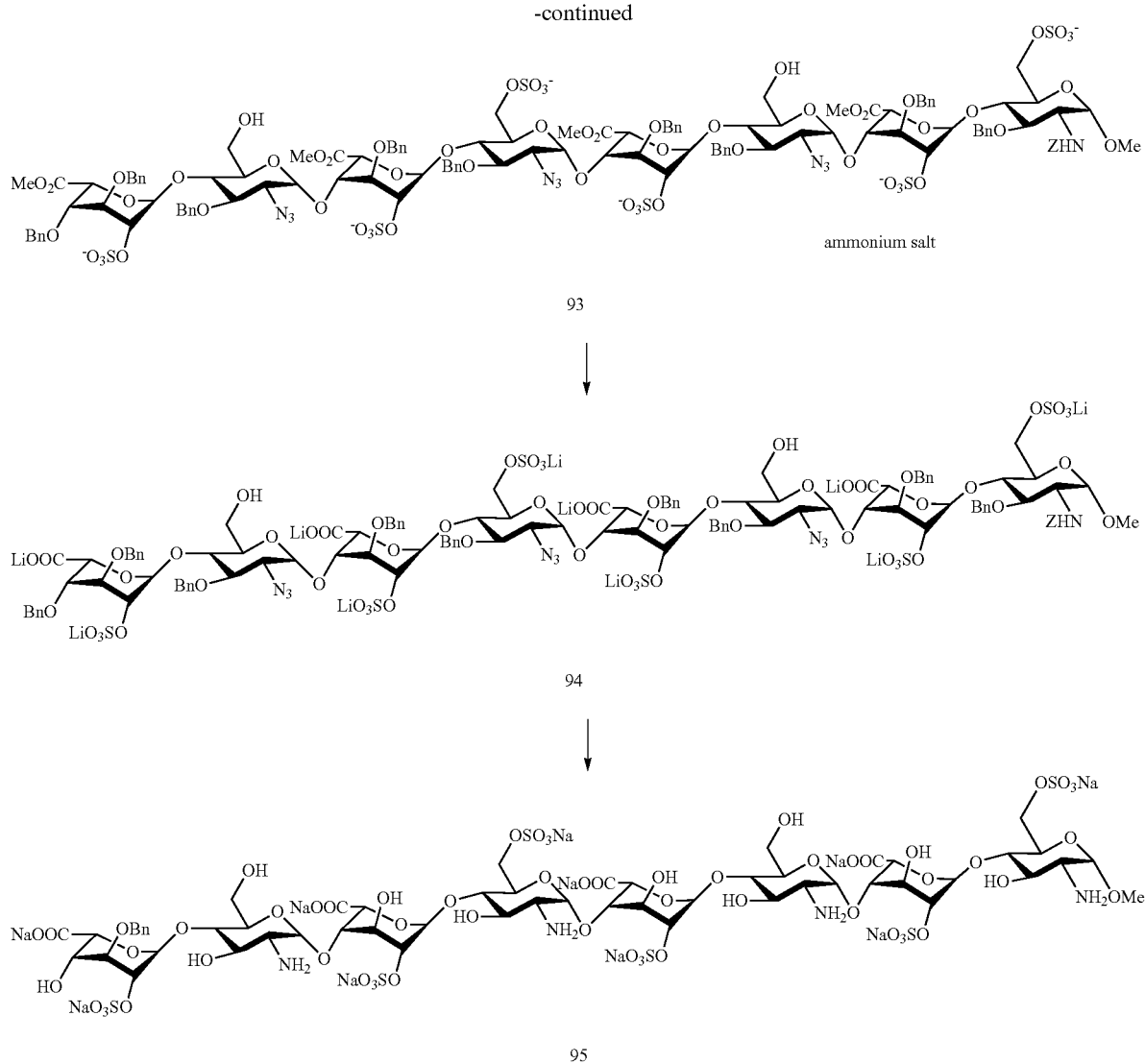

ammonium salt

93

94

95

Methyl(methyl 3,4-di-O-benzyl-2-O-triethylammonium sulfonato-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-(2-azido-3-O-benzyl-2-deoxy-6-O-tert-butyldiphenylsilyl-α-D-glucopyranosyl)-(1→4)-(methyl 3-O-benzyl-2-O-triethylammonium sulfonato-α-L-idopyranosyluronate)-(1→4)-3-O-benzyl-2-{[(benzyloxy)carbonyl]amino}-2-deoxy-6-O-triethylammonium sulfonato-α-D-glucopyranoside (92)

Compound 82 (16.5 mg, 5.6 μmol) is treated according to the same procedure as that described for the preparation of compound 28 to give compound 92 (21.5 mg) after chromatography on a column of Sephadex® LH20 gel (120×3 cm. 1/1 v/v dichloromethane/ethanol).

TLC: Rf=0.73, silica gel, 28/16/3.8/9 v/v/v/v ethyl acetate/pyridine/acetic acid/water.

Methyl(methyl 2-O-ammonium sulfonato-3,4-di-O-benzyl-α-L-idopyranosyluronate)-(1→4)-(2-azido-3-O-benzyl-2-deoxy-α-D-glucopyranosyl)-(1→4)-(methyl 2-O-ammonium sulfonato-3-O-benzyl-α-L-idopyranosyluronate)-(1→4)-(6-O-ammonium sulfonato 2-azido-3-O-benzyl-2-deoxy-α-D-glucopyranosyl)-(1→4)-(methyl 2-O-ammonium sulfonato-3-O-benzyl-α-L-idopyranosyluronate)-(1→4)-(2-azido-3-O-benzyl-2-deoxy-α-D-glucopyranosyl)-(1→4)-(methyl 2-O-ammonium sulfonato-3-O-benzyl-α-L-idopyranosyluronate)-(1→4)-6-O-ammonium sulfonato-3-O-benzyl-2-{[(benzyloxy)carbonyl]amino}-2-deoxy-α-D-glucopyranoside (93)

Compound 92 (21.5 mg, 5.3 μmol) is treated according to the same procedure as that described for the preparation of compound 89 to give compound 93 (21.5 mg) after size exclusion chromatography (Sephadex® LH20, 95×2 cm. N,N-dimethylformamide).

TLC: Rf=0.63, silica gel, 11/7/1.6/4 v/v/v/v ethyl acetate/pyridine/acetic acid/water.

Methyl(lithium 3,4-di-O-benzyl-2-O-lithium sulfonato-α-L-idopyranosyluronate)-(1→4)-(2-azido-3-O-benzyl-2-deoxy-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-α-D-glucopyranosyl)-(1→4)-(lithium 3-O-benzyl-2-O-lithium sulfonato-α-L-idopyranosyluronate)-(1→4)-3-O-benzyl-2-{[(benzyloxy)carbonyl]amino}-2-deoxy-6-O-lithium sulfonato-α-D-glucopyranoside (94)

Compound 93 (14.7 mg, 4.1 μmol) is treated according to the same procedure as that described for the preparation of compound 31 to give compound 94 (13.0 mg) after size exclusion chromatography (Sephadex® LH20, 95×2 cm, 50/50/1 v/v/v dichloromethane/ethanol/water).

TLC: Rf=0.56, silica gel, 28/16/3.8/9 v/v/v/v ethyl acetate/pyridine/acetic acid/water Methyl(sodium 2-O-sodium sulfonato-α-L-idopyranosyluronate)-(1→4)-(2-amino-2-deoxy-α-D-glucopyranosyl)-(1→4)-(sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyluronate)-(1→4)-(2-amino-2-deoxy-α-D-glucopyranosyl)-(1→4)-(sodium 2-O-sodium sulfonato-α-L-idopyranosyluronate)-(1→4)-2-amino-2-deoxy-6-O-sodium sulfonato-α-D-glucopyranoside (95)

To a solution of compound 94 (13 mg, 4.4 μmol) in a 1/1 v/v tert-butanol/water mixture (883 μL) are added ammonium formate (36 mg, 0.57 mmol) and 10% palladium-on-charcoal (34 mg). After stirring for 4 hours at room temperature, the reaction medium is filtered (Millipore® LSWP 5 μm filter) and concentrated to dryness. The residue is deposited on a column of Sephadex® G25-fine gel (95×2 cm) eluted with aqueous 0.2 M NaCl solution. The fractions containing the expected compound are combined and deposited on a column of Sephadex® G25-fine gel (95×2 cm) eluted with water. The crude product 95 thus obtained (2.5 mg) is used without further purification in the following step.

SCHEME 20: preparation of the octasaccharide 99

-continued

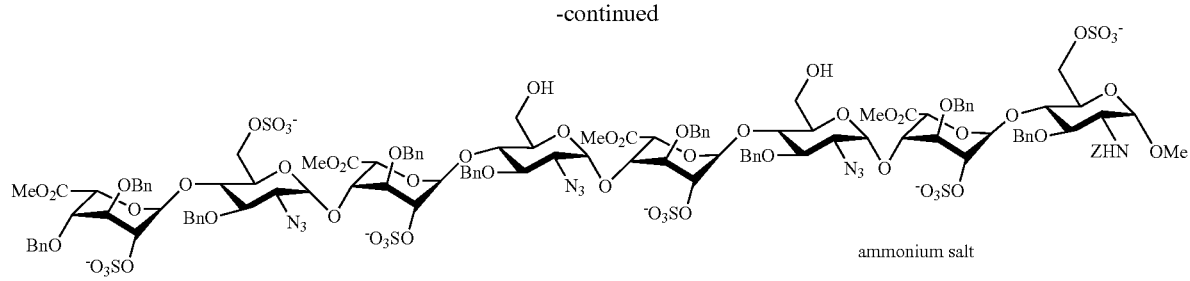

97

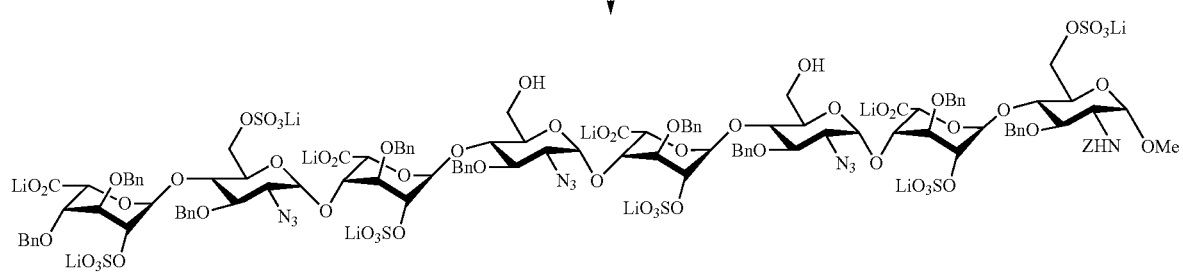

98

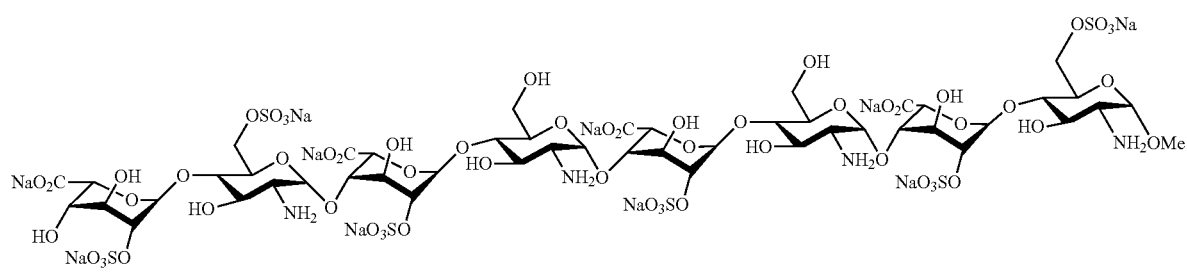

99

Methyl(methyl 3,4-di-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-[(methyl 3-O-benzyl-2-O-triethylammonium sulfonato-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-2-O-triethylammonium sulfonato-α-L-idopyranosyluronate-1→4)]₂-3-O-benzyl-2-{[(benzyloxy)carbonyl]amino}-2-deoxy-6-O-triethylammonium sulfonato-α-D-qlucopyranoside (96)

Compound 83 (35.1 mg, 12.0 µmol) is treated according to the same procedure as that described for the preparation of compound 28 to give compound 96 (46.3 mg) after chromatography on a column of Sephadex® LH20 gel (120×3 cm, 1/1 v/v dichloromethane/ethanol).

[α]$_D$ 111° (c 0.95; CH$_2$Cl$_2$)

Methyl(methyl 2-O-ammonium sulfonato-3,4-di-O-benzyl-α-L-idopyranosyluronate)-(1→4)-(6-O-ammonium sulfonato-azido-3-O-benzyl-2-deoxy-α-D-glucopyranosyl)-(1→4)-(methyl 2-O-ammonium sulfonato 3-O-benzyl-α-L-idopyranosyluronate)-(1→4)-(2-azido-3-O-benzyl-2-deoxy-α-D-glucopyranosyl)-(1→4)-(methyl 2-O-ammonium sulfonato-3-O-benzyl-α-L-idopyranosyluronate)-(1→4)-(2-azido-3-O-benzyl-2-deoxy-α-D-glucopyranosyl)-(1→4)-(methyl 2-O-ammonium sulfonato-3-O-benzyl-α-L-idopyranosyluronate)-(1→4)-6-O-ammonium sulfonato-3-O-benzyl-2-{[(benzyloxy)carbonyl]amino}-2-deoxy-α-D-glucopyranoside (97)

Compound 96 (45.0 mg, 11.2 µmol) is treated according to the same procedure as that described for the preparation of compound 89 to give compound 97 (30.8 mg) after chromatography on a column of Sephadex® LH20 gel (95×2 cm, N,N-dimethylformamide).

[α]$_D$ 14.7° (c 0.95; MeOH)

75

Methyl(lithium 3,4-di-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-[(lithium 3-O-benzyl-2-O-lithium sulfonato-α-L-idopyranosyluronate)-(1→4)-(2-azido-3-O-benzyl-2-deoxy-α-D-glucopyranosyl)-(1→4)]₂-(lithium methyl 3-O-benzyl-2-O-lithium sulfonato-α-L-idopyranosyluronate)-(1→4)-3-O-benzyl-2-{[(benzyloxy)carbonyl]amino}-2-deoxy-6-O-lithium sulfonato-α-D-glucopyranoside (98)

Compound 97 (27.1 mg, 7.6 μmol) is treated according to the same procedure as that described for the preparation of compound 29 to give compound 98 (20.7 mg) after chromatography on a column of Sephadex® LH20 gel (95×2 cm, 50/50/1 v/v/v dichloromethane/ethanol/water).

$[\alpha]_D$ 14.4° (c 1.01; MeOH)

76

Methyl(sodium 2-O-sodium sulfonato-α-L-idopyranosyluronate)-(1→4)-(2-amino-2-deoxy-6-O-sodium sulfonato-α-D-glucopyranosyl)-(1→4)-[(sodium 2-O-sodium sulfonato-α-L-idopyranosyluronate)-(1→4)-(2-amino-2-deoxy-α-D-glucopyranosyl)-(1→4)]₂-(sodium 2-O-sodium sulfonato-α-L-idopyranosyluronate)-(1→4)-2-amino-2-deoxy-6-O-sodium sulfonato-α-D-qlucopyranoside (99)

Compound 98 (17.5 mg, 5.9 μmol) is treated according to the same procedure as that described for the preparation of compound 91 to give compound 99 (9.5 mg).

Mass: "ESI" method, negative mode: theoretical mass=2081.38; experimental mass: 1993.28±0.14 a.m.u. (iduronic acids observed in COOH form).

SCHEME 21: preparation of the octasaccharide 104

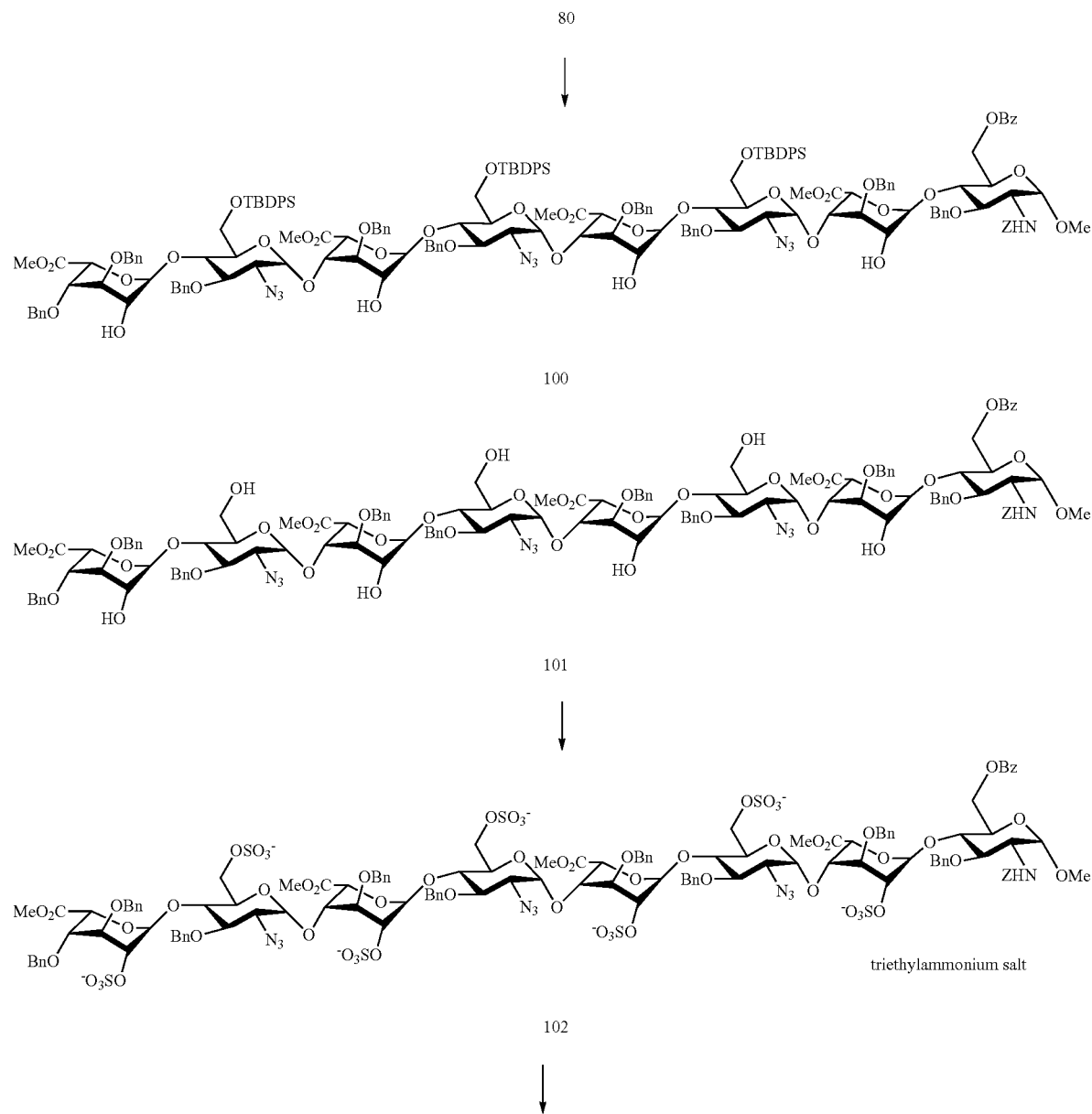

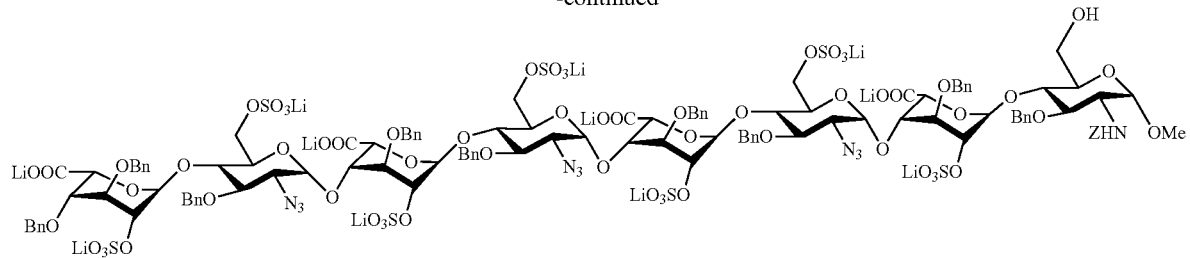

103

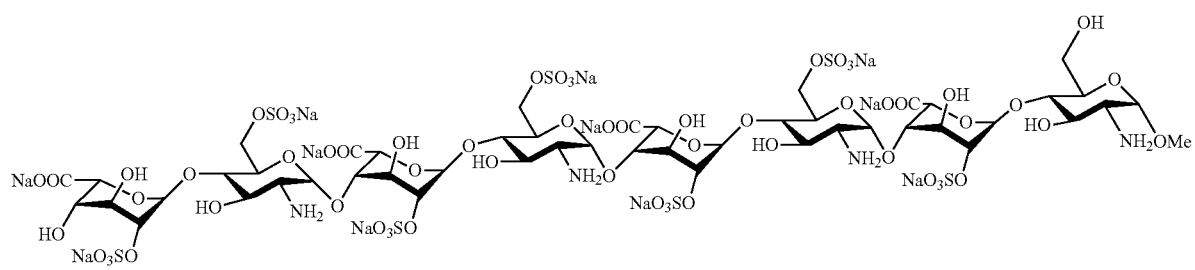

104

Methyl(methyl 3,4-di-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-[(methyl 3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)]₂:(methyl 3-O-benzyl-α-L-idopyranosyluronate)-(1→4)-6-O-benzoyl-3-O-benzyl-2-{[(benzyloxy)-carbonyl]amino}-2-deoxy-α-D-glucopyranoside (100)

A solution of compound 80 (355 mg, 0.117 mmol), benzoic anhydride (75.8 mg, 0.335 mmol) and triethylamine (47.3 µL, 0.335 mmol) in 1,2-dichloroethane (5.6 mL) is stirred at 60° C. for 24 hours and then for 64 hours at room temperature. The reaction mixture is deposited on a column of Sephadex® LH20 gel (120×3 cm) eluted with a 1/1 v/v dichloromethane/ethanol mixture, followed by flash chromatography on a column of silica gel (100/0→435/15 v/v toluene/acetone) to give compound 100 (193.2 mg).

TLC: Rf=0.38, silica gel, 2/1 v/v cyclohexane/ethyl acetate

Methyl(methyl 3,4-di-O-benzyl-α-L-idopyranosyluronate)-(1→4)-(2-azido-3-O-benzyl-2-deoxy-α-D-glucopyranosyl)-(1→4)-[(methyl 3-O-benzyl-α-L-idopyranosyluronate)-(1→4)-(2-azido-3-O-benzyl-2-deoxy-α-D-glucopyranosyl)-(1→4)]₂-(methyl 3-O-benzyl-α-L-idopyranosyluronate-(1→4)-6-O-benzoyl 3-O-benzyl-2-{[(benzyloxy)carbonyl]amino}-2-deoxy-α-D-glucopyranoside (101)

Compound 100 (60.0 mg, 0.018 mmol) is treated according to the same procedure as that described for the preparation of compound 89 to give compound 101 (46.1 mg) after chromatography on a column of Sephadex® LH20 gel (120×3 cm, 1/1 v/v dichloromethane/ethanol).

Mass: "ESI" method, negative mode: theoretical mass=2564.66; experimental mass: 2563.66±0.19 a.m.u.

Methyl(methyl 3,4-di-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-[(methyl 3-O-benzyl-2-O-triethylammonium sulfonato-α-L-idopyranosyluronate)-(1→4)-(2-azido-3-O-benzyl-2-deoxy-6-O-triethlammonium sulfonato-α-D-glucopyranosyl)-(1→4)]₂-(methyl 3-O-benzyl-2-O-triethylammonium sulfonato-α-L-idopyranosyluronate)-(1→4)-6-O-benzoyl-3-O-benzyl-2-{[(benzyloxy)carbonyl]amino}-2-deoxy-α-D-glucopyranoside (102)

Compound 101 (42.9 mg, 0.016 mmol) is treated according to the same procedure as that described for the preparation of compound 28 to give compound 102 (28.7 mg) after chromatography on a column of Sephadex® LH20 gel (120×3 cm, 1/1 v/v dichloromethane/ethanol) and then flash chromatography on a column of C₁₈ silica gel (40-60 µm; A: methanol, 5% water, 23 mM ammonium acetate; B: acetonitrile, 45% methanol, 5% water, 17 mM ammonium acetate; A→B 100/0→70/30) followed by desalting on a Sephadex® LH20 column (95×2 cm, 50/50/1 v/v/v dichloromethane/ethanol/water).

Methyl(lithium 3,4-di-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-[(lithium 3-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)]$_2$-lithium 3-O-benzyl-2-O-lithium sulfonato-α-L-idopyranosyluronate)-(1→4)-3-O-benzyl-2-{[(benzyloxy)carbonyl]amino}-2-deoxy-α-D-glucopyranoside (103)

Compound 102 (28.7 mg, 7.5 μmol) is treated according to the same procedure as that described for the preparation of compound 29 to give crude compound 103 (17.3 mg).

Methyl(sodium 2-O-sodium sulfonato-α-L-idopyranosyluronate)-(1→4)-(2-amino-2-deoxy-6-O-sodium sulfonato-α-D-glucopyranosyl)-(1→4)-[(sodium 2-O-sodium sulfonato-α-L-idopyranosyluronate)-(1→4)-(2-amino-2-deoxy-6-O-sodium sulfonato-α-D-glucopyranosyl)-(1→4)]$_2$-sodium 2-O-sodium sulfonato-α-L-idopyranosyluronate)-(1→4)-2-amino-2-deoxy-α-D-glucopyranoside (104)

Compound 103 (17.3 mg, 5.7 μmol) is treated according to the same procedure as that described for the preparation of compound 91. The crude compound 104 thus obtained is again saponified. To a solution of crude compound 104 in a 1/1 v/v tetrahydrofuran/methanol mixture (506 μL) is added, at 0° C., a 0.7 M solution of lithium hydroxide in water (202 μL, qs a final concentration of 0.2 M). After 1 hour at 0° C. and then 16 hours at room temperature, the reaction medium is chromatographed on an exclusion column (Sephadex® G25-fine, 95×2 cm, 0.2 M NaCl and then Sephadex® G25-fine, 95×2 cm, water) to give compound 104 (6.5 mg).

$^1$H NMR [600 MHz] (D$_2$O) δ of the anomeric protons: 5.45; 5.44; 5.43; 5.26; 5.25; 5.24; 5.18; 4.98 ppm SCHEME 22: preparation of the octasaccharide 108

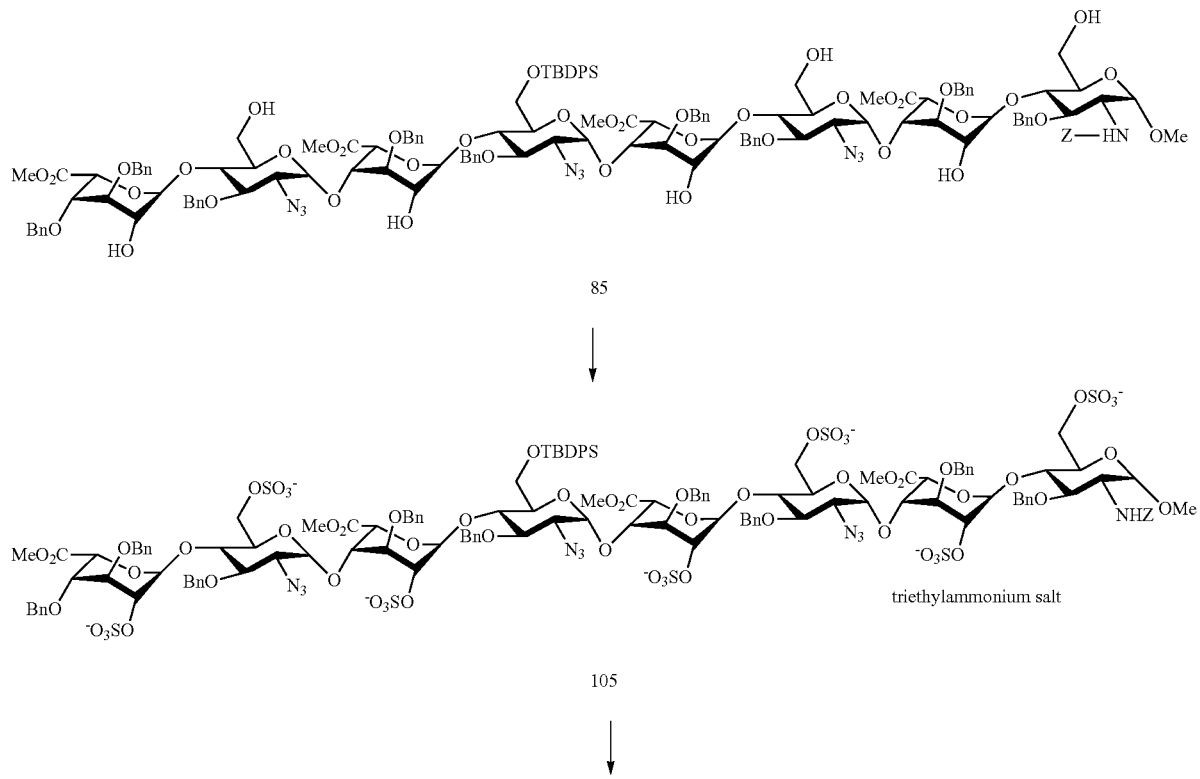

-continued

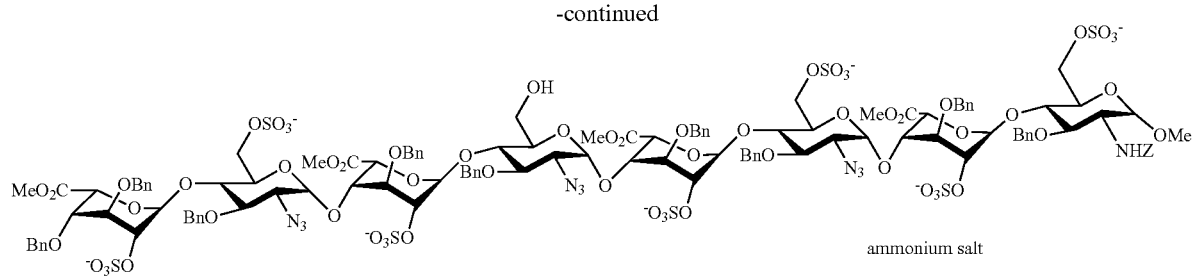

106

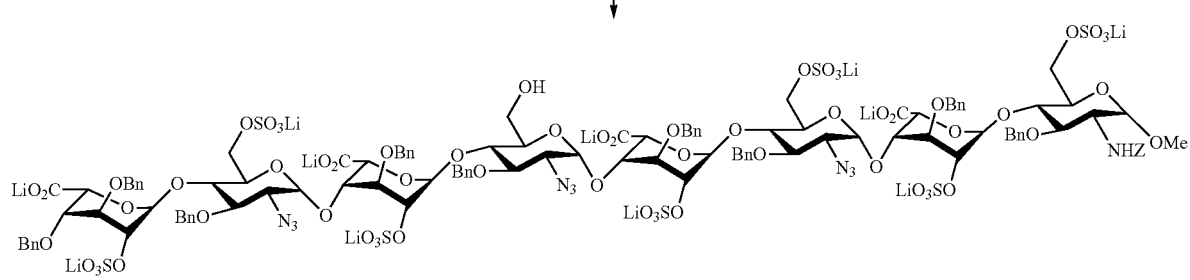

107

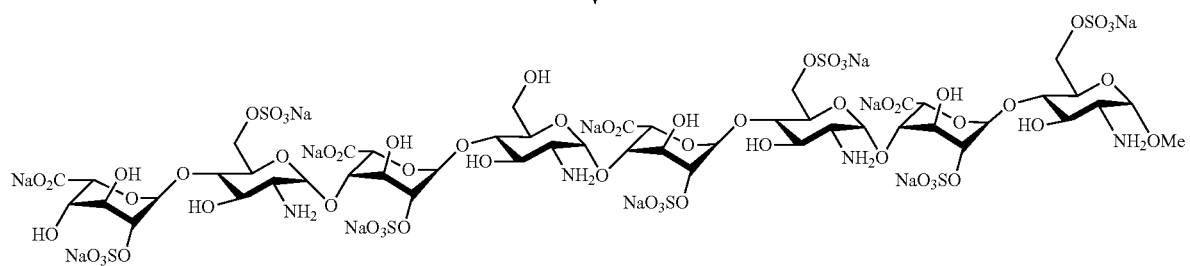

108

Methyl(methyl 3,4-di-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-(2-azido-3-O-benzyl-6-O-tert-butyldiphenylsilyle-2-deoxy-α-D-glucopyranosyl)-(1→4)-(methyl 3-O-benzyl-2-O-triethylammoniumsulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-3-O-benzyl-2-deoxy-2-[(benzyloxy)carbonyl]amino-6-O-triethylammonium sulfonato-α-D-glucopyranoside (105)

Compound 85 (31.4 mg, 11.6 μmol) is treated according to the same procedure as that described for the preparation of compound 28 to give compound 105 (40.2 mg) after chromatography on a column of Sephadex® LH20 gel (120×3 cm, 50/50/1 v/v/v dichloromethane/ethanol/water).

Methyl(methyl 2-O-ammonium sulfonato-3,4-di-O-benzyl-α-L-idopyranosyluronate)-(1→4)-(6-O-ammonium sulfonato-2-azido-3-O-benzyl-2-deoxy-α-D-glucopyranosyl)-(1→4)-(methyl 2-O-ammonium sulfonato-3-O-benzyl-α-L-idopyranosyluronate)-(1→4)-(2-azido-3-O-benzyl-2-deoxy-α-D-glucopyranosyl)-(1→4)-(methyl 2-O-ammonium sulfonato-3-O-benzyl-α-L-idopyranosyluronate)-(1→4)-(6-O-ammonium sulfonato-2-azido-3-O-benzyl-2-deoxy-α-D-glucopyranosyl)-(1→4)-(methyl 2-O-ammonium sulfonato-3-O-benzyl-α-L-idopyranosyluronate)-(1→4)-6-O-ammonium sulfonato-3-O-benzyl-2-[(benzyloxy)carbonyl]amino-2-deoxy-α-D-glucopyranoside (106)

Compound 105 (38.4 mg, 9.68 μmol) is treated according to the same procedure as that described for the preparation of compound 89 to give compound 106 (28.4 mg) after chromatography on a column of Sephadex® LH20 gel (95×2 cm, N,N-dimethylformamide).

Rf=0.21 (28/16/3.8/9 EtOAc/pyridine/AcOH/H₂O).

Methyl(lithium 3,4-di-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-3-O-benzyl-2-deoxy-2-[(benzyloxy)carbonyl]amino-6-O-lithium sulfonato-α-D-qlucopyranoside (107)

Compound 106 (28.4 mg, 7.62 μmol) is treated according to the same procedure as that described for the preparation of compound 89 to give compound 107 (28.0 mg) after chromatography on a column of Sephadex® LH20 gel (95×2 cm, 50/50/1 v/v/v dichloromethane/ethanol/water).
Rf=0.12 (28/16/3.8/9 EtOAc/pyridine/AcOH/H$_2$O).

Methyl(sodium 2-O-sodium sulfonato-α-L-idopyranosyluronate)-(1-4)-(2-amino-2-deoxy-6-O-sodium sulfonato-α-D-glucopyranosyl)-(1-4)-(sodium 2-O-sodium sulfonato-α-L-idopyranosyluronate)-(1-4)-(2-amino-2-deoxy-α-D-glucopyranosyl)-(1-4)-(sodium 2-O-sodium sulfonato-α-L-idopyranosyluronate)-(1-4)-(2-amino-2-deoxy-6-O-sodium sulfonato-α-D-glucopyranosyl)-(1-4)-(sodium 2-O-sodium sulfonato-α-L-idopyranosyluronate)-(1-4)-2-amino-2-deoxy-6-O-sodium sulfonato-α-D-glucopyranoside (108)

Compound 107 (5.8 mg, 2.85 μmol) is treated according to the same procedure as that described for the preparation of compound 91 to give compound 108 (2.5 mg), which is used without further purification in the following step.

$^1$H NMR [600 MHz] (D$_2$O) 6 of the anomeric protons: 5.45; 5.44; 5.42; 5.26; 5.25; 5.24; 5.17; 5.03 ppm SCHEME 23: preparation of the octasaccharide 111

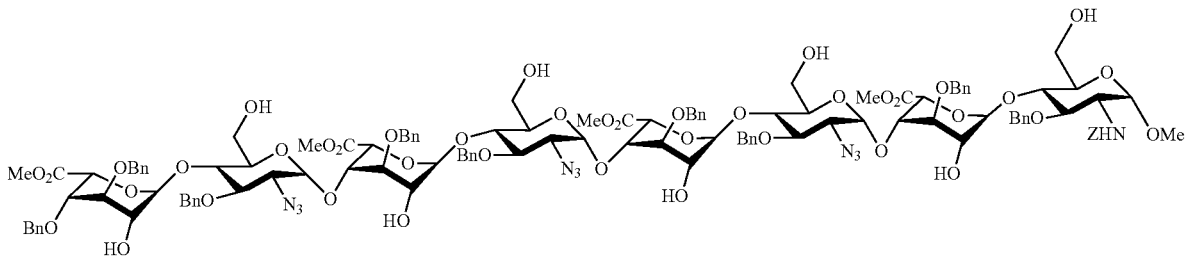

87

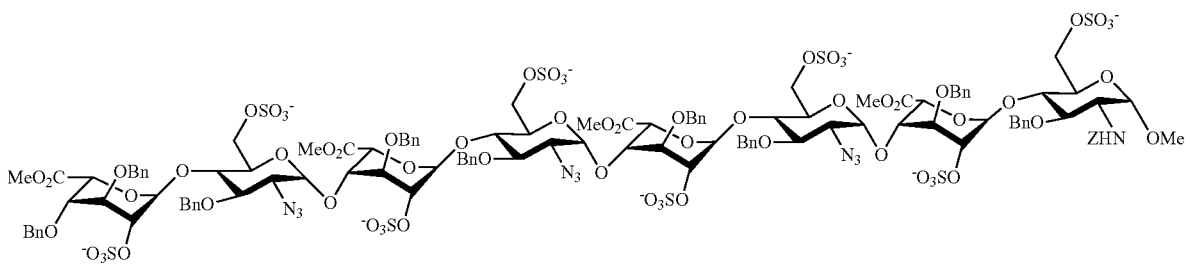

109

-continued

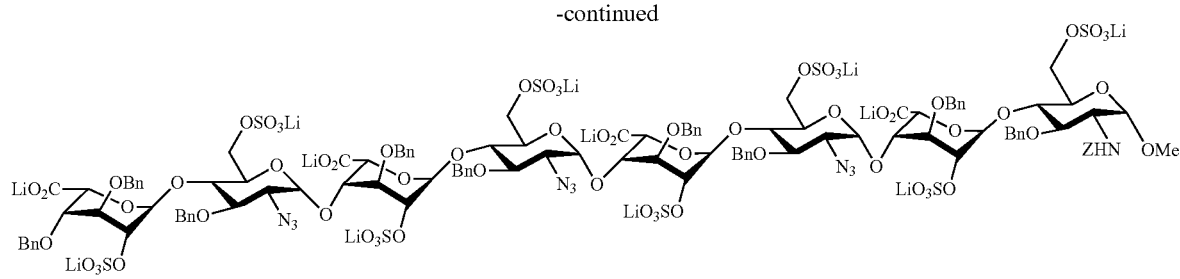

110

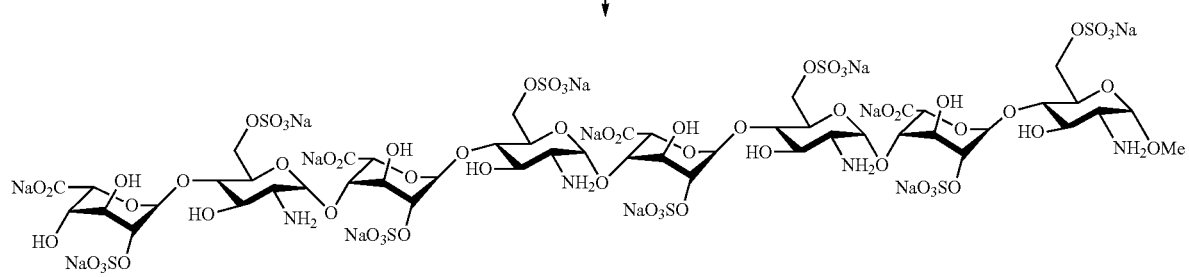

111

Methyl(methyl 3,4-di-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-[(1→4)-(methyl 3-O-benzyl-2-O-triethylammonium sulfonato-α-L-idopyranosyluronate)-(1→4)-(2-azido-3-O-benzyl-2-deoxy-6-O-triethlammonium sulfonato-α-D-glucopyranosyl)]$_2$-(1→4)-(methyl 3-O-benzyl-2-O-triethylammonium sulfonato-α-L-idopyranosyluronate)-(1→4)-3-O-benzyl-2-benzyloxycarbonylamino-2-deoxy-6-O-triethylammonium sulfonato-α-D-qlucopyranoside (109)

Compound 87 (37.0 mg, 0.15 mmol) is dried by co-distillation of N,N-dimethylformamide (3×1.4 mL) and is then dissolved in N,N-dimethylformamide (1.4 mL). To this solution is added the sulfur trioxide-triethylamine complex (109 mg; 6.01 mmol). The mixture is stirred for 16 hours at 55° C. protected from light and the excess reagent is then destroyed with methanol (25 µL). The reaction medium is deposited on a column of Sephadex® LH20 (120×3 cm) eluted with a 1/1 dichloromethane/ethanol mixture to give compound 109 (59.8 mg).
Rf=0.26, silica gel, 28/16/3.8/9 ethyl acetate/pyridine/acetic acid/water.

Methyl(lithium 3,4-di-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-[(1→4)-(lithium 3-O-benzyl-2-O-lithium sulfonato-α-L-idopyranosyluronate)-(1→4)-(2-azido-3-O-benzyl-2-deoxy-6-O-lithium sulfonato-α-D-glucopyranos)]$_2$-(1→4)-lithium 3-O-benzyl-2-O-lithium sulfonato-α-L-idopyranosyluronate)-(1→4)-3-O-benzyl-2-benzyloxycarbonylamino-2-deoxy-6-O-lithium sulfonato-α-D-glucopyranoside (110)

To a solution of compound 109 (57.3 mg, 13.7 µmol) in a 1/1 v/v tetrahydrofuran/methanol mixture (2.2 mL) is added, at 0° C., a 0.7 M solution of lithium hydroxide in water (0.88 mL; qs final concentration of 0.2 M). After 1 hour at 0° C. and then 16 hours at room temperature, the reaction medium is deposited on a column of Sephadex® LH20 (120×3 cm) eluted with a 50/50/1 v/v/v dichloromethane/ethanol/water mixture to give compound 110 (38.1 mg).
[α]$_D$ 13.1° (c 1.0; MeOH)

Methyl(sodium 2-O-sodium sulfonato-α-L-idopyranosyluronate)-(1→4)-(2-amino-2-deoxy-6-O-sodium sulfonato-α-D-glucopyranosyl)-[(1→4)-(sodium 2-O-sodium sulfonato-α-L-idopyranosyluronate)-(1→4)-(2-amino-2-deoxy-6-O-sodium sulfonato-α-D-glucopyranos)]$_2$-(1→4)-sodium 2-O-sodium sulfonato-α-L-idopyranosyluronate)-(1→4)-2-amino-2-deoxy-6-O-sodium sulfonato-α-D-glucopyranoside (111)

To a solution of compound 110 (40 mg, 12.8 µmol) in a 1/1 v/v tert-butanol/water mixture (2.6 mL) are added ammonium formate (105 mg, 1.67 mmol) and 10% palladium-on-charcoal (260 mg). After stirring for 4 hours at room temperature, the reaction medium is filtered (Millipore® LSWP 5 µm filter) and concentrated to dryness. The residue is deposited on a column of Sephadex® G25-fine gel (95×2 cm) eluted with aqueous 0.2 M NaCl solution. The fractions containing the expected compound are combined and deposited on a column of Sephadex® G25-fine gel (95×2 cm) eluted with water. The crude product 111 thus obtained (14.7 mg) is used without further purification in the following step.
Mass: "ESI" method, negative mode: theoretical mass=2285.47; experimental mass: 2197.20±0.34 a.m.u. (iduronic acids observed in COOH form).

EXAMPLES OF COMPOUNDS ACCORDING TO THE INVENTION

Example 1

Methyl(sodium 4-O-propyl-2-O-sodium sulfonato-α-L-idopyranosyluronate)-(1→4)-(2-deoxy-6-O-sodium sulfonato-2-sodium (sulfonatoamino)-α-D-glucopyranosyl)-(1→4)-[(sodium 2-O-sodium sulfonato-α-L-idopyranosyluronate)-(1→4)-(2-deoxy-6-O-sodium sulfonato-2-sodium sulfonatoamino)-α-D-glucopyranosyl-(1→4)]₂-(sodium 2-O-sodium sulfonato-α-L-idopyranosyluronate)-(1→4)-2-deoxy-6-O-sodium sulfonato-2-sodium (sulfonatoamino)-α-D-glucopyranoside (compound 1)

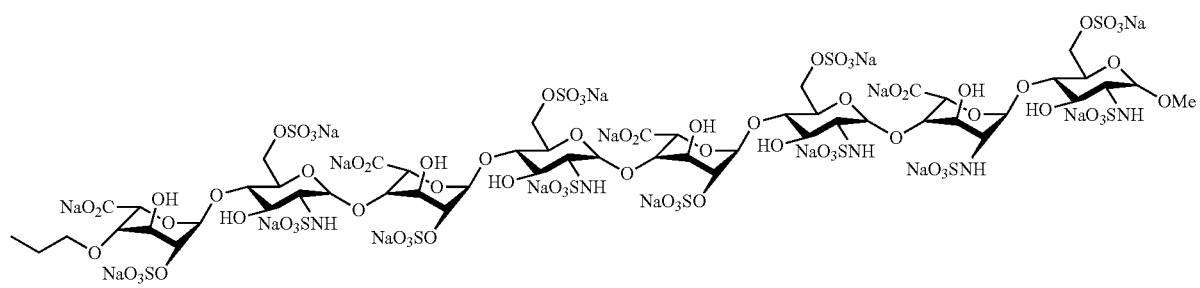

To a freshly prepared solution of compound 30 (180 mg, 0.077 mmol) in saturated aqueous sodium hydrogen carbonate solution (15 mL, 100 mL/mmol) are added, at 0° C. and under an argon atmosphere, solid sodium hydrogen carbonate (1.17 g, 13.9 mmol) and then the pyridine-sulfur trioxide complex (985 mg, 6.19 mmol) portionwise over 30 minutes. After 16 hours at room temperature, the reaction mixture is deposited on a column of Sephadex® G25-fine gel (90×3 cm) eluted with aqueous 0.2 M NaCl solution. The fractions containing the expected compound are combined and deposited on a column of Sephadex® G25-fine gel (90×3 cm) eluted with water. After concentrating the fractions containing the expected compound, 200 mg of compound 1 are obtained.

$^1$H NMR [600 MHz] (D$_2$O) δ of the anomeric protons: 5.45; 5.42 (2H); 5.22; 5.21; 5.20; 5.18; 5.03 ppm.

Mass: "ESI" method, negative mode: theoretical mass=2735.72; experimental mass: 2734 a.m.u.

Example 2

Methyl(sodium 4-O-propyl-2-O-sodium sulfonato-α-L-idopyranosyluronate)-(1→4)-(2-deoxy-6-O-sodium sulfonato-2-sodium (sulfonatoamino)-α-D-glucopyranosyl)-(1→4)-[(sodium 2-O-sodium sulfonato-α-L-idopyranosyluronate)-(1→4)-(2-deoxy-6-O-sodium sulfonato-2-sodium sulfonatoamino)-α-D-glucopyranosyl-(1→4)]₃-sodium 2-O-sodium sulfonato-α-L-idopyranosyluronate)-(1→4)-2-deoxy-6-O-sodium sulfonato-2-sodium (sulfonatoamino)-α-D-glucopyranoside (compound 2)

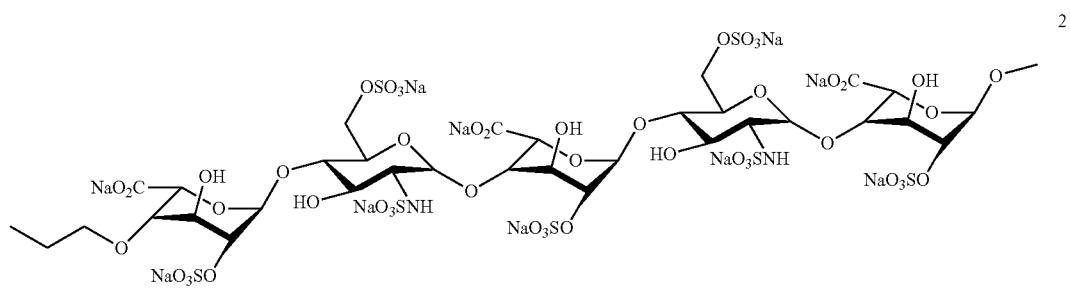

-continued

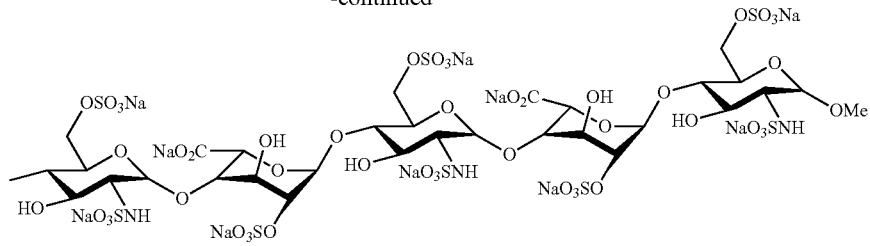

Compound 37 (29.5 mg, 11.56 µmol) is treated according to the same procedure as that described for the preparation of Example 1 to give compound 2 (7.4 mg) after purification by ion-exchange chromatography (SAX column, conditions: 0.5 mL/min, A: H$_2$O, B: 2 M NaCl, gradient 30% of B to 90% over 30 min) followed by chromatography on a column of Sephadex® G25-fine gel (54×1.7 cm, water).

$^1$H NMR [600 MHz] (D$_2$O) δ of the anomeric protons: 5.45; 5.42; 5.41 (2H); 5.22; 5.21 (2H); 5.20; 5.18; 5.03 ppm.

Mass: "ESI" method, negative mode: theoretical mass=3401.12; experimental mass: 3400.40±0.76 a.m.u.

Example 3

Sodium [methyl(sodium 2-O-sodium sulfonato-α-L-idopyranosyluronate)-(1→4)-(2-deoxy-6-O-sodium sulfonato-2-sodium (sulfonatoamino)-α-D-glucopyranosyl)-(1→4)-[(sodium 2-O-sodium sulfonato-α-L-idopyranosyluronate)-(1→4)-(2-deoxy-6-O-sodium sulfonato-2-sodium sulfonatoamino)-α-D-glucopyranos)-(1→4)]$_2$-2-O-sodium sulfonato-α-L-idopyranoside]uronate (compound 3)

3

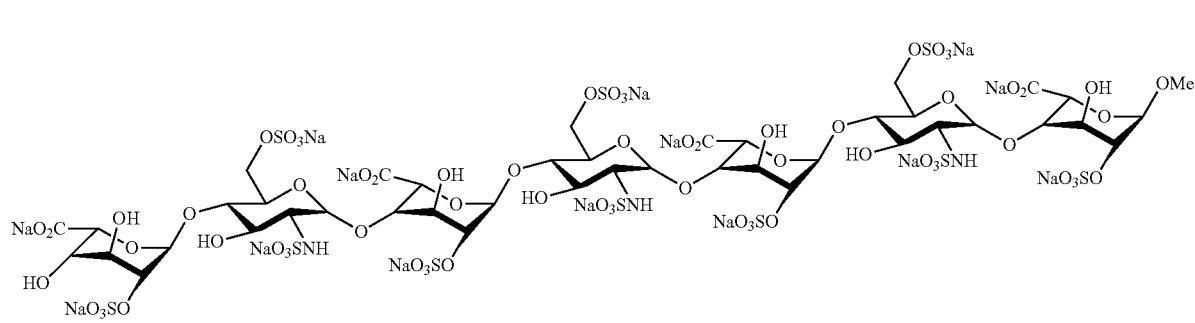

Crude compound 55 (48.7 mg) is treated according to the same procedure as that described for the preparation of Example 1 to give compound 3 (37.6 mg).

$^1$H NMR [600 MHz] (D$_2$O) δ of the anomeric protons: 5.43 (2H); 5.35; 5.25; 5.24; 5.19; 5.18; 5.09 ppm.

Example 4

Methyl(sodium 2-O-sodium sulfonato-α-L-idopyranosyluronate)-(1→4)-(2-deoxy-2-sodium (sulfonatoamino)-α-D-glucopyranosyl)-(1→4)-(sodium 2-O-sodium sulfonato-α-L-idopyranosyluronate)-(1→4)-(2-deoxy-2-sodium (sulfonatoamino)-α-D-glucopyranosyl)-(1→4)-(sodium 2-O-sodium sulfonato-α-L-idopyranosyluronate)-(1→4)-(2-deoxy-6-O-sodium sulfonato-2-sodium (sulfonatoamino)-α-D-glucopyranosyl)-(1→4)-(sodium 2-O-sodium sulfonato-α-L-idopyranosyluronate)-(1→4)-2-deoxy-6-O-sodium sulfonato-2-sodium (sulfonatoamino)-α-D-glucopyranoside (compound 4)

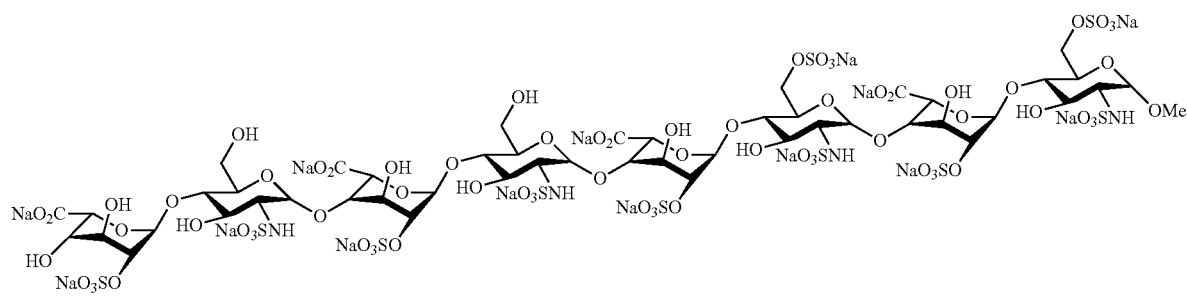

4

Compound 91 (5.5 mg, 2.64 µmol) is treated according to the same procedure as that described for the preparation of Example 1 to give compound 4 (4.5 mg).

$^1$H NMR [600 MHz] (D$_2$O) δ of the anomeric protons: 5.44; 5.40; 5.31; 5.25; 5.24; 5.22; 5.16; 5.03 ppm.

Mass: "ESI" method, negative mode: theoretical mass=2489.55; experimental mass: 2465.63±0.64 a.m.u.

Example 5

Methyl(sodium 2-O-sodium sulfonato-α-L-idopyranosyluronate)-(1→4)-(2-deoxy-2-sodium (sulfonatoamino)-α-D-glucopyranosyl)-(1→4)-(sodium 2-O-sodium sulfonato-α-L-idopyranosyluronate)-(1→4)-(2-deoxy-6-O-sodium sulfonato-2-sodium (sulfonatoamino)-α-D-glucopyranosyl)-(1→4)-(sodium 2-O-sodium sulfonato-α-L-idopyranosyluronate)-(1→4)-(2-deoxy-2-sodium (sulfonatoamino)-α-D-glucopyranosyl)-(1→4)-(sodium 2-O-sodium sulfonato-α-L-idopyranosyluronate)-(1→4)-2-deoxy-6-O-sodium sulfonato-2-sodium (sulfonatoamino)-α-D-glucopyranoside (compound 5)

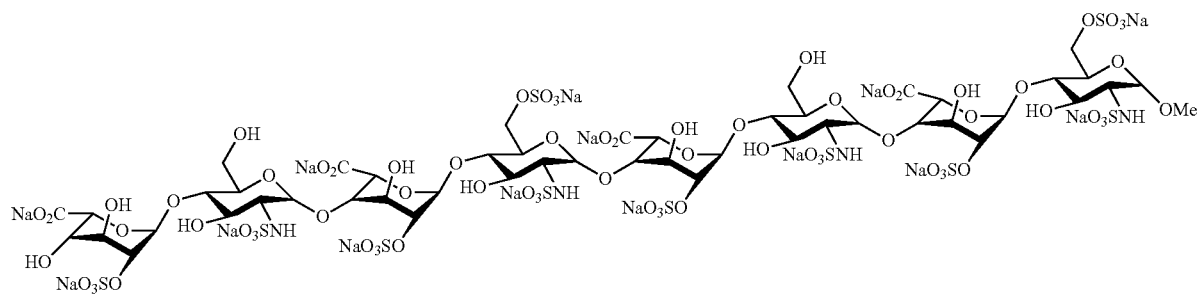

5

Compound 95 (2.5 mg, 1.2 μmol) is treated according to the same procedure as that described for the preparation of Example 1 to give compound 5 (1.9 mg).

$^1$H NMR [600 MHz] (D$_2$O) δ of the anomeric protons: 5.45; 5.43; 5.33; 5.25; 5.23; 5.21; 5.16; 5.05 ppm.

Example 6

Methyl(sodium 2-O-sodium sulfonato-α-L-idopyranosyluronate)-(1→4)-(2-deoxy-6-O-sodium sulfonato-2-sodium (sulfonatoamino)-α-D-glucopyranosyl)-(1→4)-(sodium 2-O-sodium sulfonato-α-L-idopyranosyluronate)-(1→4)-(2-deoxy-2-sodium (sulfonatoamino)-α-D-glucopyranosyl)-(1→4)-(sodium 2-O-sodium sulfonato-α-L-idopyranosyluronate)-(1→4)-(2-deoxy-2-sodium (sulfonatoamino)-α-D-glucopyranosyl)-(1→4)-(sodium 2-O-sodium sulfonato-α-L-idopyranosyluronate)-(1→4)-2-deoxy-6-O-sodium sulfonato-2-sodium (sulfonatoamino)-α-D-glucopyranoside (compound 6)

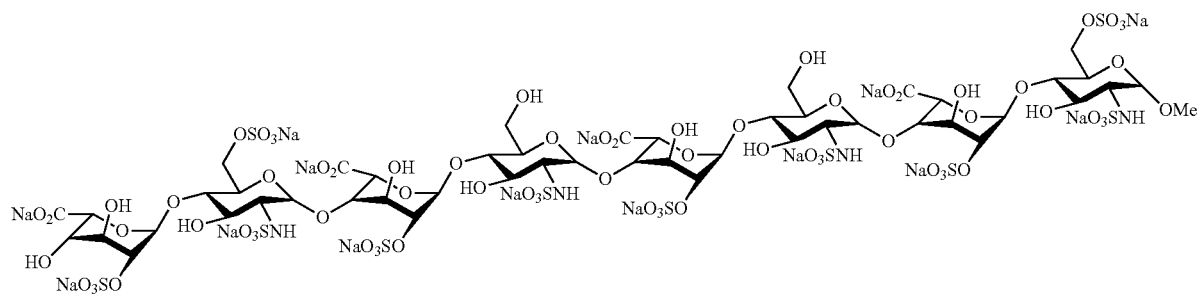

6

Compound 99 (8.9 mg, 4.28 μmol) is treated according to the same procedure as that described for the preparation of Example 1 to give compound 6 (7.3 mg).

$^1$H NMR [600 MHz] (D$_2$O) δ of the anomeric protons: 5.46; 5.32 (2H); 5.26; 5.25; 5.21; 5.20; 5.05 ppm.

Mass: "ESI" method, negative mode: theoretical mass=2489.55; experimental mass: 2488.00±1.5 a.m.u.

Example 7

Methyl(sodium 2-O-sodium sulfonato-α-L-idopyranosyluronate)-(1→4)-(2-deoxy-6-O-sodium sulfonato-2-sodium (sulfonatoamino)-α-D-glucopyranosyl)-(1→4)-(sodium 2-O-sodium sulfonato-α-L-idopyranosyluronate)-(1→4)-(2-deoxy-2-sodium (sulfonatoamino)-α-D-glucopyranosyl)-(1→4)-(sodium 2-O-sodium sulfonato-α-L-idopyranosyluronate)-(1→4)-(2-deoxy-6-O-sodium sulfonato-2-sodium (sulfonatoamino)-α-D-glucopyranosyl)-(1→4)-(sodium 2-O-sodium sulfonato-α-L-idopyranosyluronate)-(1→4)-2-deoxy-6-O-sodium sulfonato-2-sodium (sulfonatoamino)-α-D-qlucopyranoside (compound 7)

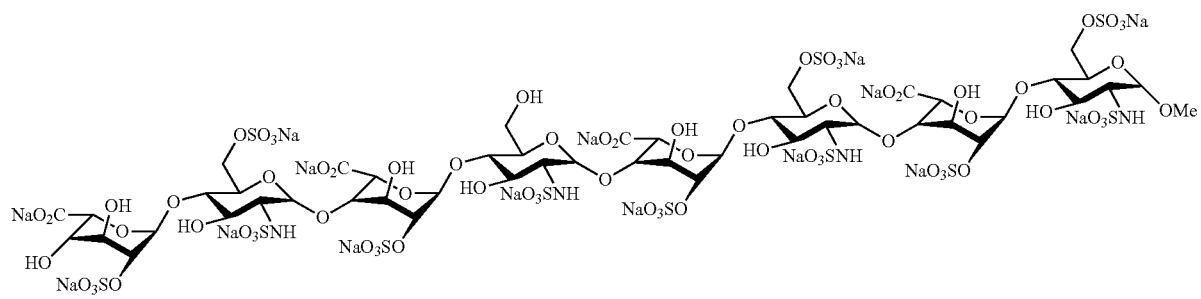

Compound 108 (3.7 mg, 1.42 µmol) is treated according to the same procedure as that described for the preparation of Example 1 to give compound 7 (1.8 mg).

$^1$H NMR [600 MHz] (D$_2$O) δ of the anomeric protons: 5.46; 5.42; 5.31; 5.26; 5.24; 5.22; 5.18; 5.03 ppm.

Example 8

Methyl(sodium 2-O-sodium sulfonato-α-L-idopyranosyluronate)-(1→4)-(2-deoxy-6-O-sodium sulfonato-2-sodium (sulfonatoamino)-α-D-glucopyranosyl)-[(1→4)-(sodium 2-O-sodium sulfonato-α-L-idopyranosyluronate)-(1→4)-(2-deoxy-6-O-sodium sulfonato-2-sodium sulfonatoamino-α-D-glucopyranos]$_2$-(1→4)-(sodium 2-O-sodium sulfonato-α-L-idopyranosyluronate)-(1→4)-2-deoxy-6-O-sodium sulfonato-2-(sulfonato)amino-α-D-glucopyranoside (compound 8)

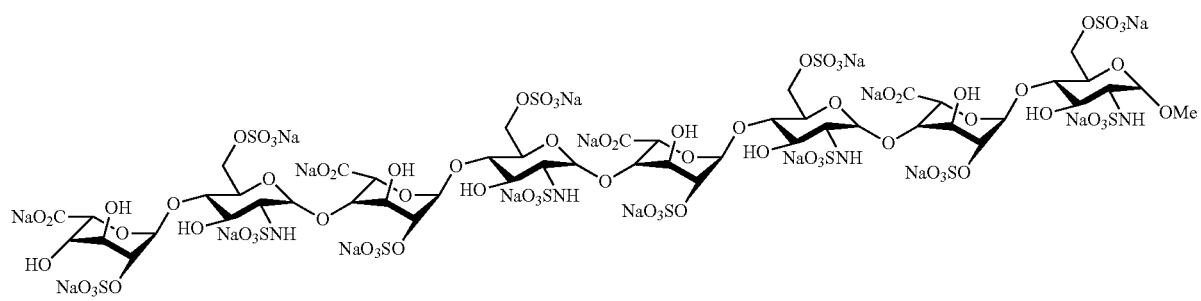

Compound III (42 mg, 18.4 μmol) is treated according to the same procedure as that described for the preparation of Example 1 to give compound 8 (44.1 mg).

$^1$H NMR [600 MHz] (D$_2$O) δ of the anomeric protons: 5.45; 5.44; 5.25; 5.24 (2H); 5.20; 5.04 ppm.

Mass: "ESI" method, negative mode: theoretical mass=2693.84; experimental mass: 2692.97±0.18 a.m.u.

Example 9

Methyl(sodium 2-O-sodium sulfonato-α-L-idopyranosyluronate)-(1→4)-(2-deoxy-6-O-sodium sulfonato-2-sodium (sulfonato)amino-α-D-glucopyranosyl)-[(1→4)-(sodium 2-O-sodium sulfonato-α-L-idopyranosyluronate)-(1→4)-(2-deoxy-6-O-sodium sulfonato-2-sodium (sulfonatoamino)-α-D-glucopyranosyl)]$_2$-(1→4)-sodium 2-O-sodium sulfonato-α-L-idopyranosyluronate)-(1→4)-2-deoxy-2-sodium (sulfonatoamino)-α-D-glucopyranoside (compound 9)

Model of In Vitro Angiogenesis: Specific Activity Towards FGF2

The in vitro angiogenesis model corresponds to a rearrangement of human venous endothelial cells on a biological matrix. The matrix is made by dispensing, into each well of a 96-well plate (Becton Dickinson 353872), 60 μl of Matrigel® diluted to 1/3 (Growth factor reduced Matrigel®: Becton Dickinson 356230) in collagen (rat tail collagen, type I: Becton Dickinson 354249). The biological matrix hardens after 1 hour at 37° C.

Human venous endothelial cells (HUVEC ref: C-12200-Promocell) are seeded onto the biological matrix at 7800 cells/well in 120 μl of EBM® medium (Endothelial Basal Medium, Lonza C3121)+2% FCS (foetal calf serum—Lonza)+hEGF (Recombinant Human Epidermal Growth Factor—Lonza) 10 μg/ml. The cells are stimulated with FGF2 (R&D Systems/234—FSE-0 50) 10 ng/ml or with the

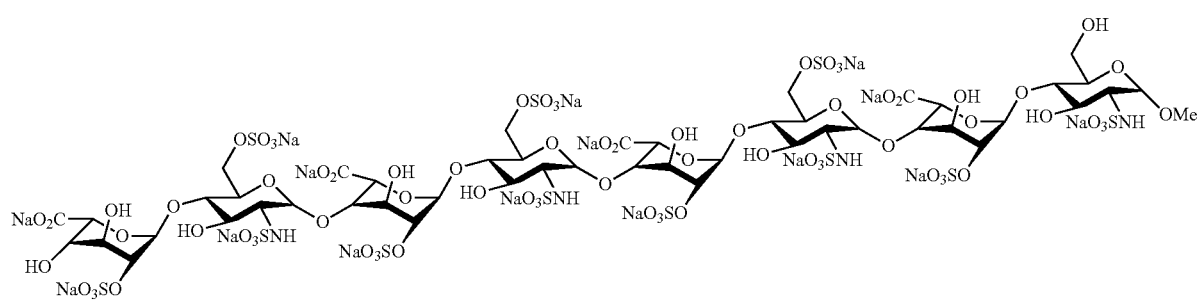

9

Compound 104 (6.5 mg, 2.98 μmol) is treated according to the same procedure as that described for the preparation of Example 1 to give compound 9 (6.0 mg).

$^1$H NMR [600 MHz] (D$_2$O) δ of the anomeric protons: 5.44 (2H); 5.43; 5.22 (2H); 5.19; 5.18; 5.05 ppm.

Mass: "ESI" method, negative mode: theoretical mass=2591.60; experimental mass: 2591.80±0.33 a.m.u.

The compounds according to the invention underwent pharmacological trials to determine their agonist effect on the FGF receptors and their activity on angiogenesis and also on post-ischaemic revascularization.

products of the invention for 18 hours at 37° C. in the presence of 5% CO$_2$. After 24 hours, the cells are observed under a microscope (×4 objective lens) and analysis of the length of the pseudo-tubules is performed with the aid of image software (Biocom VisioLab 2000 software).

In this test of in vitro angiogenesis, the compounds of the invention have a specific activity of between $10^{-6}$ M and $10^{-12}$ M. For example, compounds 1 and 7 are active at $10^{-6}$ M.

Compound 10 having the following formula:

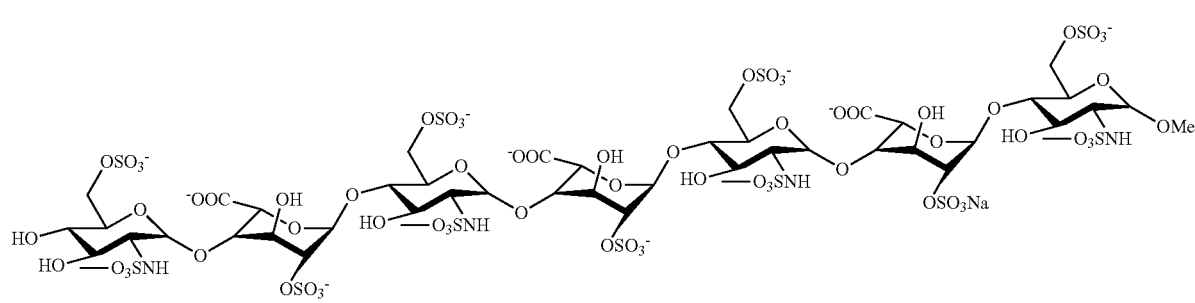

10 tested in sodium salt form, also demonstrated activity in this in vitro angiogenesis test.

Moreover, it was demonstrated in an in vitro cellular test that the octasaccharide No. 8 according to the invention, the heptasaccharide No. 3 and the decasaccharide No. 2 are better FGF-2 activators than the hexasaccharide analogue thereof (compound described by C. Tabeur et al. in Bioorg. & Med. Chem., 1999, 7, 2003-2012). Furthermore, the majority of the other octasaccharide compounds according to the invention, for instance compound No. 7, have the same activity as the octasaccharide No. 8 on in vitro models.

Model of Cellulose Implant in Mice

This model is an adaptation of the model described by Andrade et al. (Microvascular Research, 1997, 54, 253-61) for testing pharmacological products capable of activating the onset of angiogenesis.

The animals (white consanguineous BALB/c J mice) are anaesthetized with a xylazine (Rompun®, 10 mg/kg)/ketamine (Imalgene® 1000, 100 mg/kg) mixture intraperitoneally. The animal's back is shaved and disinfected with Hexomedine®. An air pocket is created subcutaneously on the mouse's back by injecting 5 ml of sterile air. An incision of about 2 cm at the top of the animal's back is made in order to introduce a sterile cellulose implant (disk 1 cm in diameter, 2 mm thick, Cellspon® ref. 0501) impregnated with 50 µl of sterile solution containing the test product. The incision is then sutured and cleaned with Hexomedine®.

On the days following the insertion of the implant, the mice can receive the product into the implant via an injection through the skin (50 µl/implant/day) under gaseous anaesthesia (5% isoflurane (Aerrane®, Baxter)).

Seven days after inserting the sponge, the mice are sacrificed by means of a lethal dose of pentobarbital sodium (CEVA Sante Animale), administered intraperitoneally. The skin is then excised, about 1 cm around the sponge, while avoiding the scar, so as to release the skin and the sponge. The sponge is then cut into several pieces and placed in a Ribolyser® containing 1 ml of lysis buffer (Cell Death Detection ELISA, Roche). The tubes are shaken four times consecutively, for 20 seconds, at force 4, using a cell mill (FastPrep® FP 120). The tubes are then centrifuged for 10 minutes at 2000×g at 20° C. and the supernatants are frozen at −20° C. until the time of the haemoglobin assay. On the day of the assay, the tubes are again centrifuged after thawing and the haemoglobin concentration is measured with the Drabkin reagent (Sigma, volume for volume) by reading on a spectrophotometer at 405 nm against a standard range of bovine haemoglobin (Sigma).

The haemoglobin concentration in each sample is expressed in mg/ml from the polynomial regression produced from the range. The results are expressed as a mean value (±sem) for each group. The differences between the groups are tested with an ANOVA followed by a Dunnett test on the square root of the values.

In this in vivo test, the compounds of the invention revealed a specific activity of between 5 and 45 ng/site. Thus, compounds 1 and 7 are active at a concentration of 45 ng/site.

It therefore appears that the compounds according to the invention have agonist activity on the FGF receptors and activity on angiogenesis, and also on post-ischaemic revascularization. These compounds may thus be used for the preparation of medicaments, especially medicaments that are useful for treating diseases that require activation of the FGF receptors, or of medicaments that are useful in pathologies requiring activation of angiogenesis post-ischaemic revascularization.

Thus, according to another of its aspects, a subject of the invention is thus medicaments that comprise a compound of formula (I)/(I') or compound 10, or a pharmaceutically acceptable salt thereof.

One subject of the invention is, more generally, medicaments comprising a compound of formula (I):

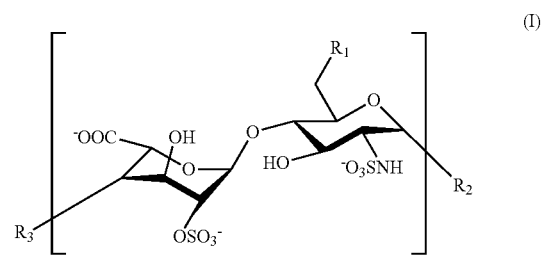

(I)

in which:
$R_1$ represents a group —$OSO_3^-$ or a hydroxyl group,
$R_2$ represents either a group —O-alkyl, or a monosaccharide of formula (II), in which R represents an alkyl group:

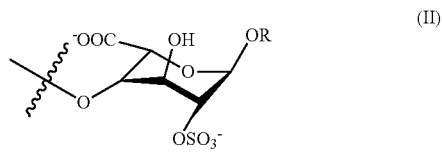

(II)

$R_3$ represents a disaccharide of formula (III):

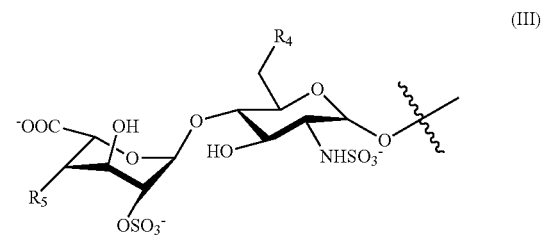

(III)

in which:
$R_4$ represents a group —$OSO_3^-$ or a hydroxyl group,
$R_5$ represents a disaccharide of formula (IV):

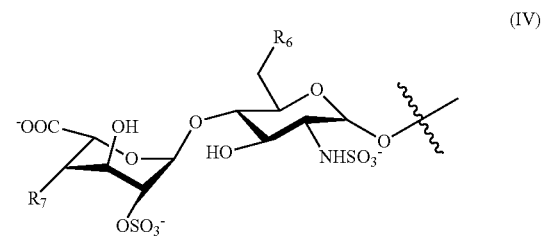

(IV)

in which:
$R_6$ represents a group —$OSO_3^-$ or a hydroxyl group,
$R_7$ represents either a hydroxyl group or a monosaccharide of formula (V) below, or a disaccharide of formula (VI):

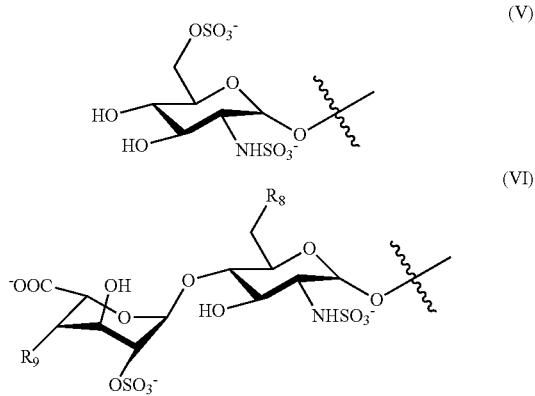

(V)

(VI)

in which:
R$_8$ represents a group —OSO$_3^-$ or a hydroxyl group,
R$_9$ represents either a hydroxyl group or a group —O-alkyl, or a disaccharide of formula (VII):

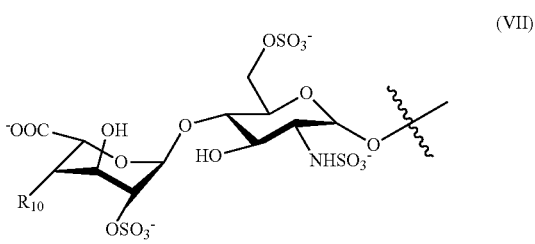

(VII)

in which R$_{10}$ represents a group —O-alkyl,
on condition that: R$_9$ represents a hydroxyl group or a group —O-alkyl when R$_2$ represents a monosaccharide of formula (II) as defined above; R$_7$ represents a disaccharide of formula (VI) as defined above when R$_2$ represents a group —O-alkyl; and R$_1$, R$_4$, R$_6$ and R$_8$ do not simultaneously represent hydroxyl groups.

Such compounds include those of formula (I)/(1) defined above, and also the heptasaccharide 10 defined previously, described in patent application US 2006/0079483 A1.

These medicaments find their use in therapy, especially in the treatment of ischaemia (cardiac ischaemia, arterial ischaemia of the lower limbs), the treatment of diseases associated with narrowing or obstruction of the arteries or arterites, the treatment of angina pectoris, the treatment of thromboangitis obliterans, the treatment of atherosclerosis, the treatment of inhibition of restenosis after angioplasty or endoarterectomy, the treatment of cicatrization, muscle regeneration treatment, treatment for the survival of myoblasts, the treatment of peripheral neuropathy, the treatment of post-operative nerve damage, the treatment of nerve deficiencies such as Parkinson's disease, Alzheimer's disease, prion disease and neuronal degeneration in alcoholics, the treatment of dementias, treatment for improving the survival of a bioartificial pancreas graft in the case of diabetics, treatment for improving the revascularization of grafts and the survival of grafts, the treatment of retinal degeneration, the treatment of pigmentary retinitis, the treatment of osteoarthritis, the treatment of pre-eclampsia or the treatment of vascular lesions and of acute respiratory distress syndrome, treatment for cartilage repairing, treatment for repairing and protecting bones, treatment for repairing and protecting hair follicles and for protecting and regulating hair growth.

Ischaemia is a decrease in arterial circulation in an organ, leading to a decrease in oxygen concentration in the damaged tissues. In the mechanisms of post-ischaemic revascularization, two main mechanisms are involved: angiogenesis and arteriogenesis. Angiogenesis is the process of generating new blood capillaries from pre-existing vessels. Arteriogenesis contributes towards the development (increase in size and calibre) of the collateral vessels around the ischaemic or avascular area.

Among the growth factors involved in these revascularization processes, the FGF family and especially FGF-2 has been the most widely described (Post, M. J., Laham, R., Sellke, F. W. & Simons, M. Therapeutic angiogenesis in cardiology using protein formulations. Cardiovasc. Res. 49, 522-31, 2001).

Thus, FGF2 and its receptors represent very pertinent targets for therapies directed towards inducing angiogenesis and arteriogenesis processes (Khurana, R. & Simons, M. Insights from angiogenesis trials using fibroblast growth factor for advanced arteriosclerotic disease. Trends Cardiovasc. Med. 13, 116-22, 2003).

One of the applications of the compounds of the invention is post-ischaemic treatment after heart occlusion or occlusion of the peripheral arteries. As regards the treatment of cardiac ischaemia, one of the most promising clinical tests is a clinical test in which FGF-2 was sequestered in alginate microspheres in the presence of heparin (Laham, R. J. et al. Local perivascular delivery of basic fibroblast growth factor in patients undergoing coronary bypass surgery: results of a phase I randomized, double-blind, placebo-controlled trial. Circulation 100, 1865-71, 1999). These microspheres were implanted close to the ischaemic locus in the myocardium. After 90 days, all the patients treated with FGF2 showed no ischaemic cardiac symptoms. In comparison, in the control group, three of the seven patients had persistent symptoms at 90 days and two patients required vascular surgery. Interestingly, the therapeutic benefit was maintained after 3 years of monitoring. These observations suggest that compounds that mimic FGF2 may represent a therapy of choice for treating the consequences of cardiac ischaemia.

Three clinical tests on the injection of FGF2 into the coronary artery were performed during treatment of narrowing of the coronary arteries (Laham, R. J. et al. Intracoronary basic fibroblast growth factor (FGF-2) in patients with severe ischemic heart disease: results of a phase I open-label dose escalation study. J. Am. Coll. Cardiol. 36, 2132-9, 2000; Simons, M. et al. Pharmacological treatment of coronary artery disease with recombinant fibroblast growth factor-2: double-blind, randomized, controlled clinical trial. Circulation 105, 788-93, 2002; Unger, E. F. et al. Effects of a single intracoronary injection of basic fibroblast growth factor in stable angina pectoris. Am. J. Cardiol. 85, 1414-9, 2000). The result of these three tests shows that intracoronary infusions of FGF2 are well tolerated and significantly improve the condition of the patients. Thus, the compounds described in the invention may find an application in the treatment of diseases associated with narrowing of the coronary arteries and especially in the treatment of angina pectoris.

Diseases of the distal arteries and especially arteritis of the lower limbs are caused by chronic obstruction of the arterioles that irrigate the extremities. These pathologies mainly affect the lower limbs. In a phase I clinical trial, patients with peripheral artery pathologies leading to claudication received injections of FGF2 (Lazarous, D. F. et al., Basic fibroblast growth factor in patients with intermittent claudication: results of a phase I trial. J. Am. Coll. Cardiol.

36, 1239-44, 2000). In this context, FGF2 was well tolerated in these patients and the clinical data suggest a beneficial effect of FGF2 and especially on improving walking. These clinical data suggest that the compounds of the invention represent a therapeutic tool of choice for the treatment of diseases associated with obstruction of the distal arteries.

Buerger's disease or thromboangitis obliterans affects the distal vascular structures and is characterized by distal arteritis of the legs, with pain and ulceration. In this context, an induction of angiogenesis and of vasculogenesis would represent a therapy for this pathology. The compounds of the said invention represent a therapy of choice for thromboangitis obliterans.

Peripheral neuropathy is an axonal or demyelinizing attack of the motor and/or sensory peripheral nerve which leads to desensitization of the distal limbs. One of the major secondary complications of diabetes is the chronic development of peripheral neuropathy. In this context, it has been demonstrated that FGF2 induces axonal regeneration, which might be a therapy of choice in the treatment of peripheral nerve lesion and thus in peripheral neuropathy (Basic fibroblast growth factor isoforms promote axonal elongation and branching of adult sensory neurons in vitro. Klimaschewski L, Nindl W, Feurle J, Kavakebi P, Kostron H. Neuroscience. 2004; 126(2):347-53). By virtue of the agonist activity on the FGF receptors, the compounds of the said invention would represent a treatment of choice in peripheral neuropathy in the case of healthy or diabetic patients.

It is clearly established that FGF2 is an activator of nerve cells during development. Recent results suggest that FGF2 is also a pivotal factor for promoting the regeneration of neurons in adults (Sapieha P S, Peltier M, Rendahl K G, Manning W C, Di Polo A., Fibroblast growth factor-2 gene delivery stimulates axon growth by adult retinal ganglion cells after acute optic nerve injury. Mol. Cell. Neurosci. 2003 November; 24(3):656-72.). By virtue of their agonist activities on the FGF receptors, the compounds of the said invention would represent a treatment of choice in repairing post-operative nerve damage, in repairing nerve deficiencies such as Parkinson's disease, Alzheimer's disease, prion disease and neuronal degeneration in alcoholics or in the case of dementia.

The proliferation and migration of vascular smooth muscle cells contributes towards intimal hypertrophy of the arteries and thus plays a predominant role in atherosclerosis and in restenosis after angioplasty and endoarterectomy. It has been demonstrated that an angiogenic factor, VEGF, significantly reduces the thickening of the intima by accelerating re-endothelialization (Van Belle, E., Maillard, L., Tio, F. O. & Isner, J. M. Accelerated endothelialization by local delivery of recombinant human vascular endothelial growth factor reduces in-stent intimal formation. Biochem. Biophys. Res. Commun. 235, 311-6, 1997). Thus, the compounds of the present invention, with pro-angiogenic activity, may be useful in treatment of atherosclerosis and in inhibiting restenosis after angioplasty or endoarterectomy.

The vascular network is essential to the development and maintenance of tissues. By promoting the delivery of nutrients, oxygen and cells, the blood vessels help to maintain the functional and structural integrity of tissues. In this context, angiogenesis and vasculogenesis make it possible to preserve and to perfuse tissues after ischaemia. The angiogenic growth factors such as VEGF and FGF2 thus promote revascularization for tissue regeneration. The compounds presented in the invention could represent a treatment of choice in muscle regeneration treatment.

The processes of muscle regeneration on dystrophic or normal muscles depend on the supply of cytokines and of angiogenic growth factors at the local level (Fibbi, G., D'Alessio, S., Pucci, M., Cerletti, M. & Del Rosso, M. Growth factor-dependent proliferation and invasion of muscle satellite cells require the cell-associated fibrinolytic system. Biol. Chem. 383, 127-36, 2002). It has been proposed that the FGF system is a critical system of muscle regeneration and of myoblast survival and proliferation (Neuhaus, P. et al. Reduced mobility of fibroblast growth factor (FGF)-deficient myoblasts might contribute to dystrophic changes in the musculature of FGF2/FGF6/mdx triple-mutant mice. Mol. Cell. Biol. 23, 6037-48, 2003). FGF2 and the compounds of the said invention could be exploited in order to promote cardiac regeneration. They would thus improve the perfusion of the myocardium after ischaemia (Hendel, R. C. et al. Effect of intracoronary recombinant human vascular endothelial growth factor on myocardial perfusion: evidence for a dose-dependent effect. Circulation 101, 118-21, 2000) and also the survival and progress of transplanted myoblasts, especially in Duchenne's muscular dystrophy.

Angiogenesis is an essential phenomenon during cutaneous cicatrization. The new vessels formed supply the oxygen and nutrients required for tissue repair. In the case of diabetics, cicatrization is a slow and difficult process presenting angiogenesis defects. FGFs are among the growth factors that are the most involved in angiogenesis processes during the cicatrization phase. Certain FGFs are highly overregulated in dermal cells after a cutaneous injury. On account of their agonist activity on the FGF receptors, the compounds of the said invention would represent a therapy of choice for the treatment of cicatrization in healthy or diabetic patients.

Bioartificial pancreas transplantation is a very promising technique for the treatment of certain types of diabetes. It has been demonstrated, in diabetic rats, that vascularization in bioartificial pancreases is much greater when the pancreases are impregnated with microspheres bearing FGF2 (Sakurai, Tomonori; Satake, Akira, Sumi, Shoichiro, Inoue, Kazutomo, Nagata, Natsuki, Tabata, Yasuhiko. The Efficient Prevascularization Induced by Fibroblast Growth Factor 2 With a Collagen-Coated Device Improves the Cell Survival of a Bioartificial Pancreas. Pancreas. 28(3):e70-e79, April 2004). This revascularization thus improves the survival of implanted bioartificial pancreases and consequently the survival of the graft. By virtue of their agonist activities on the FGF receptors, the compounds of the said invention would represent a therapy of choice in improving the survival of bioartificial pancreas grafts in diabetics and more generally in improving the revascularization of grafts and consequently the survival of the grafts.

Pigmentary retinitis is a pathology involving progressive degeneration of the retina characterized by degeneration of the photoreceptors and obliteration of the retinal vessels. Landenranta et al. (An anti-angiogenic state in mice and humans with retinal photoreceptor cell degeneration. Proc. Natl. Acad. Sci. USA 98, 10368-73, 2001) have proposed that angiogenic growth factors regulate the neural coordination and the associated vascularization of the retina by simultaneously functioning as photoreceptor survival factors and as endothelial cell regulators. In this context, the intravitreal injection of FGF2 retards the degeneration of the photoreceptors by acting on retinal survival and retinal angiogenesis (Faktorovich, E. G., Steinberg, R. H., Yasumura, D., Matthes, M. T. & LaVail, M. M. Basic fibroblast growth factor and local injury protect photoreceptors from light damage in the rat. J. Neurosci. 12, 3554-67, 1992). These observations demonstrate the interest of the compounds described in the invention as a therapy in retinal degeneration and especially in pigmentary retinitis.

In the field of osteoarthritis, many studies have been performed for restoring destroyed articular cartilage. In this context, it has been reported that the proliferation and differentiation of chondrocytes were stimulated by FGF2 in vitro (Kato Y, Gospodarowicz D. Sulfated proteoglycan synthesis by confluent cultures of rabbit costal chondrocytes grown in the presence of fibroblast growth factor. J. Cell Biol. 1985 February; 100(2):477-85). Furthermore, Cuevas et al. have shown that FGF2 induces cartilage repair in vivo (Cuevas P, Burgos J, Baird A. Basic fibroblast growth factor (FGF) promotes cartilage repair in vivo. Biochem. Biophys. Res. Commun. 1988 Oct. 31; 156(2):611-8). Takafuji et al. have also shown that FGF2 implants significantly improve temporo-mandibular cartilage in rabbits suffering from osteoarthritis (Takafuji H, Suzuki T, Okubo Y, Fujimura K, Bessho K Regeneration of articular cartilage defects in the temporomandibular joint of rabbits by fibroblast growth factor-2: a pilot study. Int. J. Oral Maxillofac. Surg. 2007 October; 36(10):934-7). These observations demonstrate the interest the compounds described in the invention as a therapy in treatment of osteoarthritis and cartilage repair.

In the field of bone repair, one of the essential needs is to find agents that stimulate bone formation. Among the main growth factors, it is established that the systemic administration of FGF2 facilitates bone repair (Acceleration of fracture healing in nonhuman primates by fibroblast growth factor-2. Kawaguchi H, Nakamura K, Tabata Y, Ikada Y, Aoyama I, Anzai J, Nakamura T, Hiyama Y, Tamura M. J. Clin. Endocrinol. Metab. 2001 February; 86(2), 875-880). The local application of FGF2 in gelatin matrices accelerates bone repair in primates, suggesting the clinical utility of FGF2 in the treatment of fractures. By virtue of their agonist properties for the FGF receptors, the compounds of the said invention would represent a treatment of choice in bone repair.

Pre-eclampsia is a pathology of the placenta associated with a vascularization defect (Sherer, D. M. & Abulafia, O. Angiogenesis during implantation, and placental and early embryonic development. Placenta 22, 1-13, 2001). These vascularization defects are thought to be due to an angiogenesis defect and lead to placental disruptions that may result in the death of the fetus. The compounds of the invention may be a treatment of choice for overcoming an angiogenesis defect in pre-eclamptic placentas.

In addition to angiogenesis-inducing effects, growth factors such as VEGF or FGF2 protect endothelial cells against intrinsic and extrinsic apoptosis inducers. The intrinsic signalling pathway is activated by the mitochondria in response to a stress such as deprivation or DNA damage, whereas the extrinsic signalling pathway is induced by the binding of pro-apoptotic factors such as TNF-α or Fas. It is now clearly described that VEGF and FGF2 are two factors of endothelial cell survival (Role of Raf in Vascular Protection from Distinct Apoptotic Stimuli: A Alavi, J. D. Hood, R. Frausto, D. G. Stupack, D. A. Cheresh: Science 4 Jul. 2003: Vol. 301. No. 5629, pp. 94-96). Acute respiratory distress syndrome (ARDS) is characterized by cardiovascular and neuropsychiatric problems. In the context of the cardiovascular problems, the patients present major vascular lesions and especially a high induction of apoptosis of endothelial cells. Recently, Hamacher et al. have demonstrated that the bronchoalveolar lavage fluids of patients suffering from ARDS showed pro-apoptotic activity against lung microvascular endothelial cells (Tumor necrosis factor-alpha and angiostatin are mediators of endothelial cytotoxicity in bronchoalveolar lavages of patients with acute respiratory distress syndrome. Am. J. Respir. Crit. Care Med. 2002 Sep. 1; 166(5):651-6: Hamacher J., Lucas R., Lijnen H. R., Buschke S., Dunant Y., Wendel A., Grau G. E., Suter P. M., Ricou B.). By virtue of their activity on endothelial cell survival, the products of the invention might be a treatment of choice in the vascular improvement of patients suffering from vascular lesions and especially patients suffering from ARDS.

The endogenous overregulation of FGF7 (or KGF) and of FGF18 appears to be an important mechanism for promoting the proliferation, migration and protection of hair follicles in pathological cases or after a tumoral treatment (Comprehensive Analysis of FGF and FGFR Expression in Skin: FGF18 Is Highly Expressed in Hair Follicles and Capable of Inducing Anagen from Telogen Stage Hair Follicles. Mitsuko Kawano, Akiko Komi-Kuramochi, Masahiro Asada, Masashi Suzuki, Junko Oki, Ju Jiang and Toru Imamura). By virtue of their agonist activity on the FGF receptors, the compounds of the said invention might be a treatment of choice for repairing and protecting hair follicles and for protecting and regulating hair growth.

According to another of its aspects, the present invention relates to pharmaceutical compositions comprising, as active principle, a compound according to the invention or a compound 10. These pharmaceutical compositions contain an effective dose of at least one compound according to the invention or of compound 10, or a pharmaceutically acceptable salt of the said compound, and also at least one pharmaceutically acceptable excipient. The said excipients are chosen, according to the pharmaceutical form and the desired mode of administration, from the usual excipients known to those skilled in the art.

Thus, one subject of the invention is a pharmaceutical composition comprising, as active principle, at least one compound of formula (I) in which:

$R_1$ represents a group —$OSO_3^-$ or a hydroxyl group, $R_2$ represents either a group —O-alkyl, or a monosaccharide of formula (II), in which R represents an alkyl group:

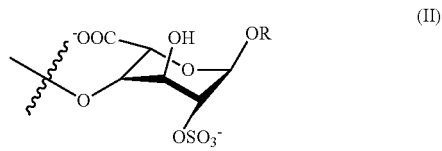

(II)

$R_3$ represents a disaccharide of formula (III):

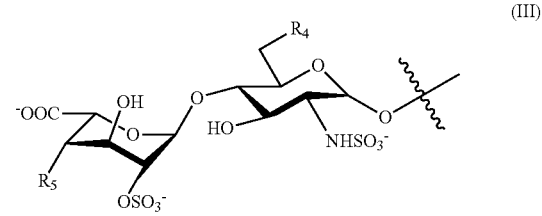

(III)

in which:
$R_4$ represents a group —$OSO_3^-$ or a hydroxyl group,
$R_5$ represents a disaccharide of formula (IV):

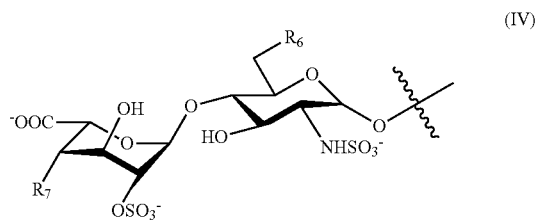

(IV)

in which:
$R_6$ represents a group —$OSO_3^-$ or a hydroxyl group,
$R_7$ represents either a hydroxyl group or a monosaccharide of formula (V) below, or a disaccharide of formula (VI):

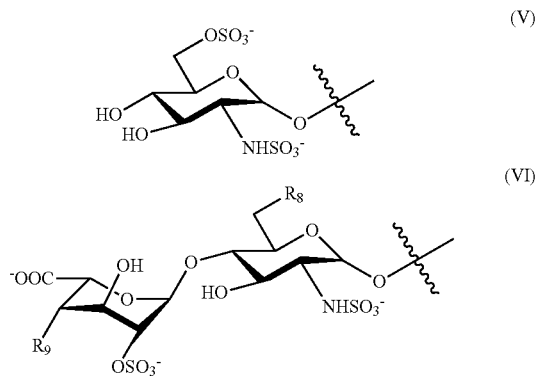

(V)

(VI)

in which:
$R_8$ represents a group —$OSO_3^-$ or a hydroxyl group,
$R_9$ represents either a hydroxyl group or a group —O-alkyl, or a disaccharide of formula (VII):

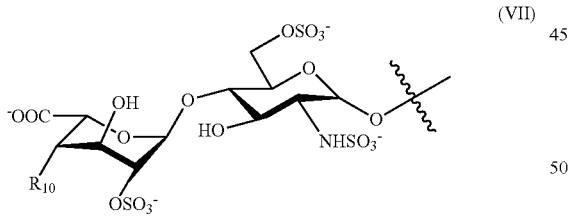

(VII)

in which $R_{10}$ represents a group —O-alkyl,
on condition that: $R_9$ represents a hydroxyl group or a group —O-alkyl when $R_2$ represents a monosaccharide of formula (II) as defined above; $R_7$ represents a disaccharide of formula (VI) as defined above when $R_2$ represents a group —O-alkyl; and $R_1$, $R_4$, $R_6$ and $R_8$ do not simultaneously represent hydroxyl groups,
or a pharmaceutically acceptable salt of the said compound, and also at least one pharmaceutically acceptable excipient.

Compounds of this kind encompass those of formula (I)/(I') defined above, as well as heptasaccharide 10 defined above, which has been described in patent application US 2006/0079483 A1.

In the pharmaceutical compositions of the present invention for oral, sublingual, subcutaneous, intramuscular, intravenous, topical, local, intratracheal, intranasal, transdermal or rectal administration, the active principle above or the salt thereof may be administered in a unit administration form, as a mixture with standard pharmaceutical excipients, to man and animals for the prevention or treatment of the above disorders or diseases.

The appropriate unit administration forms include oral forms such as tablets, soft or hard gel capsules, powders, granules and oral solutions or suspensions, sublingual, buccal, intratracheal, intraocular, intranasal or inhalation administration forms, topical, transdermal, subcutaneous, intramuscular or intravenous administration forms, rectal administration forms and implants. For topical application, the compounds according to the invention may be used in creams, gels, ointments or lotions.

The injectable administration forms are particularly advantageous, conventionally comprising the active compound dissolved in water for injection, in the presence of sodium chloride. The unit dose of active compound should be suited to the desired therapeutic effect; it may be, for example, between 0.1 and 100 mg of active principle.

According to another of its aspects, the present invention also relates to the use of a compound according to the invention or of a compound 10, or a pharmaceutically acceptable salt thereof, for treating the pathologies indicated above.

Thus, one subject of the invention is a compound of formula (I) in which:
$R_1$ represents a group —$OSO_3^-$ or a hydroxyl group,
$R_2$ represents either a group —O-alkyl, or a monosaccharide of formula (II), in which R represents an alkyl group:

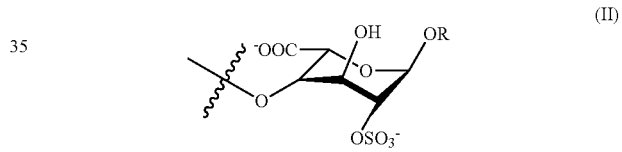

(II)

$R_3$ represents a disaccharide of formula (III):

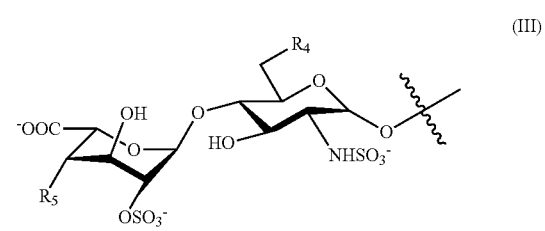

(III)

in which:
$R_4$ represents a group —$OSO_3^-$ or a hydroxyl group, and
$R_5$ represents a disaccharide of formula (IV):

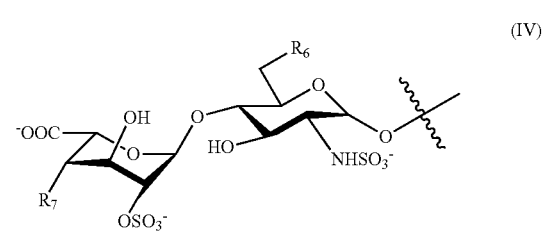

(IV)

in which:

$R_6$ represents a group —$OSO_3^-$ or a hydroxyl group, $R_7$ represents either a hydroxyl group or a monosaccharide of formula (V) below, or a disaccharide of formula (VI):

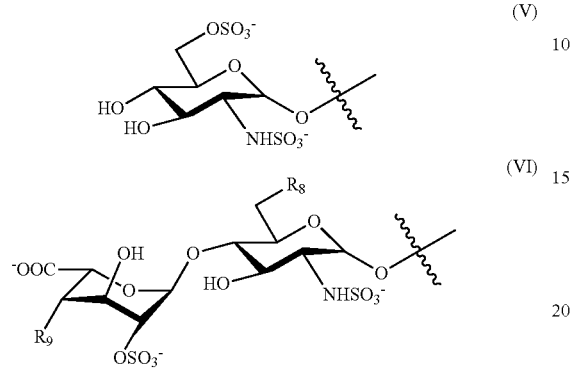

in which:

$R_8$ represents a group —$OSO_3^-$ or a hydroxyl group, $R_9$ represents either a hydroxyl group or a group —O-alkyl, or a disaccharide of formula (VII):

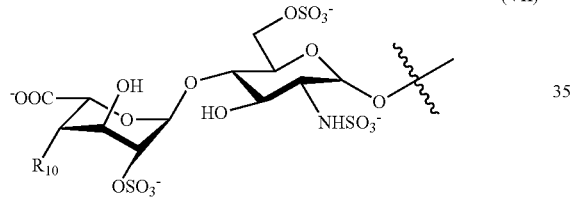

in which $R_{10}$ represents a group —O-alkyl, on condition that: $R_9$ represents a hydroxyl group or a group —O-alkyl when $R_2$ represents a monosaccharide of formula (II) as defined above; $R_7$ represents a disaccharide of formula (VI) as defined above when $R_2$ represents a group —O-alkyl; and $R_1$, $R_4$, $R_6$ and $R_8$ do not simultaneously represent hydroxyl groups, or a pharmaceutically acceptable salt of the said compound, for treating the pathologies indicated above.

Compounds of this kind encompass those of formula (I)/(I') defined above, as well as heptasaccharide 10 defined above, which has been described in patent application US 2006/0079483 A1.

According to another of its aspects, the present invention also relates to a method for treating the pathologies indicated above, which comprises the administration to patients of an effective dose of a compound according to the invention or of a compound 10 or a pharmaceutically acceptable salt thereof.

The medicaments, pharmaceutical compositions and treatment method according to the invention may also concern any of the subgroups of compounds defined previously.

What is claimed is:

1. An oligosaccharide compound of formula (I):

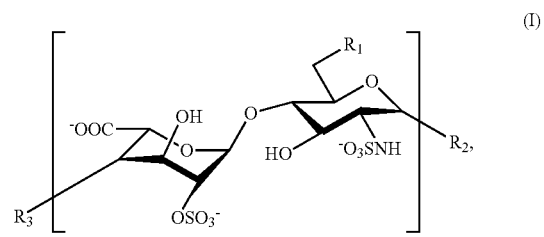

in which $R_1$ represents a group —$OSO_3^-$ or a hydroxyl group;

$R_2$ represents a monosaccharide of formula (II), in which R represents an alkyl group,

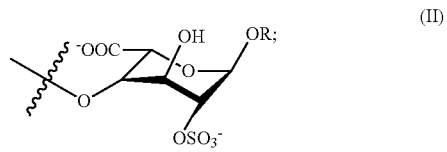

$R_3$ represents a disaccharide of formula (III):

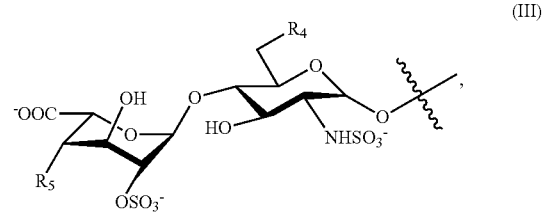

in which $R_4$ represents a group —$OSO_3^-$ or a hydroxyl group;

$R_5$ represents a disaccharide of formula (IV):

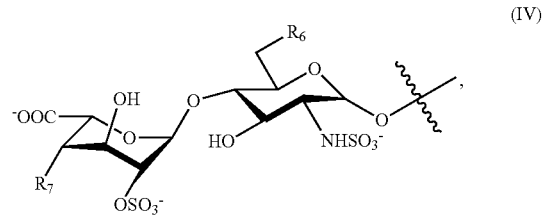

in which $R_6$ represents a group —$OSO_3^-$ or a hydroxyl group; and $R_7$ represents a hydroxyl group;

in acid form or in the form of a pharmaceutically acceptable salt thereof.

2. An oligosaccharide compound of formula (I):

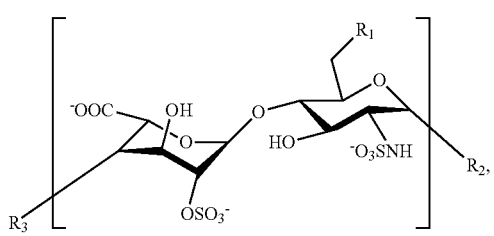
(I)

in which
  $R_1$ represents a group —$OSO_3^-$ or a hydroxyl group;
  $R_2$ represents a group —O-alkyl, wherein the alkyl group is selected from the group consisting of methyl, ethyl, isopropyl, butyl, isobutyl and tert-butyl;
  $R_3$ represents a disaccharide of formula (III):

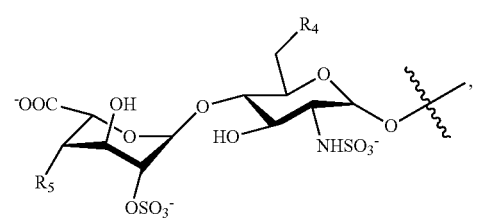
(III)

in which
  $R_4$ represents a group —$OSO_3^-$ or a hydroxyl group; and
  $R_5$ represents a disaccharide of formula (IV):

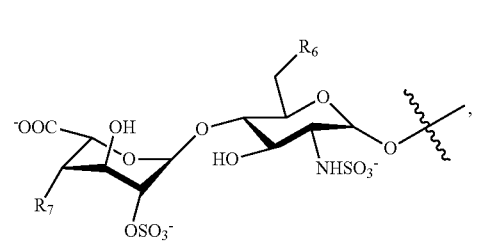
(IV)

in which
  $R_6$ represents a group —$OSO_3^-$ or a hydroxyl group; and
  $R_7$ represents a disaccharide of formula (VI):

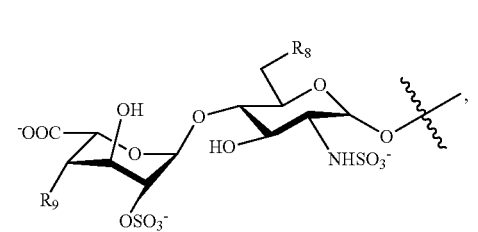
(VI)

in which
  $R_8$ represents a group —$OSO_3^-$ or a hydroxyl group; and
  $R_9$ represents a disaccharide of formula (VII);

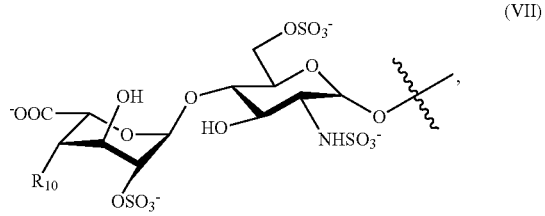
(VII)

in which $R_{10}$ represents a group —O-alkyl;
on condition that: $R_9$ represents a hydroxyl group or a group O-alkyl when $R_2$ represents a monosaccharide of formula (II) as defined above; $R_7$ represents a disaccharide of formula (VI) as defined above when $R_2$ represents a group O-alkyl; and $R_1$, $R_4$, $R_6$ and $R_8$ do not simultaneously represent hydroxyl groups;
in acid form or in the form of a pharmaceutically acceptable salt thereof.

3. An oligosaccharide compound of formula (I):

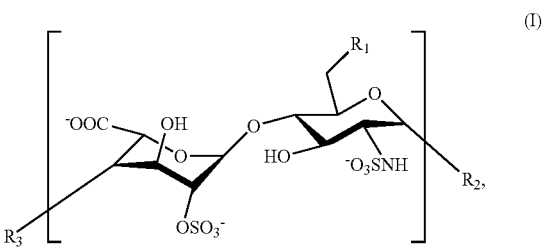
(I)

in which
  $R_1$ represents a group —$OSO_3^-$ or a hydroxyl group;
  $R_2$ represents a group —O-alkyl, wherein the alkyl group is selected from the group consisting of methyl, ethyl, isopropyl, butyl, isobutyl and tert-butyl;
  $R_3$ represents a disaccharide of formula (III):

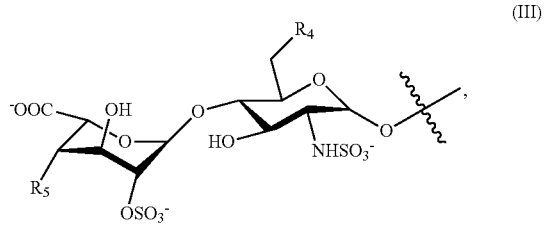
(III)

in which
  $R_4$ represents a group —$OSO_3^-$ or a hydroxyl group; and
  $R_5$ represents a disaccharide of formula (IV):

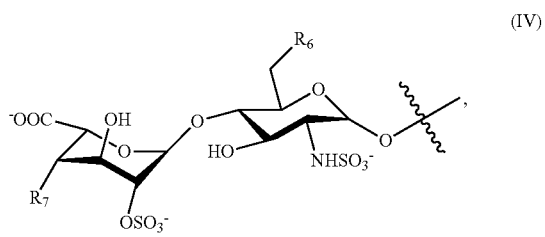
(IV)

in which
R₆ represents a group —OSO₃⁻ or a hydroxyl group;
R₇ represents a disaccharide of formula (VI):

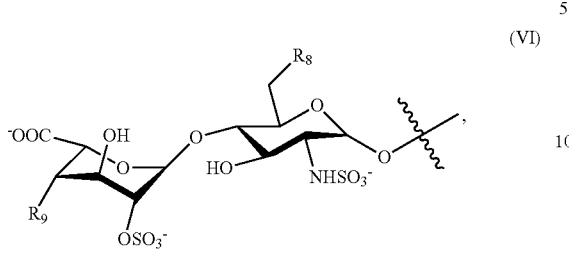

(VI)

in which
R₈ represents a group —OSO₃⁻ or a hydroxyl group; and
R₉ represents a group —O-alkyl,
on condition that R₁, R₄, R₆ and R₈ do not simultaneously represent hydroxyl groups;
in acid form or in the form of a pharmaceutically acceptable salt thereof.

4. An oligosaccharide compound selected from the group consisting of:
methyl (sodium 4-O-propyl-2-O-sodium sulfonato-α-L-idopyranosyluronate)-(1→4)-(2-deoxy-6-O-sodium sulfonato-2-sodium (sulfonatoamino)-α-D-glucopyranosyl)-(1→4)-[(sodium 2-O-sodium sulfonato-α-L-idopyranosyluronate)-(1→4)-(2-deoxy-6-O-sodium sulfonato-2-sodium (sulfonatoamino)-α-D-glucopyranosyl-(1→4)]₂-(sodium 2-O-sodium sulfonato-α-L-idopyranosyluronate)-(1→4)-2-deoxy-6-O-sodium sulfonato-2-sodium (sulfonatoamino)-α-D-glucopyranoside (No. 1);
methyl (sodium 4-O-propyl-2-O-sodium sulfonato-α-L-idopyranosyluronate)-(1→4)-(2-deoxy-6-O-sodium sulfonato-2-sodium (sulfonatoamino)-α-D-glucopyranosyl)-(1→4)-[(sodium 2-O-sodium sulfonato-α-L-idopyranosyluronate)-(1→4)-(2-deoxy-6-O-sodium sulfonato-2-sodium (sulfonatoamino)-α-D-glucopyranosyl-(1→4)]₃-(sodium 2-O-sodium sulfonato-α-L-idopyranosyluronate)-(1→4)-2-deoxy-6-O-sodium sulfonato-2-sodium (sulfonatoamino)-α-D-glucopyranoside (No. 2); and
sodium [methyl (sodium 2-O-sodium sulfonato-α-L-idopyranosyluronate)-(1→4)-(2-deoxy-6-O-sodium sulfonato-2-sodium (sulfonatoamino)-α-D-glucopyranosyl)-(1→4)-[(sodium 2-O-sodium sulfonato-α-L-idopyranosyluronate)-(1→4)-(2-deoxy-6-O-sodium sulfonato-2-sodium (sulfonatoamino)-α-D-glucopyranosyl)-(1→4)]₂-2-O-sodium sulfonato-α-L-idopyranoside]-uronate (No. 3).

5. A pharmaceutical composition comprising an oligosaccharide compound, in acid form or in the form of a pharmaceutically acceptable salt thereof, according to claim 1, and at least one pharmaceutically acceptable excipient.

6. A pharmaceutical composition comprising an oligosaccharide compound, in acid form or in the form of a pharmaceutically acceptable salt thereof, according to claim 4, and at least one pharmaceutically acceptable excipient.

7. A pharmaceutical composition comprising an oligosaccharide compound, in acid form or in the form of a pharmaceutically acceptable salt thereof, according to claim 3, and at least one pharmaceutically acceptable excipient.

8. A pharmaceutical composition comprising an oligosaccharide compound, in acid form or in the form of a pharmaceutically acceptable salt thereof, according to claim 7, and at least one pharmaceutically acceptable excipient.

\* \* \* \* \*